(12) United States Patent
Cook et al.

(10) Patent No.: US 9,133,141 B2
(45) Date of Patent: *Sep. 15, 2015

(54) CYSTEINE AND CYSTINE BIOISOSTERES TO TREAT SCHIZOPHRENIA AND REDUCE DRUG CRAVINGS

(71) Applicants: Marquette University, Milwaukee, WI (US); UWM Research Foundation, Inc., Milwaukee, WI (US)

(72) Inventors: James M. Cook, Milwaukee, WI (US); David A. Baker, Grafton, WI (US); Edward Merle Johnson, II, Glendale, WI (US); Wenyuan Yin, Milwaukee, WI (US); Ranjit Singh Verma, Shorewood, WI (US)

(73) Assignees: Marquette University, Milwaukee, WI (US); UWM Research Foundation, Inc., Milwaukee, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/148,959

(22) Filed: Jan. 7, 2014

(65) Prior Publication Data

US 2014/0155440 A1 Jun. 5, 2014

Related U.S. Application Data

(63) Continuation-in-part of application No. 12/425,063, filed on Apr. 16, 2009.

(60) Provisional application No. 61/045,386, filed on Apr. 16, 2008.

(51) Int. Cl.
*C07D 271/06* (2006.01)
*C07D 249/08* (2006.01)
*C07D 413/12* (2006.01)
*C07K 5/062* (2006.01)
*C07K 5/103* (2006.01)

(52) U.S. Cl.
CPC ............ *C07D 271/06* (2013.01); *C07D 249/08* (2013.01); *C07D 413/12* (2013.01); *C07K 5/0606* (2013.01); *C07K 5/1008* (2013.01)

(58) Field of Classification Search
None
See application file for complete search history.

(56) References Cited

PUBLICATIONS

Anghern et al. In Journal of Medicinal Chemistry 2004, 47, 1487-1513.*

* cited by examiner

*Primary Examiner* — Dennis Heyer
(74) *Attorney, Agent, or Firm* — Quarles & Brady LLP

(57) ABSTRACT

The present invention provides cysteine and cystine bioisosteres for the treatment of schizophrenia and drug addiction. The invention further encompasses pharmaceutical compositions containing such bioisosteres and methods of using the bioisosteres for treatment of schizophrenia and drug addiction.

9 Claims, 60 Drawing Sheets

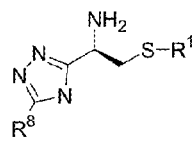
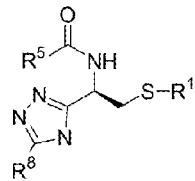

R¹ = H
   = tBu    O₂N
   = NBS = §-S-⟨phenyl⟩
R⁸ = H
   = CH₃
   = CH₂CH₃
   = CH(CH₃)₂
   = phenyl R¹ = H             R⁸ = H
   = tBu    O₂N      = CH₃
   = NBS = §-S-⟨phenyl⟩   = CH₂CH₃
R⁵ = CH₃          = CH(CH₃)₂
   = CH₂CH₃     = phenyl
   = CH(CH₃)₂
   = ⟨phenyl⟩

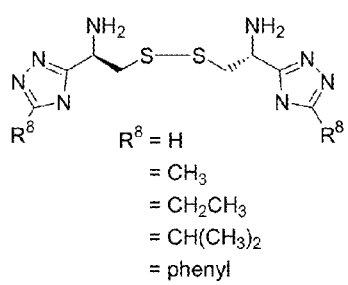
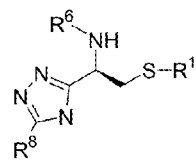

R⁸ = H
   = CH₃
   = CH₂CH₃
   = CH(CH₃)₂
   = phenyl

R¹ = H             R⁸ = H
   = tBu    O₂N      = CH₃
   = NBS = §-S-⟨phenyl⟩   = CH₂CH₃
R⁶ = Amino acid attached   = CH(CH₃)₂
     via the carboxylic acid  = phenyl
     side chain

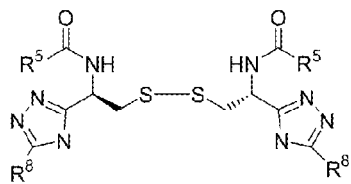
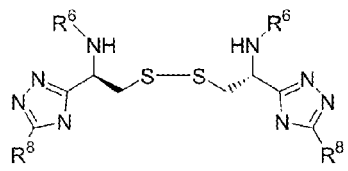

R⁵ = CH₃         R⁸ = H
   = CH₂CH₃     = CH₃
   = CH(CH₃)₂   = CH₂CH₃
   = ⟨phenyl⟩     = CH(CH₃)₂
                    = phenyl R⁶ = Amino acid attached   R⁸ = H
     via the carboxylic acid    = CH₃
     side chain              = CH₂CH₃
                                    = CH(CH₃)₂
                                    = phenyl

Fig. 3

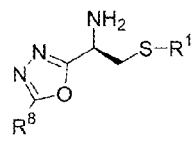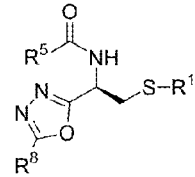

R¹ = H
  = tBu
  = NBS = ξ-S-⟨O₂N-phenyl⟩
R⁸ = H
  = CH₃
  = CH₂CH₃
  = CH(CH₃)₂
  = phenyl R¹ = H
  = tBu
  = NBS = ξ-S-⟨O₂N-phenyl⟩
R⁵ = CH₃
  = CH₂CH₃
  = CH(CH₃)₂
  = phenyl R⁸ = H
  = CH₃
  = CH₂CH₃
  = CH(CH₃)₂
  = phenyl

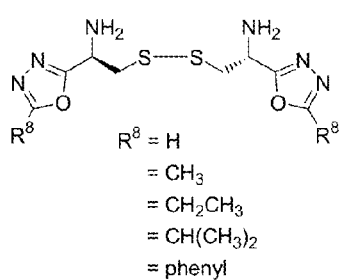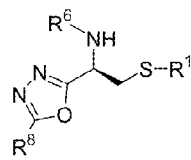

R⁸ = H
  = CH₃
  = CH₂CH₃
  = CH(CH₃)₂
  = phenyl

R¹ = H
  = tBu
  = NBS = ξ-S-⟨O₂N-phenyl⟩
R⁶ = Amino acid attached via the carboxylic acid side chain R⁸ = H
  = CH₃
  = CH₂CH₃
  = CH(CH₃)₂
  = phenyl

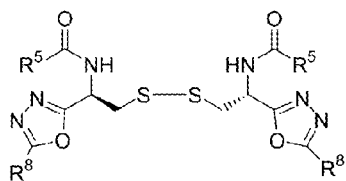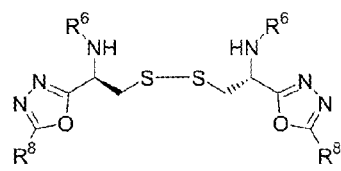

R⁵ = CH₃
  = CH₂CH₃
  = CH(CH₃)₂
  = phenyl
R⁸ = H
  = CH₃
  = CH₂CH₃
  = CH(CH₃)₂
  = phenyl R⁶ = Amino acid attached via the carboxylic acid side chain
R⁸ = H
  = CH₃
  = CH₂CH₃
  = CH(CH₃)₂
  = phenyl

Fig. 4

CYSTEINE AND CYSTINE BIOISOSTERES TO TREAT SCHIZOPHRENIA AND REDUCE DRUG CRAVINGS

CROSS-REFERENCE TO RELATED APPLICATIONS

This application is a continuation-in-part of U.S. application Ser. No. 12/425,063 filed on Apr. 16, 2009, which claims the benefit of U.S. provisional Application No. 61/045,386 filed Apr. 16, 2008. Each of these applications is incorporated by reference herein in its entirety.

FIELD OF THE INVENTION

This invention relates generally to the treatment of schizophrenia and drug addiction. More particularly, the present invention is directed to compounds representing cysteine and cystine bioisosteres useful as antipsychotic medications in the treatment of schizophrenia. As well, the respective bioisosteres are applicable for reducing drug cravings in drug addicted individuals.

BACKGROUND OF THE INVENTION

Schizophrenia is a debilitating disorder afflicting 1% of the world's population. The development of effective medications to treat schizophrenia is reliant on advances in characterizing the underlying pathophysiology. Chlorpromazine and other phenothiazines are considered first generation antipsychotics (termed "typical antipsychotics") useful in the treatment of schizophrenia. However, the antipsychotic efficacy of phenothiazines was, in fact, serendipitously discovered. These drugs were initially used for their antihistaminergic properties and later for their potential anesthetic effects during surgery. Hamon and colleagues extended the use of phenothiazines to psychiatric patients and quickly uncovered the antipsychotic properties of these compounds; shortly thereafter, the pharmacologic characteristic of dopamine receptor blockade was linked to the antipsychotic action of chlorpromazine (Thorazine). This led to the development of additional dopamine receptor antagonists, including haloperidol (Haldol). For nearly fifty years, dopamine antagonists were the standard treatment for schizophrenia even though these drugs induce severe side effects ranging from Parkinson's disease-like motor impairments to sexual dysfunction and are only effective in treating the positive symptoms of schizophrenia.

In the 1970's, clozapine became the first "atypical psychotic" or 2nd generation antipsychotic agent introduced. Clinical trials have shown that clozapine produces fewer motor side effects and exhibits improved efficacy against positive and negative symptoms relative to 1st generation compounds. However, clozapine was briefly withdrawn from the market because of the potential to produce severe agranulocytosis, a potentially fatal side effect requiring patients to undergo routine, costly hematological monitoring. As a result, clozapine is only approved for treatment-resistant schizophrenia. Although also a dopamine receptor antagonist, the therapeutic site of action for clozapine is thought to involve blockade of serotonin receptors. This led to the generation of other serotonin receptor antagonists in the 1990's with the goal of improving the safety profile of clozapine.

The growth potential for novel antipsychotics was revealed following the introduction of risperidone in 1994; within two years risperidone overtook haloperidol in the number of prescriptions written by physicians. While it was generally assumed that the newer 2nd generation antipsychotics also exhibited the favorable efficacy profile produced by clozapine, the clinical data was ambiguous. As a result, the NIH recently funded a large, lengthy, and expensive clinical trial to examine this assumption. The results of the Clinical Antipsychotic Trials of Intervention Effectiveness (CATIE), recently released, indicate that there is no benefit to the newer 2nd generation compounds. Specifically, 1st and 2nd generation drugs did not differ in the rate of discontinuation, which was on average 74% over an 18 month period, in part due to a lack of efficacy and intolerability of the treatment regimen.

As can be appreciated from the foregoing, there exists a pressing need and considerable market potential for novel antipsychotic agents. Of course, the development of effective antipsychotic agents will be facilitated by a thorough understanding of pathophysiologies underlying the neurological disorders.

SUMMARY OF THE INVENTION

The present invention is based on the inventors' success in identifying cysteine and cystine bioisosteres with utility in antipsychotic and drug addiction treatments.

In a first aspect, the invention provides a compound having the formula:

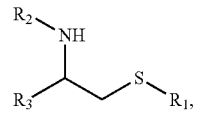

wherein $R_1$ is H, a branched or straight chain $C_1$ to $C_5$ alkyl, or

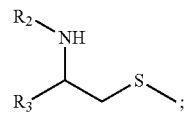

$R_2$ is H;

wherein $R_4$ is a branched or unbranched $C_1$-$C_6$ alkyl, $C_3$-$C_6$ cycloalkyl, $C_1$-$C_6$ alkoxy, aryloxy, benzyl, or phenyl; and $R_3$ is

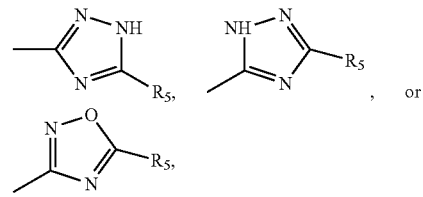

wherein $R_5$ is H, a branched or unbranched $C_1$-$C_6$ alkyl, $C_3$-$C_6$ cycloalkyl, phenyl, or benzyl; or a salt or hydrate of the compound.

In some embodiments, $R_1$ is H or

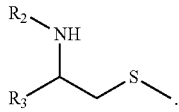

In some embodiments, $R_2$ is H or

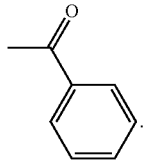

In some embodiments, $R_3$ is

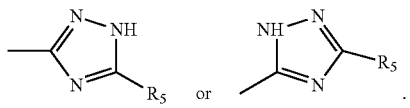

In some embodiments, $R_5$ is H, —$CH_2CH_3$, —$CH(CH_3)_2$, or phenyl.

In some embodiments, the compound has the formula:

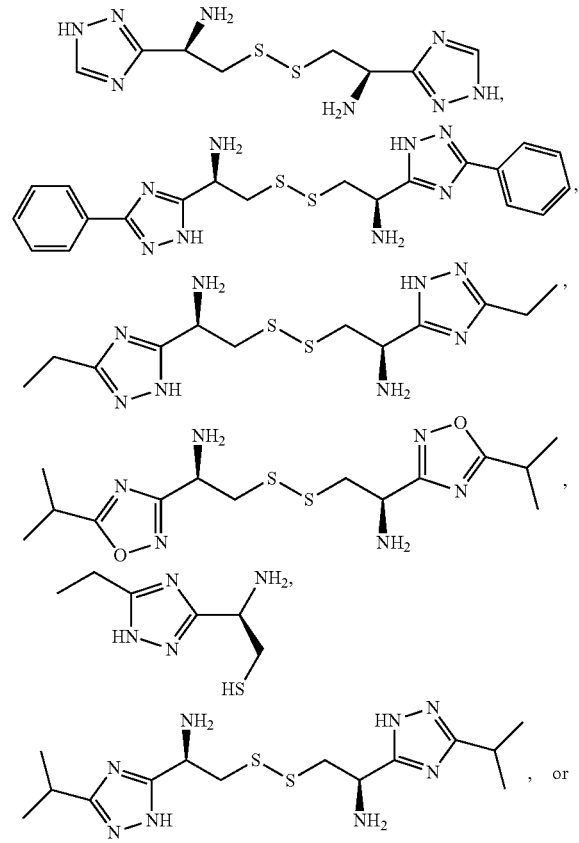

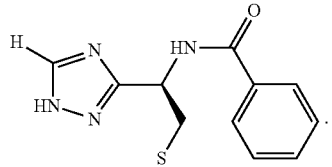

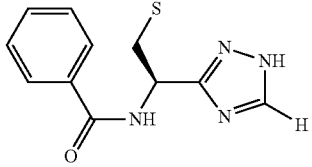

In some embodiments, the salts of the compounds that are encompassed by the invention are a hydrochloride salts.

In some embodiments, the invention encompasses a pharmaceutical composition comprising the compound described above, including possible salts and hydrates thereof, and a pharmaceutically-acceptable carrier.

In a second aspect, the invention encompasses a method of treating schizophrenia in a subject. The method includes the step of administering to the subject an effective amount of a compound as described above (or a salt or hydrate thereof), whereby schizophrenia is treated in the subject. In some embodiments, the step of administering the compound to the subject is accomplished by oral delivery.

In a third aspect, the invention encompasses a method of treating drug craving in a subject. The method includes the step of administering to the subject an effective amount of a compound as described above (or a salt or hydrate thereof), whereby drug craving is treated in the subject. In some embodiments, the step of administering the compound to the subject is accomplished by oral delivery.

The invention provides in a fourth aspect a compound having the formula:

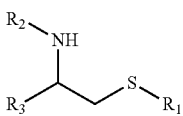

wherein $R_1$ is: H, a branched or straight chain $C_1$ to $C_5$ alkyl, a nitrobenzenesulfonyl, a trityl, an aryl thio, an aryl, an alkylthio, an acyl, a benzoyl, a thio acyl, a thio benzoyl, a carboxybenzyl, or a benzyl group;

$R_2$ is: H;

in which $R_4$ is selected from a branched or unbranched $C_1$-$C_6$ alkyl, $C_3$-$C_6$ cycloalkyl, $C_1$-$C_6$ alkoxy, aryloxy, benzyl, or phenyl;

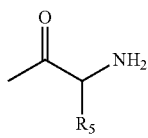

in which $R_5$ is a side chain of an amino acid selected from the side chains of Ala, Asn, Asp, Cys, Phe, Gly, His, Ile, Lys, Leu, Met, Pro, Arg, Ser, Thr, Val, Trp, Tyr, Gln, or Glu; and $R_3$ is:

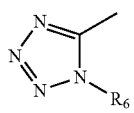

in which $R_6$ is H, a branched or unbranched $C_1$-$C_6$ alkyl, $C_3$-$C_6$ cycloalkyl, phenyl, or benzyl; or

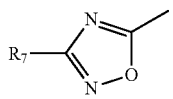

in which $R_7$ is H, a branched or unbranched $C_1$-$C_6$ alkyl, $C_3$-$C_6$ cycloalkyl, phenyl, or benzyl; or

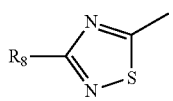

in which $R_8$ is H, a branched or unbranched $C_1$-$C_6$ alkyl, $C_3$-$C_6$ cycloalkyl, phenyl, or benzyl; or

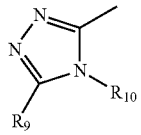

in which $R_9$ is H, a branched or unbranched $C_1$-$C_6$ alkyl, $C_3$-$C_6$ cycloalkyl, phenyl, or benzyl, and $R_{10}$ is H, a branched or unbranched $C_1$-$C_6$ alkyl, $C_3$-$C_6$ cycloalkyl, phenyl, or benzyl; or

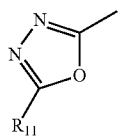

in which $R_{11}$ is H, a branched or unbranched $C_1$-$C_6$ alkyl, $C_3$-$C_6$ cycloalkyl, phenyl, or benzyl; or

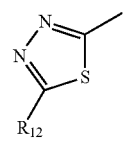

in which $R_{12}$ is H, a branched or unbranched $C_1$-$C_6$ alkyl, $C_3$-$C_6$ cycloalkyl, phenyl, or benzyl;

or a symmetric cystine dimer comprising two identical compounds, an unsymmetric cystine dimer comprising two different compounds, or a salt, solvate or hydrate of said compound or cystine dimer thereof.

In one embodiment, a compound according to the invention has the formula:

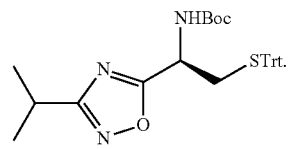

Compounds may also be provided in the form of dimers such as, for example, a symmetric cystine dimer having the formula:

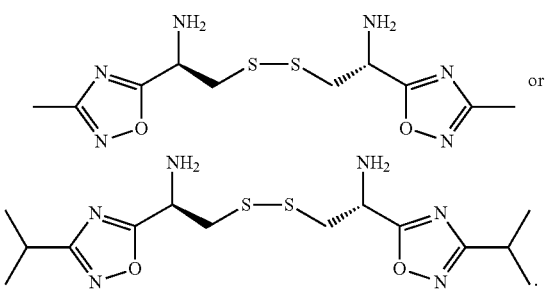

Alternatively, compounds may be provided in the form of a dimer bearing at least one protective group, such as, for example, a dimer having the formula:

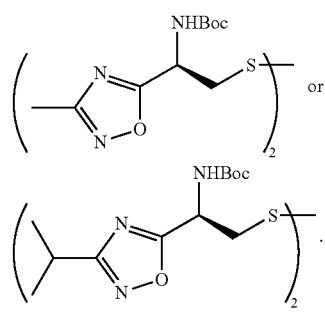

In another aspect, the invention provides a cystine dimer having the general formula:

A-B wherein said cystine dimer includes a first structure A having the formula:

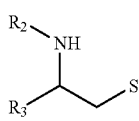

in which R$_2$ is: H;

in which R$_4$ is selected from a branched or unbranched C$_1$-C$_6$ alkyl, C$_3$-C$_6$ cycloalkyl, C$_1$-C$_6$ alkoxy, aryloxy, benzyl, or phenyl;

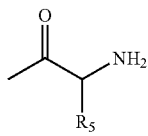

in which R$_5$ is a side chain of an amino acid selected from the side chains of Ala, Asn, Asp, Cys, Phe, Gly, His, Ile, Lys, Leu, Met, Pro, Arg, Ser, Thr, Val, Trp, Tyr, Gln, or Glu; and
R$_3$ is:

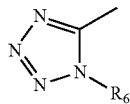

in which R$_6$ is H, a branched or unbranched C$_1$-C$_6$ alkyl, C$_3$-C$_6$ cycloalkyl, phenyl, or benzyl; or

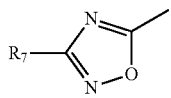

in which R$_7$ is H, a branched or unbranched C$_1$-C$_6$ alkyl, C$_3$-C$_6$ cycloalkyl, phenyl, or benzyl; or

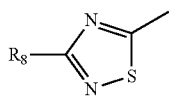

in which R$_8$ is H, a branched or unbranched C$_1$-C$_6$ alkyl, C$_3$-C$_6$ cycloalkyl, phenyl, or benzyl; or

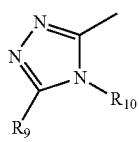

in which R$_9$ is H, a branched or unbranched C$_1$-C$_6$ alkyl, C$_3$-C$_6$ cycloalkyl, phenyl, or benzyl, and R$_{10}$ is H, a branched or unbranched C$_1$-C$_6$ alkyl, C$_3$-C$_6$ cycloalkyl, phenyl, or benzyl; or

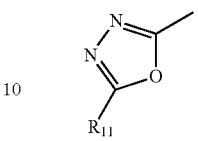

in which R$_{11}$ is H, a branched or unbranched C$_1$-C$_6$ alkyl, C$_3$-C$_6$ cycloalkyl, phenyl, or benzyl; or

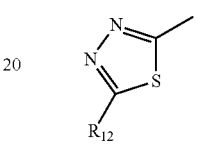

in which R$_{12}$ is H, a branched or unbranched C$_1$-C$_6$ alkyl, C$_3$-C$_6$ cycloalkyl, phenyl, or benzyl; and a second structure B having the formula:

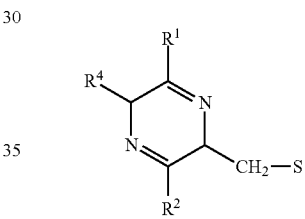

in which R$^1$ and R$^2$ are independently selected from OH, =O, or a branched or straight chain C$_1$ to C$_5$ alkoxyl group, with the caveat that when =O is selected the nitrogen atom adjacent the carbonyl group thusly formed bears a H and a single bond joins the adjacent nitrogen to said carbonyl group; and R$^4$ is selected from the side chain groups of the natural L-amino acids cys, gly, phe, pro, val, ser, arg, asp, asn, glu, gln, ala, his, ile, leu, lys, met, thr, trp, tyr, or D-isomers thereof; and wherein, in the general formula, structures A and B are linked by an —S—S— linkage, said —S—S— linkage formed by covalent linkage of the sulfur atoms contained in each of said structures.

In certain embodiments, the structure B has the formula:

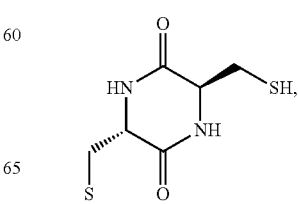

-continued

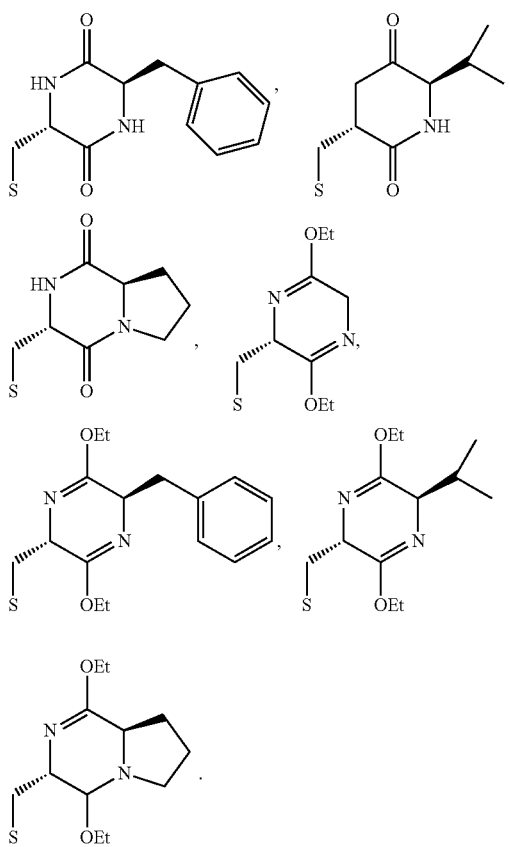

Representative cystine dimers include, for example, the dimer having the formula:

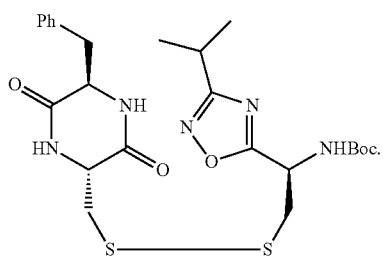 [SMILES: CC(C)c1noc([C@H](CSSC[C@@H]2NC(=O)[C@@H](Cc3ccccc3)NC2=O)NC(=O)OC(C)(C)C)n1]

In yet another aspect, the invention provides a cystine dimer having the general formula:

A-D wherein said cystine dimer includes a first structure A having the formula:

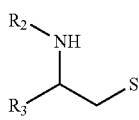

in which $R_2$ is: H;

in which $R_4$ is selected from a branched or unbranched $C_1$-$C_6$ alkyl, $C_3$-$C_6$ cycloalkyl, $C_1$-$C_6$ alkoxy, aryloxy, benzyl, or phenyl;

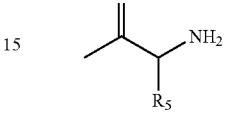

in which $R_5$ is a side chain of an amino acid selected from the side chains of Ala, Asn, Asp, Cys, Phe, Gly, His, Ile, Lys, Leu, Met, Pro, Arg, Ser, Thr, Val, Tip, Tyr, Gln, or Glu; and $R_3$ is:

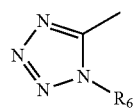

in which $R_6$ is H, a branched or unbranched $C_1$-$C_6$ alkyl, $C_3$-$C_6$ cycloalkyl, phenyl, or benzyl; or

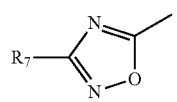

in which $R_7$ is H, a branched or unbranched $C_1$-$C_6$ alkyl, $C_3$-$C_6$ cycloalkyl, phenyl, or benzyl; or

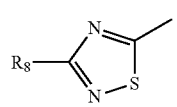

in which $R_8$ is H, a branched or unbranched $C_1$-$C_6$ alkyl, $C_3$-$C_6$ cycloalkyl, phenyl, or benzyl; or

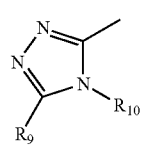

in which $R_9$ is H, a branched or unbranched $C_1$-$C_6$ alkyl, $C_3$-$C_6$ cycloalkyl, phenyl, or benzyl, and $R_{10}$ is H, a branched or unbranched $C_1$-$C_6$ alkyl, $C_3$-$C_6$ cycloalkyl, phenyl, or benzyl; or

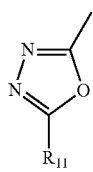

in which $R_{11}$ is H, a branched or unbranched $C_1$-$C_6$ alkyl, $C_3$-$C_6$ cycloalkyl, phenyl, or benzyl; or

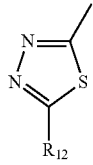

in which $R_{12}$ is H, a branched or unbranched $C_1$-$C_6$ alkyl, $C_3$-$C_6$ cycloalkyl, phenyl, or benzyl; and a second structure D having the formula:

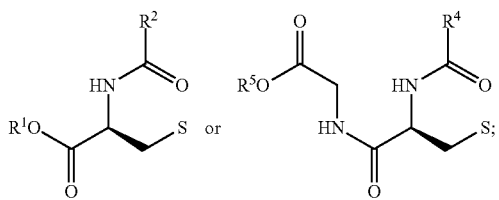

in which $R^1$, $R^2$, $R^4$, and $R^5$ are independently selected from a branched or straight chain $C_1$ to $C_5$ alkyl, a phenyl, or a benzyl group; and wherein, in the general formula, structures A and D are linked by an —S—S— linkage, said —S—S— linkage formed by covalent linkage of the sulfur atoms contained in each of said structures.

In certain embodiments, the structure D has the formula:

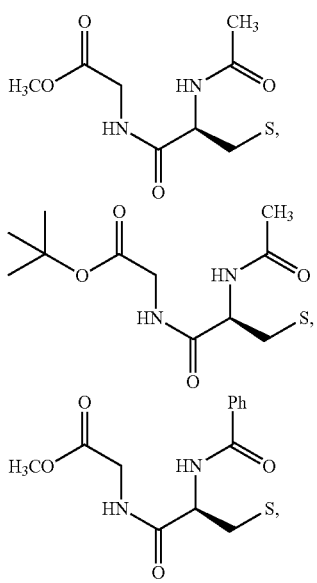

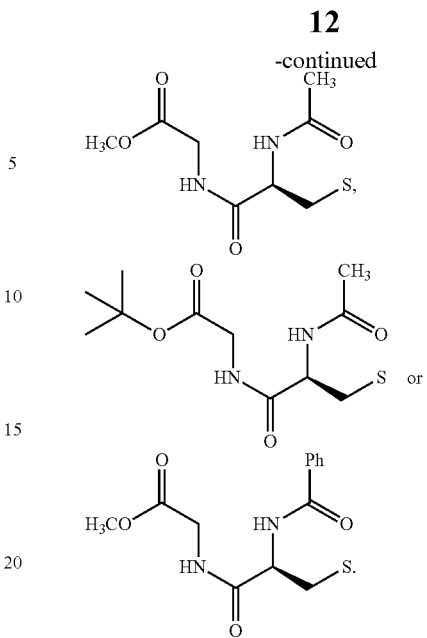

In a further aspect, the invention is directed to a cystine dimer having the general formula:

B-D wherein said cystine dimer includes a first structure B having the formula:

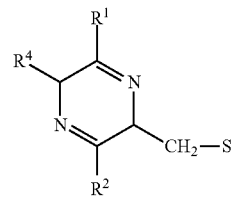

in which $R^1$ and $R^2$ are independently selected from OH, =O, or a branched or straight chain $C_1$ to $C_5$ alkoxyl group, with the caveat that when =O is selected the nitrogen atom adjacent the carbonyl group thusly formed bears a H and a single bond joins the adjacent nitrogen to said carbonyl group; and $R^4$ is selected from the side chain groups of the natural L-amino acids cys, gly, phe, pro, val, ser, arg, asp, asn, glu, gln, ala, his, ile, leu, lys, met, thr, trp, tyr, or D-isomers thereof; and a second structure D having the formula:

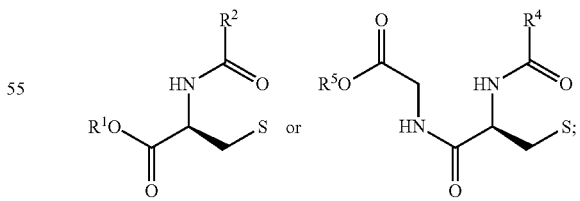

in which $R^1$, $R^2$, $R^4$, and $R^5$ are independently selected from a branched or straight chain $C_1$ to $C_5$ alkyl, a phenyl, or a benzyl group;

wherein, in the general formula, structures B and D are linked by an —S—S— linkage, said —S—S— linkage formed by covalent linkage of the sulfur atoms contained in each of said structures.

In certain embodiments, structure B may have, for example, the formula:

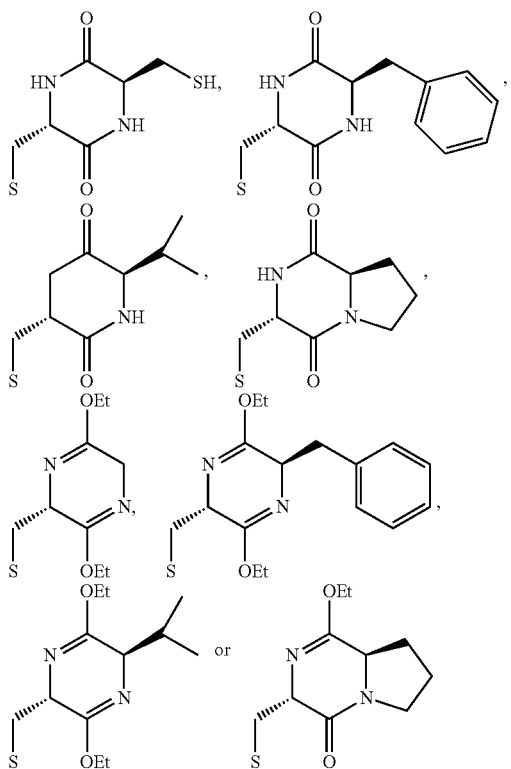

As well, structure D may have, for example, the formula:

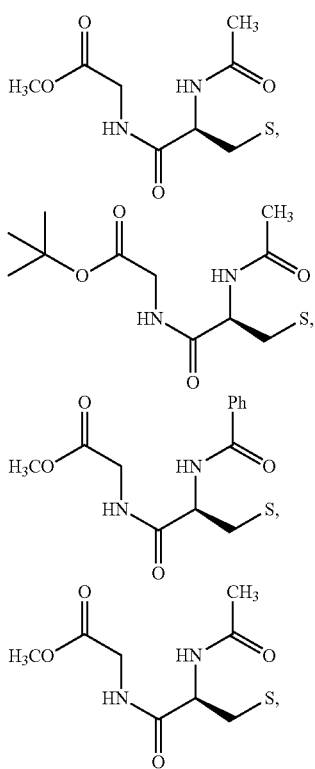

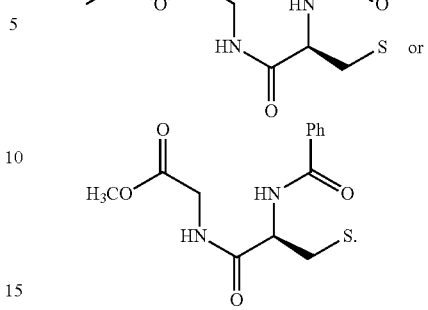

In another aspect, the invention is directed to a method of treating schizophrenia in a subject comprising administering to the subject an effective amount of a compound or dimer thereof as described and claimed herein, whereby schizophrenia is treated in the subject. The preferred route of administering to the subject is via oral delivery.

In another aspect, the invention provides a method of treating drug craving in a subject comprising administering to the subject an effective amount of a compound or dimer thereof according to the invention, whereby drug craving is treated in the subject. Again, the preferred route of administering to the subject is via oral delivery.

The invention further encompasses pharmaceutical compositions containing a compound or dimer thereof in combination with a pharmaceutically-acceptable carrier. Methods of formulating/manufacturing such pharmaceutical compositions (alternatively termed "medicaments") for the treatment of schizophrenia or for treating drug craving in a subject are, of course, within the invention's scope.

Other objects, features and advantages of the present invention will become apparent after review of the specification, claims and drawings.

BRIEF DESCRIPTION OF THE DRAWINGS

FIGS. 1-4 illustrate exemplary formulas for cysteine and cystine bioisosteres according to the present invention.

DETAILED DESCRIPTION OF THE INVENTION

Figure 1:
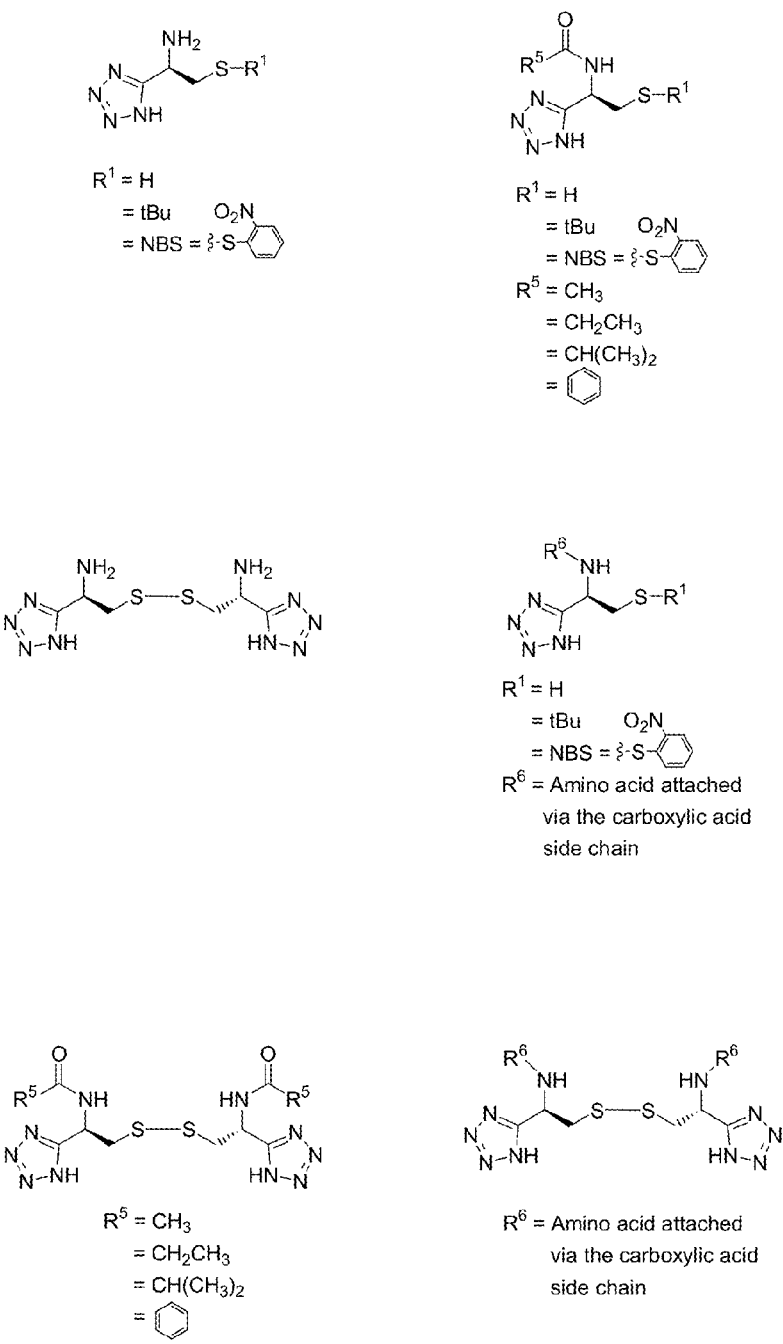
Figure 2:
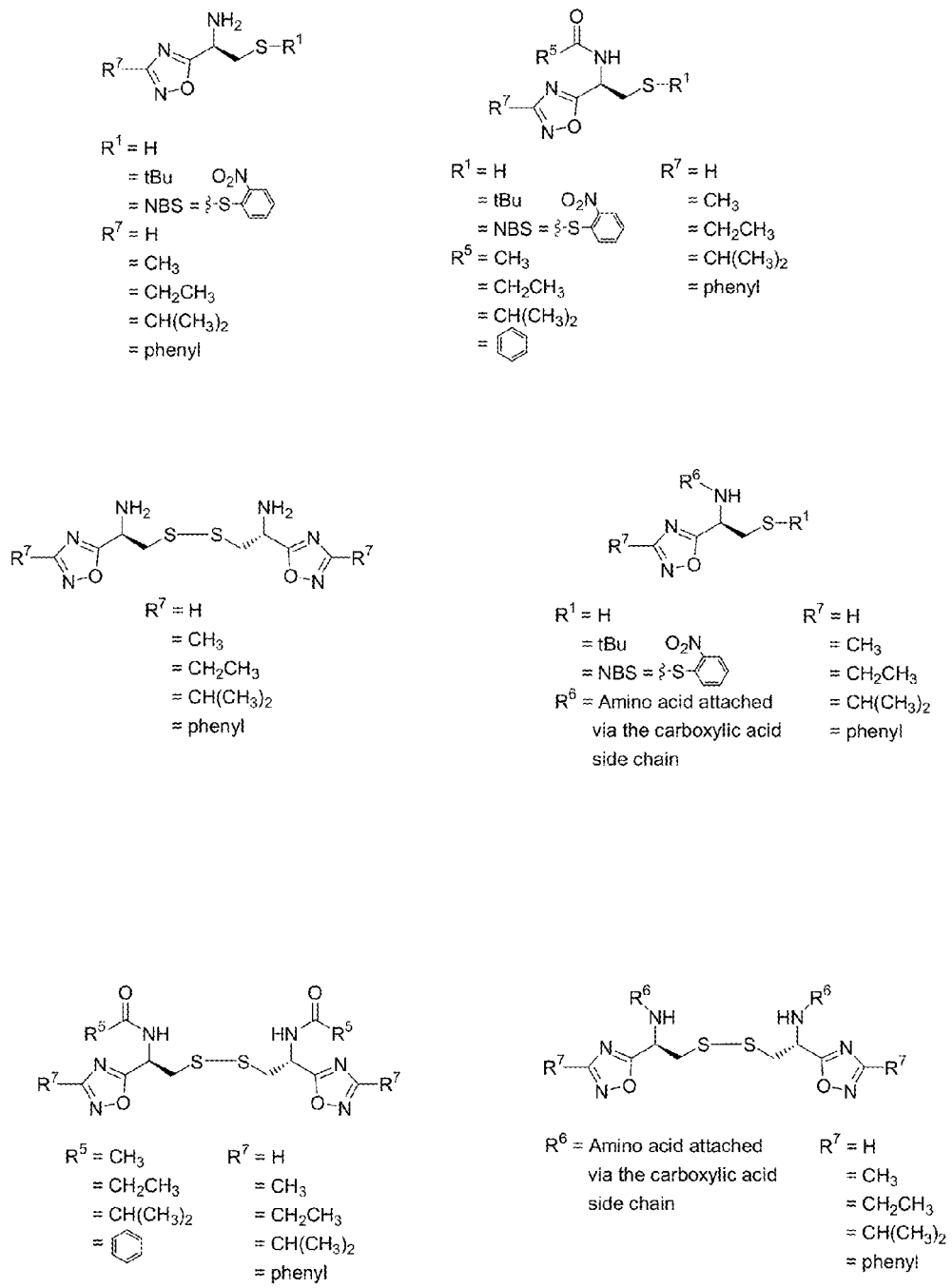

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

As used herein, the term "bioisostere" shall refer to a compound resulting from the exchange of an atom or of a group of atoms with another, broadly similar, atom or group of atoms. Such an exchange is termed a "bioisosteric replacement" and is useful to create a new compound with similar biological properties to the parent compound. The bioisosteric replacement may be physicochemically or topologically based. Bioisosteric replacement generally enhances desired biological or physical properties of a compound without making significant changes in chemical structure. For example, the replacement of a hydrogen atom with a fluorine atom at a site of metabolic oxidation in a drug candidate may prevent such metabolism from taking place. Because the fluorine atom is similar in size to the hydrogen atom the overall topology of the molecule is not significantly affected, leaving the desired biological activity unaffected. However, with a blocked pathway for metabolism, the drug candidate may have a longer half-life. Another example is aromatic rings, a phenyl —$C_6H_5$ ring can often be replaced by a different aromatic ring such as thiophene or naphthalene which may improve efficacy or change binding specificity of a respective bioisostere.

The term "lower alkyl group(s)" as used herein indicates a linear, branched or cyclic alkyl group(s) having 1 to 6 carbon atoms. They include, for example, methyl group, ethyl group, n-propyl group, n-butyl group, n-pentyl group, n-hexyl group, isopropyl group, isobutyl group, sec-butyl group, tert-butyl group, isopentyl group, tert-pentyl group, neopentyl group, 2-pentyl group, 3-pentyl group, 3-hexyl group, 2-hexyl group, cyclopropyl group, cyclobutyl group, cyclopentyl group and cyclohexyl group. In them, methyl group, ethyl group, etc. are preferred.

The term "aryl group(s)" as used herein indicates a monocyclic or bicyclic aromatic substituent(s) composed of 5 to 12 carbon atoms, such as phenyl group, indenyl group, naphthyl group and fluorenyl group. In them, phenyl group is preferred. The term "arylthio group" indicates a monocyclic or bicyclic aromatic substituent(s) composed of 5 to 12 carbon atoms and further including a thio moiety.

The term "alkoxy group" refers to an alkyl (carbon and hydrogen chain) group linked to oxygen thus: R—O. The term "aryloxy group" refers to an aryl group linked to oxygen thus: Ar—O.

The term "alkylthio group(s)" as used herein indicates an alkylthio group(s) having a linear, branched or cyclic alkyl group having 1 to 12 carbon atoms, preferably 1 to 5 carbon atoms, such as methylthio group, ethylthio group, n-propylthio group, isopropylthio group, n-butylthio group, isobutylthio group, sec-butylthio group, tert-butylthio group, cyclopropylthio group, cyclobutylthio group, cyclopentylthio group and cyclobutylthio group.

The term "acyl group(s)" as used herein indicates a formyl group, an acyl group(s) having a linear, branched or cyclic alkyl group having 1 to 6 carbon atoms, acyl group(s) having a linear, branched or cyclic alkenyl group having 1 to 6 carbon atoms, acyl group(s) having a linear, branched or cyclic alkynyl group having 1 to 6 carbon atoms or acyl group(s) having an aryl group which may be substituted, such as formyl group, acetyl group, propionyl group, butyryl group, isobutyryl group, valeryl group, isovaleryl group, pivaloyl group, hexanoyl group, acryloyl group, methacryloyl group, crotonoyl group, isocrotonoyl group, benzoyl group and naphthoyl group. Acyl groups having a heterocyclic ring can also be used, for example, furanyl carbonyl group, thienyl carbonyl group, isoxazolyl carbonyl group and thiazolyl carbonyl group.

The term "thio acyl group(s)" as used herein indicates a thio acyl group(s) having a linear, branched or cyclic alkyl group having 1 to 6 carbon atoms, thio acyl group(s) having a linear, branched or cyclic alkenyl group having 1 to 6 carbon atoms, thio acyl group(s) having a linear, branched or cyclic alkynyl group having 1 to 6 carbon atoms or thio acyl group(s) having an aryl group which may be substituted, such as formyl group, acetyl group, propionyl group, butyryl group, isobutyryl group, valeryl group, isovaleryl group, pivaloyl group, hexanoyl group, acryloyl group, methacryloyl group, crotonoyl group, isocrotonoyl group, benzoyl group and naphthoyl group. Thio acyl groups may be incorporated in a heterocyclic ring, for example, thienyl carbonyl group and thiazolyl carbonyl group.

The term "amino acid" refers to an organic acid containing an amino group. The term includes naturally occurring amino acids ("natural amino acids") such as alanine, valine, leucine, isoleucine, proline, phenylalanine, tryptophan, methionine, glycine, serine, threonine, cysteine, asparagine, glutamine, tyrosine, histidine, lysine, arginine, aspartic acid, and glutamic acid. Amino acids can be pure L or D isomers or mixtures of L and D isomers.

"Prodrugs" refers to compounds, including monomers and dimers of the compounds of the invention, which have cleavable groups and become under physiological conditions compounds which are pharmaceutically active in vivo.

The term "symmetric cystine dimer" shall refer to the chemical entity formed by disulfide linkage of two identical bioisosteres, diketopiperazine-based prodrugs, or protected cysteine analogs described herein. In similar fashion, the term "unsymmetric cystine dimer" shall refer to the chemical entity formed by disulfide linkage of two non-identical bioisosteres, diketopiperazine-based prodrugs, or protected cysteine analogs. The term unsymmetric cystine dimer shall further encompass those hybrid chemical entities formed by disulfide linkage of a cysteine bioisostere/diketopiperazine-based prodrug pair, as well as a cysteine bioisostere/protected cysteine analog pair.

"Subject" includes humans. The terms "human," "patient" and "subject" are used interchangeably herein.

"Therapeutically effective amount" means the amount of a compound that, when administered to a subject for treating a disease or disorder, is sufficient to effect such treatment for the disease or disorder. The "therapeutically effective amount" can vary depending on the compound, the disease or disorder and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder, or even preventing the same.

The present inventors have recently identified the cystine-glutamate antiporter as a highly novel cellular process that likely contributes to the pathology underlying schizophrenia. The present cysteine and cystine bioisosteres, useful to increase the activity of cystine-glutamate antiporters, appear capable of blocking sensorimotor gating deficits in the preclinical phencyclidine model of schizophrenia. Unlike existing medications, cysteine and cystine bioisosteres will exert antipsychotic properties, in part, by reversing pathology underlying the disease.

While no one theory or mechanism of pharmacological effect is adopted herein, cysteine and cystine bioisosteres appear to restore diminished signaling to glutamate receptors and diminished glutathione levels observed in schizophrenics. A depleted glutathione level can lead to increased oxidative stress, and impaired cystine-glutamate antiporter activity, glutamate neurotransmission, synaptic connection, and gene expression, all of which are observed in schizophrenia.

As a related matter, impaired cystine-glutamate antiporter activity and faulty glutamate neurotransmission bear on the issue of uncontrolled drug use, i.e., drug addiction. Uncontrolled drug use and heightened susceptibility to relapse are defining features of addiction that contribute to the transition in drug consumption from a recreational to a compulsive pattern. Long-term plasticity resulting in augmented excitatory neurotransmission within corticostriatal pathways in response to drugs of abuse have been implicated in addiction. Human cocaine abusers exposed to craving-inducing stimuli exhibit increased activation of excitatory circuits originating in cortical regions, including orbital and prefrontal cortex, and projecting to the ventral striatum; further, the degree of activation of corticostriatal pathways correlates with craving in humans (Breiter et al., 1997; Volkow et al., 1999; Volkow et al., 2005).

Preclinical data also indicate the existence of drug-induced plasticity leading to activation of corticostriatal pathways. Activation of these circuits results in heightened extracellular glutamate in the nucleus accumbens and stimulation of ionotropic glutamate receptors, both of which are necessary for cocaine primed reinstatement (Cornish and Kalivas, 2000; McFarland and Kalivas, 2001; Park et al., 2002; Baker et al., 2003; McFarland et al., 2003; Schmidt et al., 2005; Peters and Kalivas, 2006). Further, the dorsomedial prefrontal cortex has been shown to be necessary for reinstatement produced by exposure to drug-paired cues using the contextual reinstatement paradigm and in response to electrical foot shock (McFarland et al., 2004; Fuchs et al., 2005). As a result, identification of cellular mechanisms capable of regulating synaptic glutamate represent targets in the treatment of addiction (Kalivas et al., 2005).

Increased excitatory neurotransmission in the nucleus accumbens may arise, in part, by diminished activity of cystine-glutamate antiporters. Recent data collected by the present inventors illustrates that glutamate released from these antiporters provides endogenous tonic stimulation to group II or 2/3 metabotropic glutamate receptors (mGluRs) and thereby regulates synaptic glutamate and dopamine release. Thus, altered glutamate signaling could arise as a consequence of decreased cystine-glutamate exchange. Repeated cocaine administration has been shown to blunt the activity of cystine-glutamate exchange, which likely contributes to a sequence of events, including diminished group II mGluR autoregulation and increased excitatory neurotransmission in the nucleus accumbens (Baker et al., 2003, Madayag et al., 2007; Kau et al., 2008).

Cysteine prodrugs, such as N-acetylcysteine ("NAC"), are used to drive cystine-glutamate exchange by apparently elevating extracellular cystine levels, thereby creating a steep cystine concentration gradient. Preclinical studies have shown N-acetylcysteine to be effective in blocking compulsive drug-seeking in rodents (Baker et al., 2003). Further, extant clinical data also show a reduction in cocaine use and craving in cocaine abusers receiving NAC (Larowe et al., 2006). Unfortunately, the full clinical efficacy of targeting cystine-glutamate exchange may be unrealized when utilizing NAC due to extensive first-pass metabolism and limited passive transport of this drug across the blood-brain barrier. The drugs described and claimed herein will not be significantly eliminated by the liver and will readily pass the blood-brain barrier. Cysteine is the reduced form of cystine and is readily oxidized in vivo to cystine, thus elevating either cysteine or cystine is believed to increase cystine-glutamate exchange.

The cysteine prodrug NAC has been previously shown to have a favorable safety/tolerability profile in human subjects. In fact, NAC has been used for decades in humans for other indications (e.g., as a mucolytic, acetaminophen toxicity) and as an experimental treatment (HIV, cancer) without producing severe adverse effects. However, NAC undergoes extensive first pass metabolism requiring the usage of high doses that limit the utility of the drug and, potentially, increase the chances of side effects due to the buildup of metabolized by-products. The chemical entities presently disclosed and claimed herein are designed to substantially avoid the problem of first pass metabolism and therefore exhibit increased efficacy as compared to prior cysteine prodrugs.

Exemplary synthetic strategies are outlined in Schemes 1-4 which yield bioisosteres according to the present invention. The general rational in such strategies is to provide bioisosteres of the desired amino acids, L-cysteine and L-cystine, with improved partition coefficients in order to facilitate passive diffusion through the blood brain barrier and eliminate the need for intra- and extra-cellular peptidases to liberate the desired amino acids. It can be appreciated that these approaches will not lead to higher levels of cysteine/cystine in the brain, however, the bioisosteres of the invention will be recognized as cysteine/cystine analogs by the cystine-glutamate antiporter and function as such. Note, an exception to this is the use of mixed bioisosteres dimmer containing bioisostere components and diketopiperazine/protected analog components since the diketopoperazine component is, in fact, expected to generate cystine. The end result in physiological terms is increased glutamate levels in the extra-synaptic space of a human subject without increased production of glutathione unless a mixed bioisostere dimer is used in which one component includes a diketopiperazine/protected analog.

Outlined in Scheme 1 and Scheme 2 is the conversion of L-cysteine to bioisosteres of the carboxylic acid group, while outlined in Scheme 3 and Scheme 4 is a pathway to amide bioisosteres. The approaches described herein incorporate steps to protect cysteine residues to prevent side reactions during conversion to a corresponding bioisostere. As noted above, the purely bioisostere targets are unlikely to be metabolized or cleaved to produce cysteine or cystine; however, these compounds will be used to drive the cystine-glutamate antiporter, releasing glutamate into a subject's extra-cellular (extra-synaptic) space.

Synthesis of Carboxylic Acid Bioisosteres

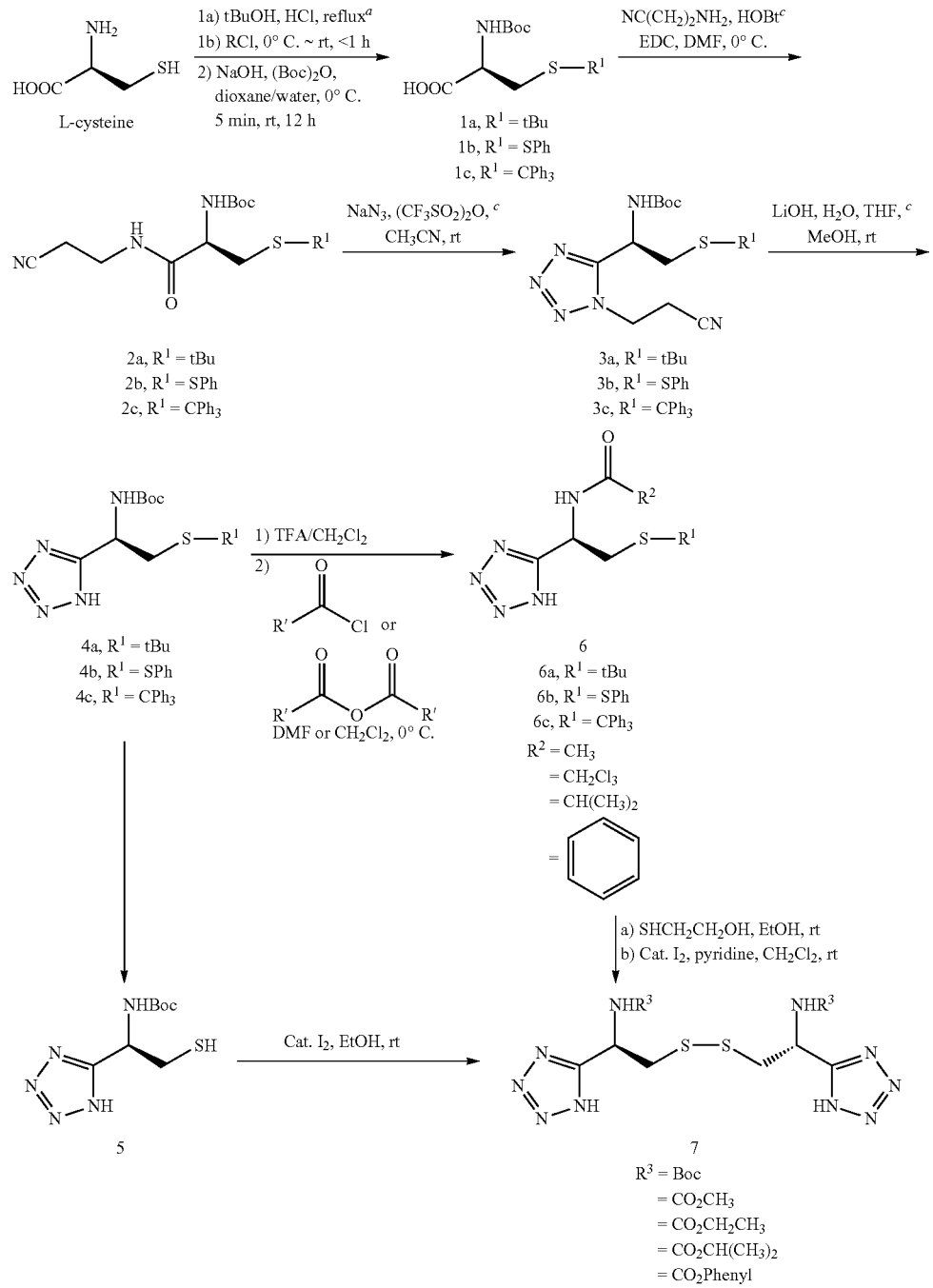

a) Pastuszak, J. J.; Chimiak, A.: tert-Butyl Group as Thiol Protection in Peptide Synthesis. *J. Org. Chem.* 46, 1868-1873 (1981) c) Biot, C.; Bauer, H.; Schirmer, R. H.; 5-Substituted Tetrazoles as Bioisosteres of Carboxylic Acids. Bioisosterism and Mechanistic Studies on Glutathione Reductase Inhibitors as Antimalarials. *J. Med. Chem.*, 47, 5972-5983 (2004)

In Scheme 1 (carboxylic acid bioisosteres) the desired tetrazole intermediate 3 is formed following the intermolecular cyclization of 2 with sodium azide. Subsequently, the preferred tetrazole bioisosteres 4 will be obtained after a dealkylation of compound 3. Once the bioisostere is formed, other functional groups are either protected or modified as shown in the remainder of Scheme 1 and continued in Scheme 2, shown below.

Synthesis of Carboxylic Acid Bioisosteres Continued

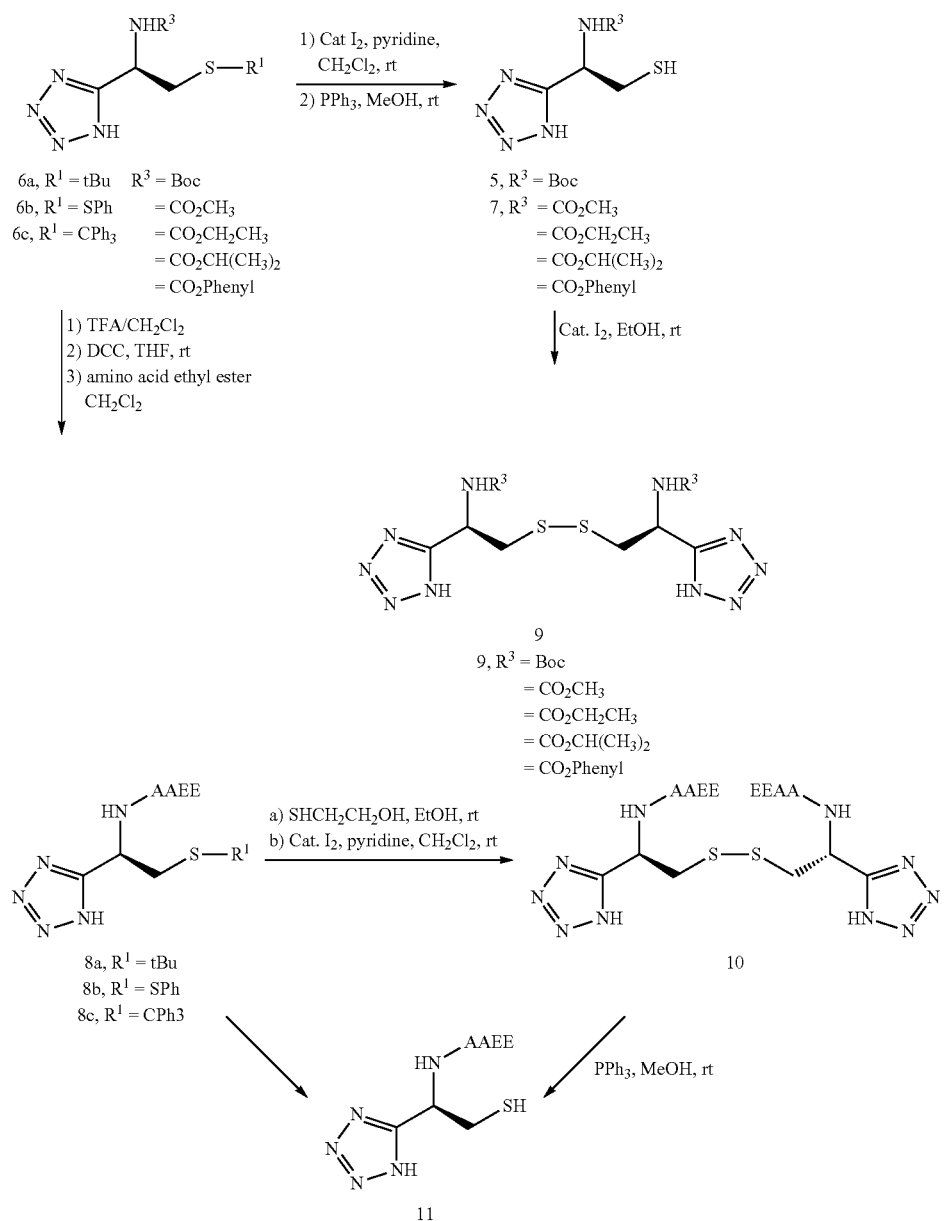

AAEE = amino acid ethyl ester
a) Pastuszak, J. J.: Chimiak, A.: tert-Butyl Group as Thiol Protection in Peptide Synthesis. *J. Org. Chem.* 46, 1868-1873 (1981) c) Biot, C.; Bauer, H,; Schirmer, R. H.; 5-Substituted Tetrazoles as Bioisosteres of Carboxylic Acids. Bioisosterism and Mechanistic Studies on Glutathione Reductase Inhibitors as Antimalarials. *J. Med. Chem.*, 47, 5972-5983 (2004)

In Scheme 3 the 1,2,4-oxadiazole bioisosteres and 1,2,4-thiodiazole bioisosteres 12 can be directly synthesized from the corresponding protected amino acid using the provided reagents/conditions. The 1,3,4-oxadiazole bioisosteres, 15, and the 1,2,4-triazole bioisosteres, 14, can be synthesized through a hydrazine intermediate, 13.

Synthesis of Amide Bioisosteres

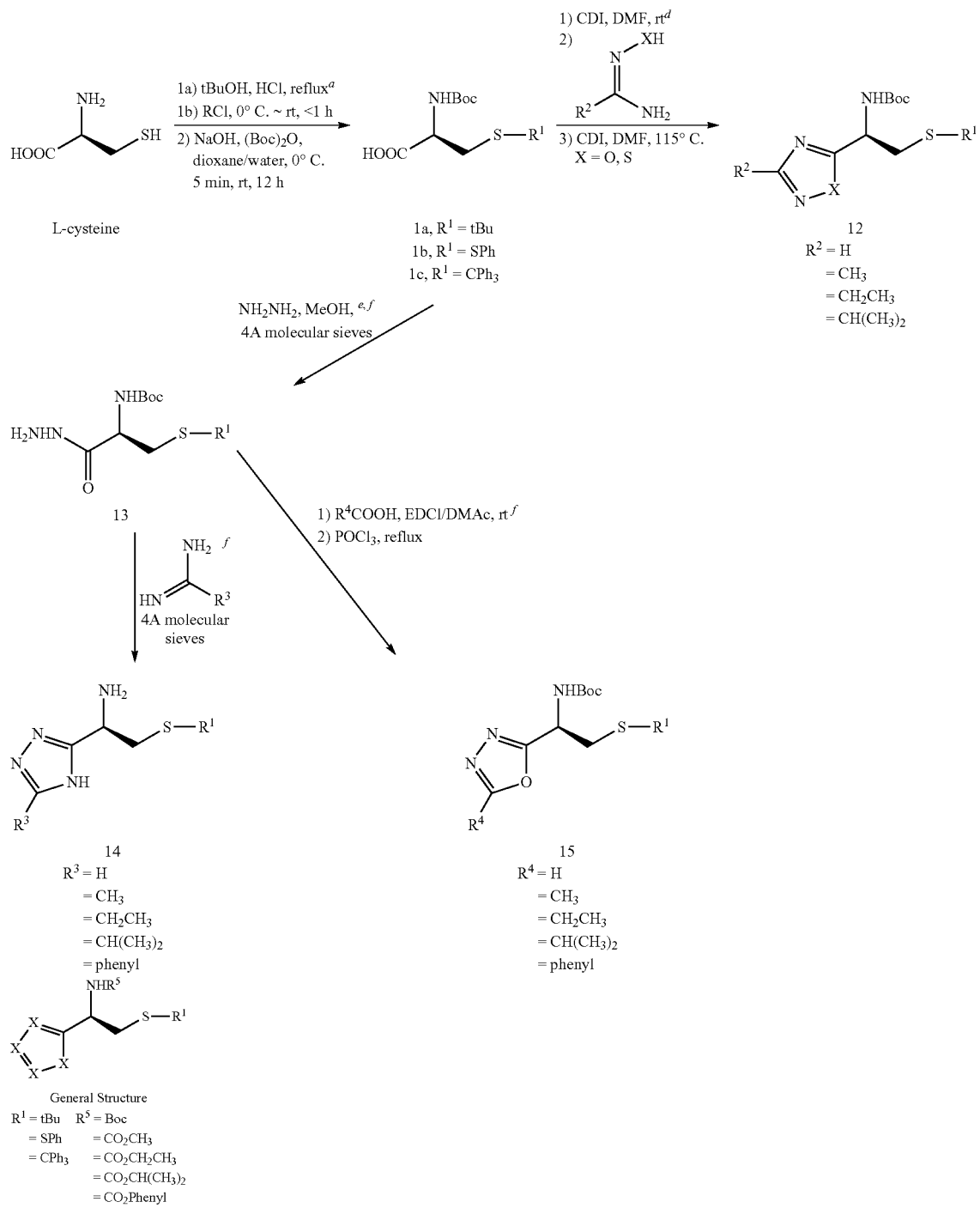

a) Pastuszak, J. J.: Chimiak, A.: tert-Butyl Group as Thiol Protection in Peptide Synthesis. *J. Org. Chem.* 46, 1868-1873 (1981) d) Deegean, T. L.; Nitz, T. J.; Cebzanov, D.; Pufko, D. E.; Parallel Synthesis of 1,2,4-oxadiazoles using CDI activation. *Bioorg Med Chem Lett.*, 9, 209-212 (1999) e) Kim, J. H.; Park, J. H.; Lee, H.; Highly Efficient Novel Poly(p-phenylenvinylene) Derivative with 1,3,4-oxadiazole Pendant on a Vinylene Unit. *Chem Mater.*, 15, 3414-3416 (2003) f) Katritzky, A.; Qi, M.; Feng, D.; Zhang, G.; Griffith, M.; Watson, K.; Synthesis of 1,2,4-triazole-Functionalized Solid Support and Its Use in the Solid-Phase Synthesis of Trisubstituted 1,2,4-triazoles, *Organic Letters.*, 1189-1191 (1999)

After each bioisostere is synthesized, the resulting compounds may be tested with the alkylated thiol group or reacted with the appropriate reagents to remove the thiol protecting group, as shown in Scheme 4. These compounds can be used for testing or further reacted to form self-dimers or free thiols as previously describe above.

Synthesis of Amide Bioisosteres Continued
Scheme 4
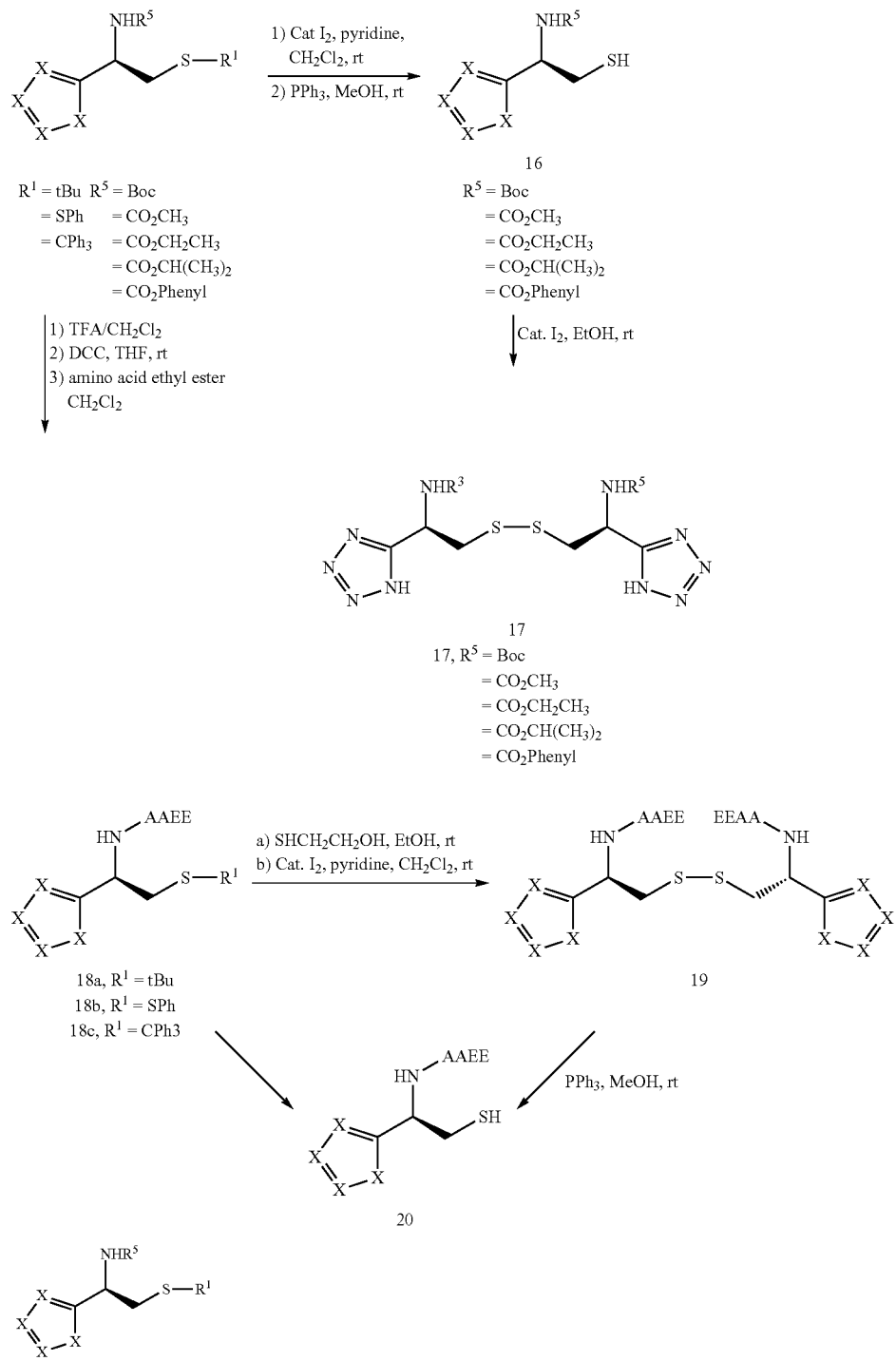
AAEE = amino acid ethyl ester
a) Pastuszak, J. J.; Chimiak, A.: tert-Butyl Group as Thiol Protection in Peptide Synthesis. *J. Org. Chem.* 46, 1868-1873 (1981)

The present method of synthesizing prodrugs according to the invention has many advantages over previous routes including, but not limited to: a) same synthetic route leads to both monomers and dimers (cysteine and cystine bioisosteres); b) protection of functional groups prevents side reactions (e.g., cyclization); c) the initial monomer synthesis eliminates problems associated with multiple functional groups; d) the occurrence of undesired intramolecular and intermolecular side reactions is decreased; e) and the described route can be easily expanded to incorporate minor chemical modifications.

Particularly preferred cysteine and cystine bioisosteres according to the invention are shown in FIGS. 1-4. These compounds are preferred either for advantages in partition coefficients, active transport, or breakdown products.

All cysteine prodrugs and bioisosteres as proposed in this application and previous applications as filed by the inventors can be coupled via outlined chemistry above to form cystine analogs are claimed in this application. These cystine analogs will be synthesized to create new hetero-dimers of cystine to improve bioavailability, partition coefficient, hinder metabolism, and increase both active and passive transport across the blood brain barrier and/or other members as determined by the inventors and biological data. Accordingly, the present compounds may be provided in the form of a symmetric cystine dimer formed by disulfide linkage of two identical compounds, an unsymmetric cystine dimer formed by disulfide linkage of two different compounds, or, of course, a salt, solvate or hydrate of a compound or symmetric or unsymmetric cystine dimer thereof. In certain unsymmetric dimers, a cysteine bioisostere according to the invention is linked by a disulfide bond to a cysteine prodrug or protected cysteine analog as described, for example, in U.S. patent application Ser. No. 12/367,867, filed Feb. 9, 2009, incorporated herein by reference in its entirety.

In certain embodiments, the inventive compounds will be provided as pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts, alkaline earth metal salts, e.g. calcium or magnesium salts; and salts formed with suitable organic ligands, e.g. quaternary ammonium salts.

Where the compounds according to the invention have at least one asymmetric center, they may accordingly exist as enantiomers. Where the compounds according to the invention possess two or more asymmetric centers, they may additionally exist as diastereoisomers. It is to be understood that all such isomers and mixtures thereof in any proportion are encompassed within the scope of the present invention.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. It is also envisioned that the compounds of the present invention may be incorporated into transdermal patches designed to deliver the appropriate amount of the drug in a continuous fashion.

For preparing solid compositions such as tablets, the principal active ingredient is mixed with a pharmaceutically acceptable carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. This solid pre-formulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50 or 100 mg, of the active ingredient. The tablets or pills of the novel composition can be coated or otherwise compounded to provide a dosage affording the advantage of prolonged action. For example, the tablet or pill can comprise an inner dosage and an outer dosage component, the latter being in the form of an envelope over the former. The two components can be separated by an enteric layer which, serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

The compounds according to the present invention exhibit schizophrenia reducing/alleviating activity, as can be demonstrated by standard protocols. For example, efficacy of the present inventive compounds in the schizophrenia context can be demonstrated by assaying startle response to a load stimulus (pulse) when preceded by a pre-pulse stimulus. Accordingly, another aspect of the invention provides a method for the reduction of schizophrenia in a subject in need of such treatment by administration of an effective amount of compound according to the invention or a precursor thereof. In the treatment of schizophrenia, suitable dosage level (i.e, an effective amount) is about (1-5000) mg/kg, per day, preferably about (30-3000) mg/kg per day, and especially about (50-1000) mg/kg per day. The compounds may be administered on a regimen of 1 to 4 times per day, or on a continuous basis.

As well, the compounds according to the present invention may also exhibit the ability to reduce drug cravings. This desirable activity can be shown in animal models involving drug-seeking behavior produced by stress, drug-paired cues, or a cocaine priming injection. Accordingly, yet another aspect of the invention is directed to a method of reducing a drug craving in a subject in need thereof. Such a method includes the step of administering an effective amount of a compound having the chemical structure of compound according to the invention, or a precursor thereof, to the subject whereby the drug craving is reduced in the subject. In the treatment of drug cravings, suitable dosage level (i.e., effective amount) is about (1-5000) mg/kg, per day, preferably about (30-3000) mg/kg per day, and especially about (50-1000) mg/kg per day.

The following Examples are offered by way of illustration and not by way of limitation. Indeed, various modifications of the invention in addition to those shown and described herein will become apparent to those skilled in the art from the foregoing description and the following examples and fall within the scope of the appended claims.

EXAMPLES

Example 1

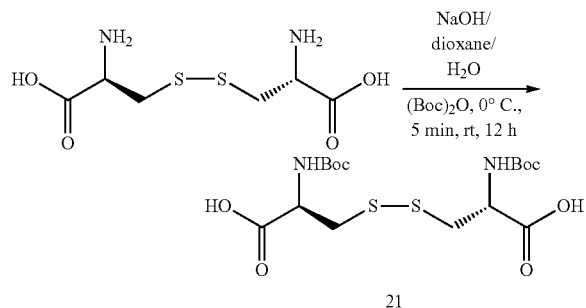

N,N'-Bis(tert-butoxy)carbonylcysteine (21)

To a solution of commercial L-cysteine (15 g, 0.06 mol) in aq NaOH (1M; 125 mL), a solution of di-tert-butyldicarbonate (41 g, 0.187 mol, 3 equiv) in dioxane (60 mL) was added at 0° C. The reaction mixture was stirred at 0° C. for 5 min, then at rt overnight. Half the volume of dioxane was evaporated under reduced pressure and the mixture was extracted with ethyl acetate (3×50 mL). The combined aqueous phases were acidified (pH 1) with aq HCl (1M) and extracted with ethyl acetate (3×50 mL). The combined organic layers were washed with brine, dried ($Na_2SO_4$), filtered and concentrated under reduced pressure to afford protected cystine in 65% yield as white solid. 21: m.p. 148~151° C. $^1$H NMR (DMSO-d6): δ 1.46 (s, 9H), 2.84-2.92 (m, 1H), 3.07-3.13 (m, 1H), 7.19 (d, 1H, J=9 Hz), 12.8 (s, 1H); $^{13}$C NMR (75.5 MHz, DMSO-d6): δ 28.5, 53.0, 54.1, 78.6, 85.9, 155.7, 172.8. This material was employed directly in the next step.

Example 2

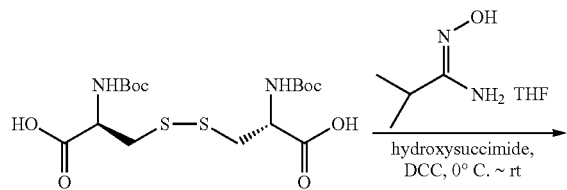

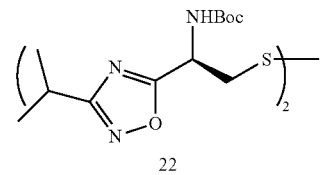

tert-Butyl (1R,1'R)-2,2'-disulfanediylbis(1-(3-isopropyl-1,2,4-oxadiazol-5-yl)ethane-2,1-diyl)dicarbamate (22)

To a solution of Boc-L-cystine, 21, (1.8 g, 4 mmol), isobutyl-rimidoxine (875 mg, 8.58 mmol), hydroxysuccimide (987 mg, 8.58 mmol) in THF (20 mL) was added at 0° C. over 15 min a solution of DCC (1.78 g, 8.64 mmol) in THF (10 mL). The mixture was stirred for 16 h while the temperature was allowed to warm to 20° C. The mixture was cooled to 0° C. and the precipitate which formed was removed by filtration. The filtrate was concentrated under vacuum and then dissolved into ethyl acetate (50 mL). The small amount of precipitate formed and was filtered out. The organic layer was washed with diluted sodium bicarbonate, brine, dried ($Na_2SO_4$) and removed under reduced pressure to give Boc-L-cystine bis(acetamidoxime) ester as white crystals. This material was taken up in toluene (100 mL) and the mixture was heated at reflux for 3 h, the water formed being removed by a Dean-Stark trap. The solvent was removed under vacuum and the residue was purified by flash chromatography (hexane/EtOAc=9:1) to form the white crystals in 73% yield as white solid. 22: m.p. 130~131° C. $^1$H NMR (300 MHz, CDCl3): δ 1.33 (d, 6H, J=4.5 Hz), 1.46 (s, 9H), 3.03-3.13 (m, 1H), 3.25 (d, 2H, J=3 Hz), 5.32 (s, br, 1H), 5.51 (s, br, 1H); $^{13}$C NMR (75.5 MHz, CDCl3): δ 20.2, 26.6, 28.2, 42.1, 47.8, 80.8, 154.6, 175.0, 176.8.

Example 3

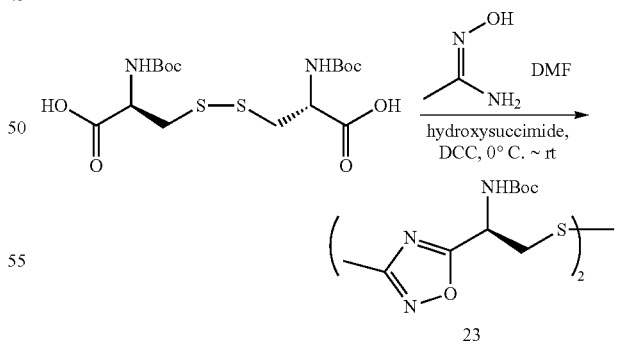

tert-Butyl (1R,1'R)-2,2'-disulfanediylbis(1-(3-methyl-1,2,4-oxadiazol-5-yl)ethane-2,1-diyl)dicarbamate (23) was prepared in 50% yield following the above procedure for 22, except the solvent was replaced with DMF to dissolve acetamidoxine. 23: m.p. 138~140° C. $^1$H NMR (500 MHz, CDCl3): δ 1.40 (s, 9H), 2.35 (s, 3H), 3.23 (s, 2H), 5.27 (s, 1H), 5.82 (s, 1H); $^{13}$C NMR (500 MHz, CDCl3): δ 11.8, 28.5, 42.2, 48.0, 81.0, 155.2, 167.6, 176.7. HRMS m/z $C_{24}H_{40}N_6O_6S_2(M+H)^+$ calcd 517.1903, found 517.1912.

Example 4

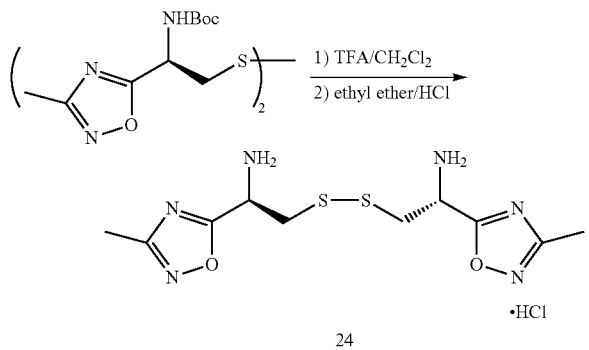

(1R,1'R)-2,2'-Disulfanediylbis(1-(3-methyl-1,2,4-oxadiazol-5-yl)ethanamine) (24)

To a solution of 23 (120 mg, 0.23 mmol) in DCM (5 mL), cooled to 0° C., was slowly added TFA (5 mL). The solution was gradually warmed up to rt and stirred for 2 h until TLC checked the starting material was disappeared. The solvent was removed under the reduced pressure, and the residue was dissolved into ethyl acetate (20 mL), washed with saturated sodium bicarbonate solution, brine and dried ($Na_2SO_4$). The solvent was removed and ethyl ether (2 ml) was added into the formed oil. Ethyl ether saturated with HCl gas was added at 0° C. until the white solid precipitated out. The solid was then collected by filtration and yield hydrochloride salt of 24 in 92% yield. 24: $^1$H NMR (300 MHz, CDCl3): δ 2.40 (s, 3H), 3.07-3.16 (m, 1H), 3.26-3.34 (m, 1H), 4.55-4.59 (m, 1H); $^{13}$C NMR (75.5 MHz, CDCl3): δ 11.3, 43.9, 48.0, 167.1, 179.3. HRMS m/z $C_{10}H_{16}N_6O_2S_2(M+H)^+$ calcd 317.0854, found 317.0850.

Example 5

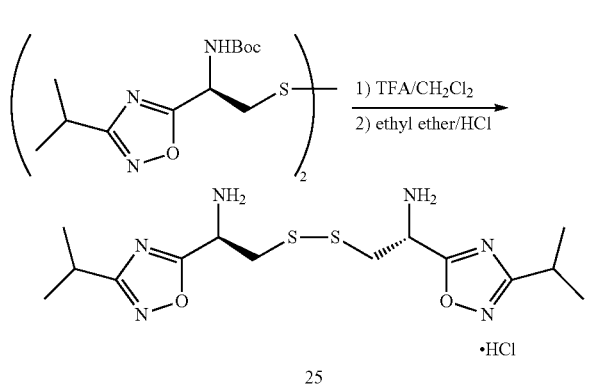

(1R,1'R)-2,2'-Disulfanediylbis(1-(3-isopropyl-1,2,4-oxadiazol-5-yl)ethanamine) (25): was prepared in 89% yield following the procedure for preparation of 24. 25: $^1$H NMR (300 MHz, CDCl3): δ 1.34 (d, 6H, J=3 Hz), 2.8 (br, 2H), 3.08-3.15 (m, 1H), 3.26-3.34 (m, 2H), 4.70 (br, 1H); $^{13}$C NMR (75.5 MHz, CDCl3): δ 20.3, 28.0, 44.1, 48.2, 170.5, 179.6.

Example 6

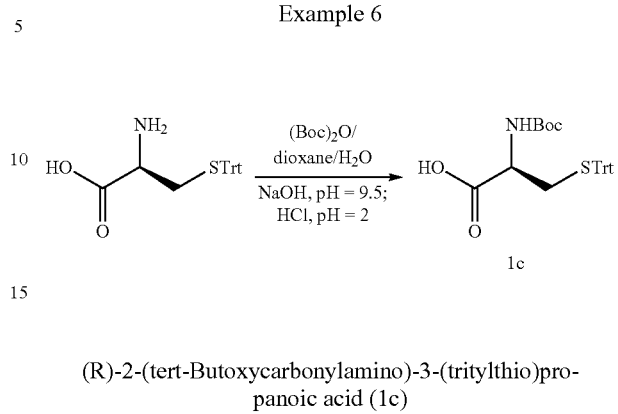

(R)-2-(tert-Butoxycarbonylamino)-3-(tritylthio)propanoic acid (1c)

To the solution of Trt-Cys-OH (22.68 g, 62.5 mmol) in dioxane (60 mL) and water (125 mL) was added di-tert-butyldicarbonate (41 g, 187 mmol) at 45° C., and the solution was adjusted with NaOH(4M) until pH=9.5, and then stirred at the same temperature overnight. Once the reaction was done, water and dioxane was removed under reduced pressure. The residue was dissolved into water (150 mL), extracted with ethyl acetate (2×100 mL). The aqueous layer was adjusted to pH=2 with dilute HCl while in an ice bath, and then the aqueous layer was extracted with ethyl acetate. The combined ethyl acetate layers were washed with water, dried over magnesium sulfate. Removal of the solvent under vacuum yielded a yellow oil. The residue was then dissolved into ethyl ether and carefully added a 1:1 mixture of ethyl ether and hexane while stirring to precipitate out the white solid in 60% yield. 1c: $^1$H NMR (300 MHz, CDCl3): δ 1.46 (s, 9H), 2.69 (br, 2H), 4.21 (s, 1H), 4.97 (s, 1H), 7.20-7.44 (m, 15H), 10.2 (br, 1H); $^{13}$C NMR (75.5 MHz, CDCl3): δ 28.1, 33.5, 52.4, 144.1, 155.4, 175.1.

Example 7

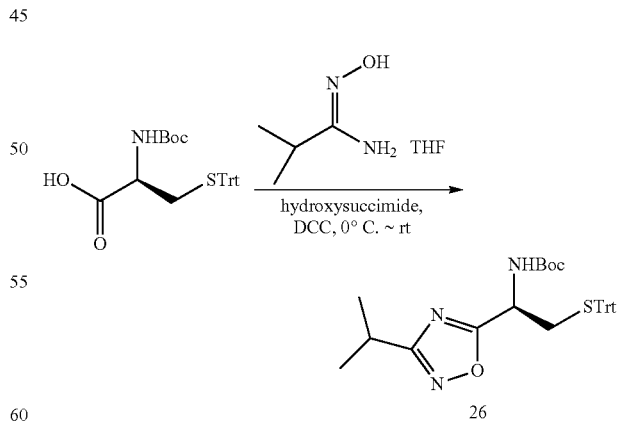

(R)-tert-Butyl 1-(3-isopropyl-1,2,4-oxadiazol-5-yl)-2-(tritylthio)ethylcarbamate (26) was prepared in 45% yield following the procedure for preparation of 22. 26: $^1$H NMR (300 MHz, CDCl3): δ 1.15 (d, 6H, J=3 Hz), 1.44 (s, 9H), 2.67 (br, 1H), 3.03-3.07 (m, 1H), 4.18 (s, 1H), 5.03 (s, 1H), 7.23-

7.46 (m, 15H), 8.76 (s, 1H); $^{13}$C NMR (75.5 MHz, CDCl3): δ 19.6, 27.6, 28.1, 54.3, 67.1, 80.6, 126.7, 128.4, 129.4, 144.4, 155.3, 170.3, 177.6.

Example 8

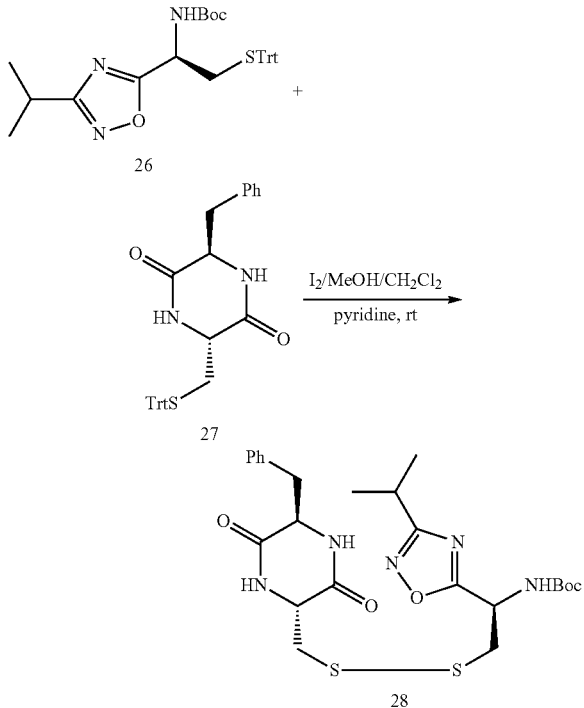

tert-Butyl(R)-2-((((2R,5R)-5-benzyl-3,6-dioxopiperazin-2-yl)methyl)disulfanyl)-1-(3-isopropyl-1,2,4-oxadiazol-5-yl)ethylcarbamate (28)

The trityl protected diketopiperazine 27 (315 mg, 0.64 mmol) and bioisostere 26 (340 mg, 0.64 mmol) were dissolved in a solution of methylene chloride (5 mL) and methanol (10 mL) with stirring. Pyridine (0.4 mL, 5.12 mmol) was then added to the resulting mixture, followed by a solution of iodine (357 mg, 1.4 mmol) in methanol (3 mL). The mixture was allowed to stir for 1 h at room temperature and TLC analysis indicated that the reaction was proceeding slowly by the appearance of a new spot under the starting material (UV light). After stirring for 2 h, the mixture was concentrated to a volume of 2 mL and methanol (5 mL) was added to result in a total volume of 10 mL. The solution was stirred an additional 23 h, and then washed with saturated sodium thiosulfate and the solvent was removed under the reduced pressure. The resulted residue was dissolved into ethyl acetate (5~10 mL) and the precipitate which resulted was collected by filtration to yield the product as white solid. 28: m.p.>217° C. (decomp). $^1$H NMR (300 NMR, DMSO-d$_6$) δ 1.04 (d, 6H, J=3 Hz), 1.38 (s, 9H), 2.68-3.15 (m, 6H), 4.21 (s, 1H), 4.44-4.47 (m, 1H), 7.13-7.26 (m, 5H), 8.13 (s, 1H), 8.35 (s, 1H), 10.7 (s, 1H); $^{13}$C NMR (75.5 NMR, DMSO-d6) δ 19.0, 28.5, 38.8, 43.2, 53.2, 55.1, 55.8, 78.8, 127.1, 128.5, 130.6, 136.4, 155.7, 166.0, 166.5, 171.8, 177.5.

Example 9

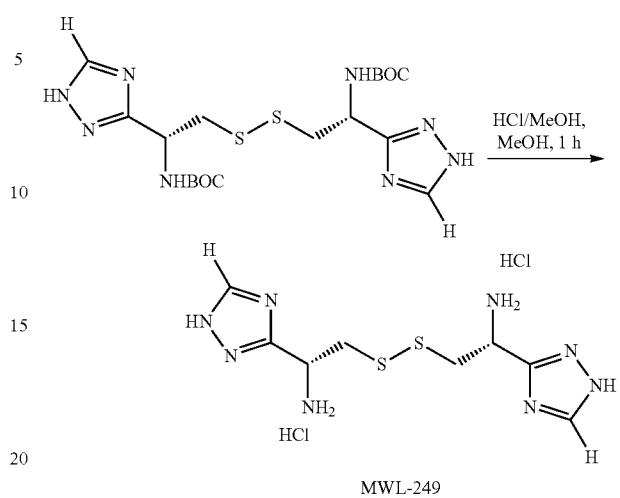

MWL-249

The dimer (140 mg, 0.29 mmol) was dissolved in MeOH (5 mL) and a saturated solution of anhydrous HCl in MeOH (5 mL) was added. The mixture which resulted was stirred for 1 h, after which the organic solvent was removed under reduced pressure. The oily residue which formed was dissolved in water (15 mL) and washed with DCM (3×10 mL) to remove organic impurities. The water was then removed under reduced pressure and the oily residue which remained was dried under vacuum for 24 h to obtain the solid hydrochloride salt MWL-249 (99% yield).

R$_f$ baseline (DCM/MeOH 5:1); $^1$H NMR (300 MHz, D$_2$O) δ 8.66 (s, 1H), 4.88-4.93 (m, 1H), 3.32 (d, J=5.5 Hz, 2H); $^{13}$C NMR (75 MHz, CDCl$_3$) δ 156.0, 147.2, 47.3, 38.3 ppm. HRMS (ESI, M-HCl, —Cl, C$_8$H$_{15}$N$_8$S$_2$) calc.: 287.0861, found: 287.0851.

Example 10

General Procedures for BOC Deprotection and Formation of the HCl Salt of Dimers

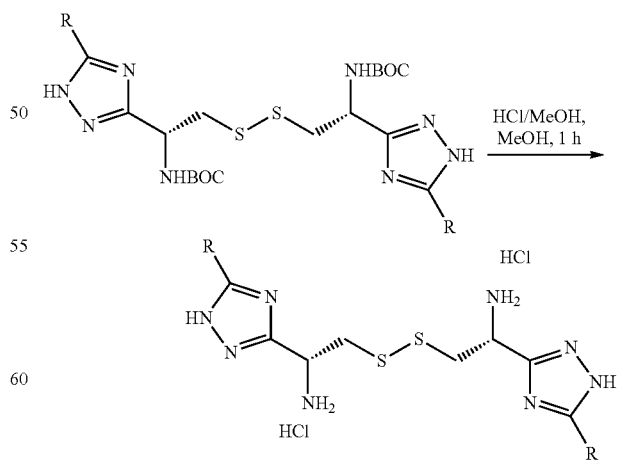

MWL-224: R=Me

1H NMR (300 MHz, D$_2$O) δ 4.99 (t, J=6.7 Hz, 1H), 3.35 (dd, J=15.1, 6.5 Hz, 1H), 3.28 (dd, J=15.0, 7.0 Hz, 1H), 2.53

(s, 3H) ppm; 13C NMR (75 MHz, D$_2$O) 154.3, 152.2, 46.3, 37.7, 9.8 ppm. HRMS (ESI, M$^+$, C$_{10}$H$_{20}$N$_8$S$_2$) calc.: 315.1169, found: 315.1174.

MWL-235: R=Et

1H NMR (300 MHz, D$_2$O) δ 4.95 (t, J=6.5 Hz, 1H), 3.31 (dd, J=14.9, 6.3 Hz, 1H), 3.24 (dd, J=14.8, 6.8 Hz, 1H), 2.86 (q, J=7.6 Hz, 2H), 1.17 (t, J=7.7 Hz, 3H) ppm; 13C NMR (75 MHz, D$_2$O) δ 158.8, 151.9, 46.3, 37.7, 18.1, 10.0 ppm. HRMS (ESI, M+H$^+$, C$_{12}$H$_{23}$N$_8$S$_2$) calc.: 343.1482, found: 343.1487.

MWL-236: R=i-Pr

1H NMR (300 MHz, D$_2$O) δ 4.98 (t, J=6.5 Hz, 1H), 3.22-3.40 (m, 3H), 1.27 (t, J=7.1 Hz, 6H) ppm; 13C NMR (75 MHz, D$_2$O) δ 162.5, 152.7, 46.6, 37.8, 25.7, 19.4 ppm. HRMS (ESI, M+H$^+$, C$_{14}$H$_{27}$N$_8$S$_2$) calc.: 371.1800, found: 371.1805.

Example 11

General Procedure for Cleaving Disulfide Bonds

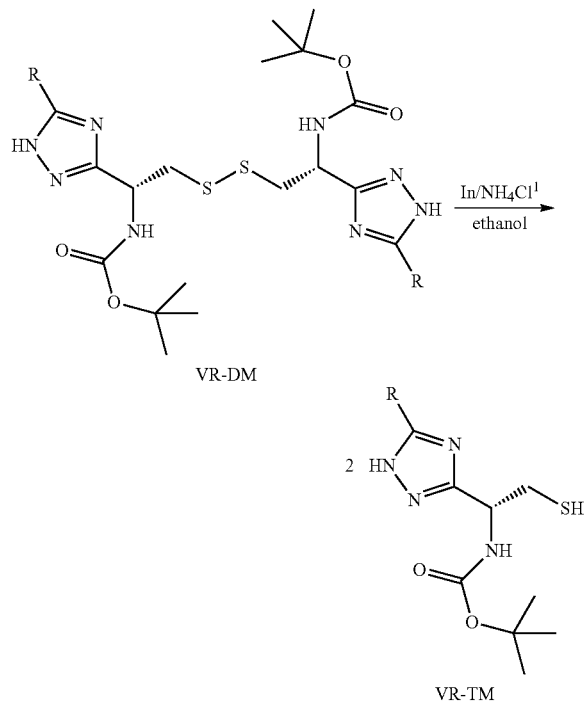

VR-DM

VR-TM

The disulfide (VR-DM), (1 mmol) was dissolved in 10 mL of ethanol and indium (1.1 mmol) was added in one portion while stirring. Then anhydrous NH$_4$Cl (2.2 mmol) of was added to the suspension while stirring. The mixture was heated to reflux under argon for 4-6 hrs. After full conversion of the starting material was achieved the solids were removed by filtration over a bed of celite. The solvent was removed under reduced pressure until dryness. The residue was washed well with water to dissolve the inorganic salts. The mixture was filtered and dried to yield the product. The monomer can be purified by crystallization from dichloromethane (DCM) or ethanol. Yield 85-90%.

R=Me [VR-TM-me]

1H NMR (300 MHz, CDCl$_3$) δ 6.44 (d, 1H), 5.30 (s, 1H), 3.37-3.78 (m, 2H), 2.93 (s, 3H), 1.48 (s, 9H); 13C NMR (75 MHz, CDCl$_3$) δ 158.2, 155.8, 128.1, 127.8, 127.5, 81.0, 45.2, 28.3, 13.3 ppm. HRMS (ESI, M$^+$+H, C$_{10}$H$_{19}$N$_4$O$_2$S) calc.: 259.1229, found: 259.1237 and (M$^+$+Na, C$_{10}$H$_{18}$N$_4$O$_2$SNa) calc.: 281.1048, found 281.1056.

R=Et [VR-TM-et]

1H NMR (300 MHz, CDCl$_3$) δ 6.21 (d, 1H), 5.09 (s, 1H), 2.94-3.54 (m, 2H), 2.79-2.87 (q, J=7.5, 2H), 1.45 (s, 9H), 1.27-1.34 (t, J=7.5, 3H). HRMS (ESI, M$^+$+H, C$_{11}$H$_{21}$N$_4$O$_2$S) calc.: 273.1385, found: 273.1392.

R=Ph [VR-TM-ph]

1H NMR (300 MHz, CDCl$_3$) δ 7.94-8.01 (d, 2H), 7.46 (s, 3H), 6.23 (s, 1H), 5.13 (s, 1H), 2.95-3.64 (m, 2H), 1.48 (s, 9H); HRMS (ESI, M$^+$+H, C$_{15}$H$_{21}$N$_4$O$_2$S) calc.: 321.1385, found: 321.1391.

R=i-Pr [VR-TN-ipr]

1H NMR (300 MHz, CDCl$_3$) δ 6.44 (d, 1H), 5.16 (s, 1H), 2.81-3.66 (m, 3H), 1.48 (s, 9H), 1.37 (s, 6H); 13C NMR (75 MHz, CDCl$_3$) δ 159.3, 155.8, 142.1, 133.7, 81.1, 57.2, 39.8, 28.3, 21.5 ppm. HRMS (ESI, M$^+$+H, C$_{12}$H$_{23}$N$_4$O$_2$S) calc.: 287.1542, found: 287.1547 and (M$^+$+Na, C$_{12}$H$_{22}$N$_4$O$_2$SNa) calc.: 309.1361, found 309.1354.

Example 12

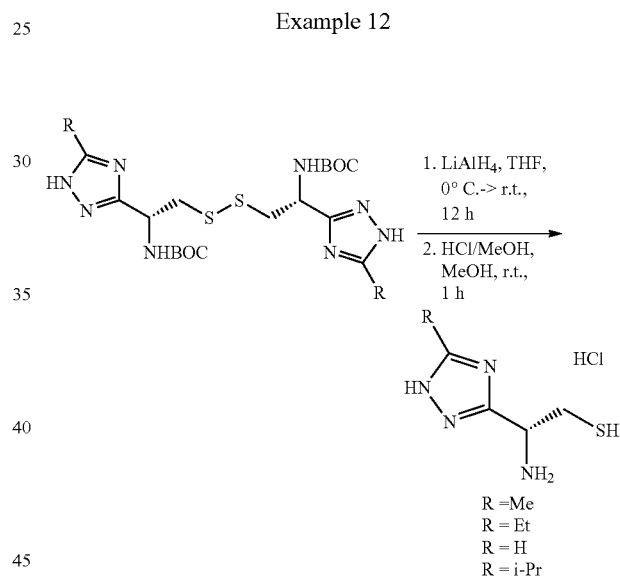

R = Me
R = Et
R = H
R = i-Pr

The LiAlH$_4$ (3 eq.) and THF were combined under argon and the suspension was cooled to 0° C. The BOC protected dimer (1 eq.) was added as a solid to the solution and the evolution of gas was observed. After 10 min. of stirring the mixture was warmed to r.t. and stirred for an additional 12 h. The reaction progress was stopped by the addition of MeOH and the organic solvents were removed under reduced pressure. The crude material (smells really bad) was directly purified by flash column chromatography on silica gel using DCM/MeOH as the eluent (gradient elution: begin with pure DCM, then 20:1, 10:1, to give the intermediate, R$_f$0.24 (DCM/MeOH 20:1)). This was used directly for the next step due to the formation of dimers on standing. The solution of the monomer (1 eq.) in MeOH (3 mL) was treated with anhydrous HCl in MeOH (3 mL). The mixture was stirred for 30 min. after which the solvent was removed under reduced pressure and the residue was dissolved again in water and washed with DCM (3×10 mL). The water was removed under reduced pressure and the product was obtained as a slightly yellowish salt. The compound dimerized within 24 h in solution and also dimerized when kept as a salt (probably due to solvent traces). Stored in benzene at −25° C.

Product R/baseline (DCM/MeOH 5:1); yields 35-55%.

MWL 273: R=Me

1H NMR (500 MHz, D$_2$O) δ 4.46 (tt, J=19.6, 5.7 Hz, 1H), 2.76-2.88 (m, 3H), 2.29 (t, J=19.5 Hz, 3H); 13C NMR (125 MHz, CDCl$_3$) δ 153.4, 151.9, 48.7, 24.9, 8.6 ppm.

MWL 283: R=Et

1H NMR (500 MHz, D$_2$O) δ 4.85 (t, J=6.1 Hz, 1H), 3.19 (dd, J=14.7, 6.4 Hz, 1H), 3.16, (dd, J=14.7, 6.1 Hz, 1H), 2.95 (q, J=7.7 Hz, 2H), 1.29 (t, J=7.6 Hz, 3H); 13C NMR (125 MHz, CDCl$_3$) δ 159.7, 153.6, 49.8, 25.0, 18.8, 10.6 ppm. HRMS (ESI, M-Cl$^+$, C$_4$H$_9$N$_4$S) calc.: 145.0548, found: 145.0542.

Example 13

Synthesis of Unsymmetrical Ligand with Triazole Functionality

General Procedure:

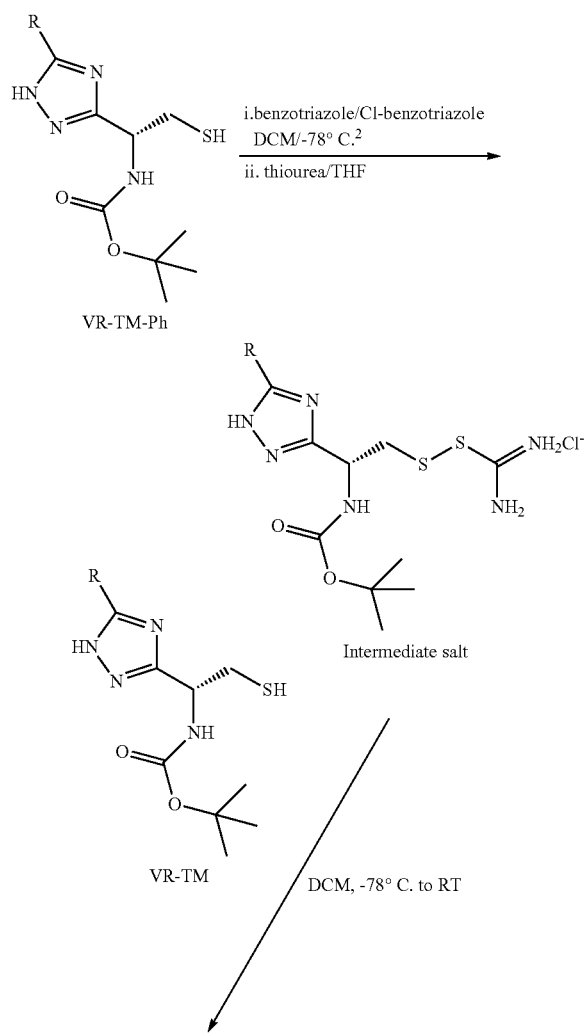

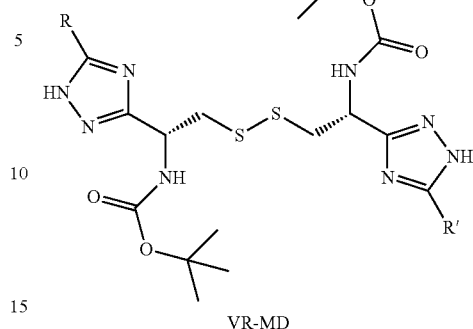

VR-MD

References:
1. G. Vidya Sagar Reddy, G. Venkat Rao and D. S. Iyengar, *Synth, Commun.*, 200,30,859-862.
Roger Hunter, Mino Caira and Nashia Stellenboom, *J. Org. Chem.*, 2006, 71(21) 8268-8271

A solution of triazole monomer (VR-TM) (R=Ph) (2 mmol) was added slowly under an inert atmosphere to a stirred solution of benzotriazole (2 mmol) and chloro-benzotriazole (4 mmol) in dichloromethane (DCM) (15 mL) at −78°. After 30 minutes a solution of thiourea (6 mmol) in anhydrous THF (5 mL) was added and stirring continued for 30 minutes. The other triazole monomer (R'≠Ph)(VR-TM) (2 mmol) in DCM was added while the temperature was maintained at −78° C. The solution was allowed to stir for 18-20 hr, while the mixture slowly warmed to room temperature. The solvent was removed under reduced pressure, and the residue was dissolved in DCM followed by washing with water (30 mL×3). The organic layer was dried (Na$_2$SO$_4$) and the solvent was then removed under reduced pressure and the unsymmetrical triazole ligand was purified by chromatography (yield 60-65%).

R=Ph, R'=Me (VR-MD-01)

1H NMR (300 MHz, CDCl$_3$) δ 8.33-8.51 (d, 2H), 7.34 (s, 3H), 5.30 (bs, 2H), 2.97-3.61 (m, 4H), 2.43 (s, 3H), 1.47 (s, 18H); HRMS (ESI, M$^+$+H, C$_{25}$H$_{37}$N$_8$O$_4$S$_2$) calc.: 577.2379, found: 577.2369 and (M$^+$+Na, C$_{25}$H$_{36}$N$_8$O$_4$S$_2$Na) calc.: 599.2199, found 599.2194.

Example 14

Deprotection of BOC Group/Formation of HCl Salt of Unsymmetrical Triazole Ligand Salts. A General Procedure

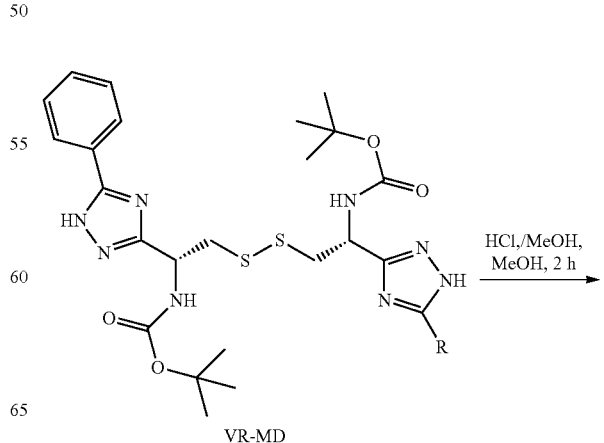

VR-MD

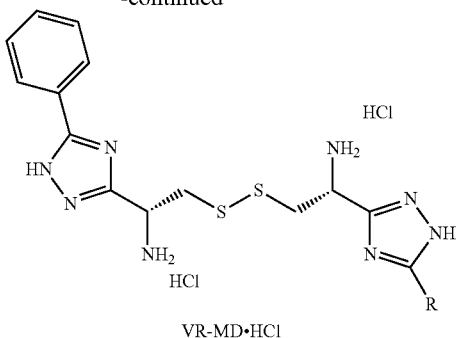

VR-MD·HCl

The unsymmetrical triazole ligand (VR-MD-01) (0.2 mmol) was dissolved in EtOH (5 mL) and a saturated solution of anhydrous HCl in EtOH (5 mL) was added. The mixture was stirred for 2 h, after which the solvent was removed under reduced pressure. The oily residue which formed was dissolved in distilled water (15 mL) and washed with DCM (3×10 mL) to remove organic impurities. The water was then removed under reduced pressure and the gummy residue was finally dried under high vacuum to obtain the solid hydrochloride salt (99% yield).

R=Ph, R'=Me (VR-MD-02)

1H NMR (300 MHz, CDCl$_3$) δ 7.74-7.76 (d, 2H), 7.47 (s, 3H), 4.88 (bs, 2H), 3.14-3.23 (m, 4H), 2.27 (s, 3H).

Example 15

General Procedure for Preparation of Aromatic Amides of Dimers

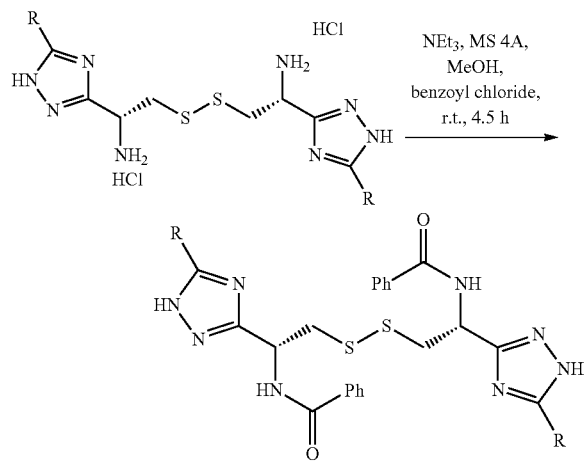

The hydrochloride salt (1 eq.) was dissolved in dry NEt$_3$ (3 mL) and molecular sieves (4 Å) and dry MeOH (a few drops only for complete solvation) were added under argon. Benzoyl chloride (2.2 eq.) was then added neat in one portion at r.t. and the solution was stirred for 4.5 h until complete conversion of the starting material was obtained. The EtOAc was then added and the mixture was washed with a sat. solution of aq. NaHSO$_4$ (3×), with a sat. solution of aq. NaHCO$_3$ (2×) and brine and dried (MgSO$_4$). The organic solvent was then removed under reduced pressure. The crude material was purified by flash column chromatography on silica gel using DCM/MeOH as the eluent (gradient elution: begin with pure DCM, then 30:1, 10:1). Yields 65-75%.

MWL-284: R=Et

Product R$_f$0.45 (DCM/MeOH 20:1; ran TLC twice); 1H NMR (500 MHz, MeOD) δ 8.74-8.77 (m, 1H), 7.83-7.87 (m, 2H), 7.48-7.53 (m, 1H), 7.39-7.45 (m, 2H), 5.62-5.67 (m, 1H), 3.42-3.50 (m, 1H), 3.28-3.34 (m, 1H), 2.77 (q, J=7.7 Hz, 2H), 1.30 (t, J=7.7 Hz, 3H); 13C NMR (125 MHz, MeOD) δ 170.0, 135.3, 132.8, 129.5, 128.6, 69.1, 61.5, 40.2, 31.6, 30.1, 24.9, 24.0, 11.5 ppm. HRMS (ESI, M+Na$^+$, C$_{26}$H$_{30}$N$_8$O$_2$S$_2$Na) calc.: 573.1825, found: 573.1831.

MWL299: R═H

Product R$_f$0.51 (DCM/MeOH 20:1; ran TLC twice); 1H NMR (500 MHz, CDCl$_3$) δ 7.97 (s, 1H), 7.68-7.84 (m, 2H), 7.47-7.48 (m, 1H), 7.36-7.39 (m, 3H), 5.16 (d, J=7.3 Hz, 1H), 3.06-3.11 (m, 1H), 2.85-2.89 (m, 1H); 13C NMR (125 MHz, CDCl$_3$) δ 167.6, 144.3, 143.3, 133.3, 132.0, 128.6, 127.2, 67.2, 53.4 ppm.

Example 16

General Procedure for the Preparation of Aliphatic Amides of Dimer

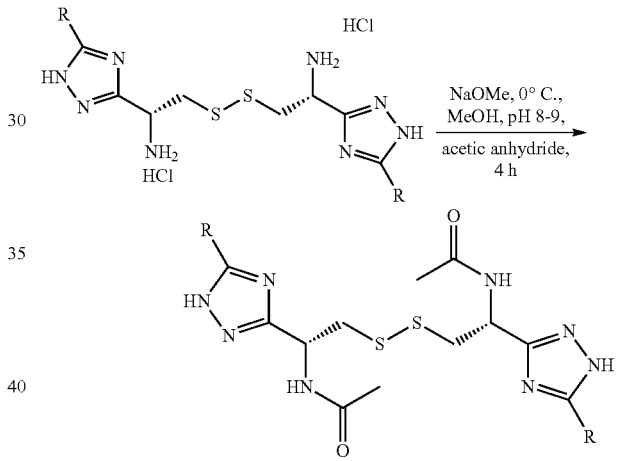

Sodium (40 eq.) was dissolved in dry MeOH (10 mL) under argon at 0° C. and added to a solution of the BOC protected dimer (1 eq.) in dry MeOH (10 mL) under argon at r.t. and the pH maintained at 8-9. The clear colorless solution which resulted was stirred for 10 min. and then cooled to 0° C. after which it was treated with dry acetic anhydride (3 eq.) added all in one portion. The reaction was complete after 4 h after which silica was added and the solvent was removed under reduced pressure. The crude material was directly purified by flash column chromatography on silica gel using DCM/MeOH as the eluent (start with pure DCM, then 10:1). Yields 60-70%.

MWL-258: R=Me

Product R$_f$0.7 (DCM/MeOH 5:1); 1H NMR (500 MHz, DMSO-d$_6$) δ 8.49-8.51 (m, 1H), 5.15-5.21 (m, 1H), 3.12-3.18 (m, 1H), 3.03-3.09 (m, 1H), 2.59-2.62 (m, 3H), 2.30 (s, 1H), 1.84 (s, 3H); 13C NMR (125 MHz, DMSO-d$_6$) δ 169.8, 169.0, 161.8, 156.8, 46.0, 22.5, 15.6 ppm. HRMS (ESI, M+Na$^+$, C$_{14}$H$_{22}$N$_8$O$_2$S$_2$Na) calc.: 421.1199, found: 421.1179.

MWL-309: R=Et

Product R$_f$0.65 (DCM/MeOH 5:1); 1H NMR (500 MHz, MeOD) δ 5.39-5.43 (m, 1H), 4.95 (bs, 1H), 3.29-3.35 (m, 1H), 3.16 (dddd, J=13.8, 8.1, 5.7 Hz, 1H), 2.80 (q, J=7.7 Hz, 2H), 2.03 (s, 2H), 1.32 (t, J=7.7 Hz, 3H); $^{13}$C NMR (75 MHz, CDCl$_3$) δ 169.6, 162.5, 161.1, 47.4, 42.8, 23.7, 22.7, 11.1 ppm. HRMS (ESI, M+H$^+$, C$_{16}$H$_{27}$N$_8$O$_2$S$_2$) calc.: 427.1698, found: 427.1681.

Example 17

Synthesis of Asymmetric Bis-Dipiperazinedione

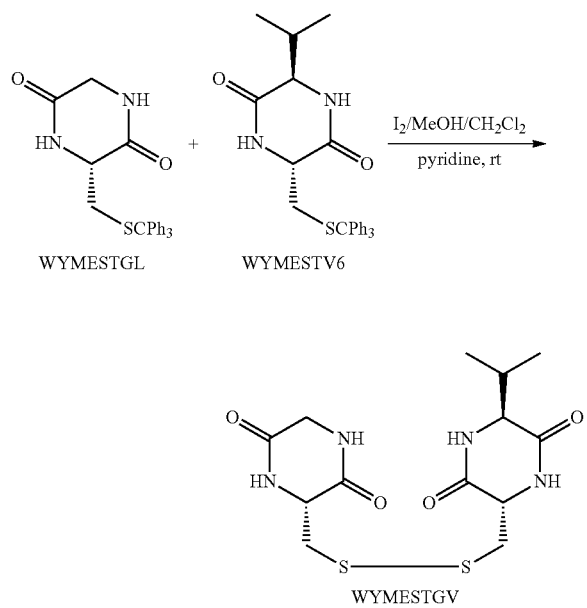

WYMESTGV:

The trityl protected diketo-piperazine WYMESTGL (201 mg, 0.5 mmol) and WYMESTV6 (222 mg, 0.5 mmol) were dissolved in a solution of methylene chloride (5 mL) and methanol (10 mL) with stirring. Pyridine (0.3 mL, 3.75 mmol) was then added to the resulting mixture, followed by a solution of iodine (126 mg, 0.5 mmol) in methanol (3 mL). The mixture was allowed to stir for 1 h at room temperature. No precipitate had formed by this time; however, analysis by TLC indicated that the reaction was proceeding slowly by the appearance of a new spot under the starting material (UV light). A precipitate began to form within 2 h after concentrating the solution to a volume of 2 mL and methanol (5 mL) was added bring the total volume to 10 mL. The solution was stirred an additional 6-8 h and the precipitate which formed was filtered off. The solid was washed with cold methanol. The precipitate was filtered, washed with hot methanol and dried to yield a dimer as a white solid (128 mg, 60%).

WYMESTGV:

$^1$H NMR (300 MHz, DMSO-d$_6$) δ 0.86 (d, J=6.6 Hz, 3H), 0.97 (d, J=6.9 Hz, 3H), 2.12-2.32 (m, 1H), 3.14-3.21 (m, 4H), 3.74-3.82 (m, 3H), 4.12 (s, 1H), 4.22 (s, 1H), 8.10 (s, 1H), 8.18 (s, 3H); $^{13}$C NMR (75.5 MHz, DMSO-d$_6$) δ 17.6, 19.0, 31.5, 43.0, 43.3, 43.6, 44.8, 54.1, 54.3, 54.4, 59.8, 166.2, 166.7, 166.8, 167.4.

Example 18

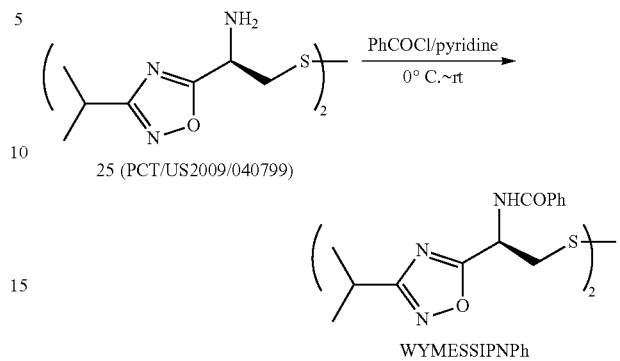

WYMESSIPNPh:

To a solution of free base 25 (reported in PCT/US2009/040799) (140 mg, 0.48 mmol) in pyridine (2 mL) which had been precooled to 0° C., benzoyl chloride (0.15 mL) was added. After being kept for 1 h at room temperature, the mixture was poured onto ice. The precipitate was collected by filtration and was recrystallized from methanol in 88% yield.

WYMESSIPNPh:

$^1$H NMR (300 MHz, CDCl$_3$): δ 1.25-1.40 (m, 6H), 3.14-3.17 (m, 1H), 3.43-3.49 (m, 1H), 3.52-3.57 (m, 1H), 5.87-5.90 (m, 1H), 7.28-7.33 (m, 1H), 7.48-7.61 (m, 4H), 7.90-7.93 (m, 2H); $^{13}$C NMR (75.5 MHz, CDCl$_3$): δ 20.8, 27.2, 42.4, 47.7, 127.8, 129.2, 129.4, 132.7, 167.6, 175.6, 176.8.

Example 19

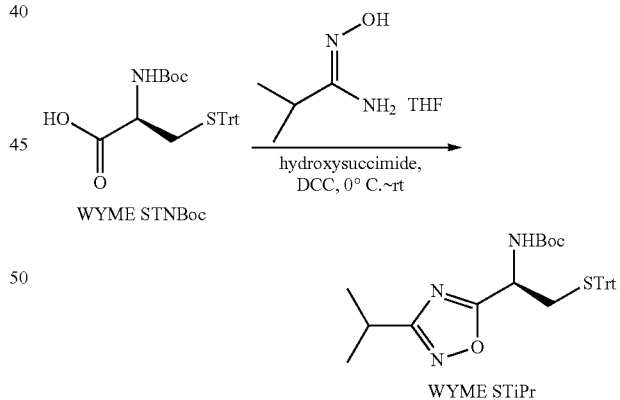

WYMESTiPr:

A solution of DCC (3.56 g, 17.28 mmol) in THF (20 mL) was added to a solution of trityl protected Boc-L-cysteine (WYMESTNBoc), (3.7 g, 8 mmol), isobutyl-rimidoxine (1.75 g, 17.16 mmol), hydroxysuccimide (19.7 g, 17.16 mmol) in THF (50 mL) was added at 0° C. over 15 min. The mixture was stirred for 16 h while the temperature was allowed to warm to room temperature. The mixture was cooled to 0° C. and the precipitate which formed was removed by filtration. The filtrate was concentrated under vacuum and then dissolved into ethyl acetate (50 mL). A small amount of precipitate formed and was filtered off. The organic layer was washed with diluted aq sodium bicarbonate solution, brine, dried ($Na_2SO_4$) and the solvent removed under reduced pressure to give trityl protected Boc-L-cysteine acetamidoxime ester as white crystals. This material was taken up in toluene (200 mL) and the mixture was heated at reflux for 3 h; the water which formed was removed via a Dean-Stark trap. The solvent was removed under vacuum and the residue was purified by flash chromatography (silicagel, hexane/EtOAc=9:1) to form the white crystals in 71% yield as a white solid.

WYMESTiPr:

$^1$H NMR (300 MHz, $CDCl_3$): δ 1.15 (d, J=3 Hz, 6H), 1.44 (s, 9H), 2.67 (br, 1H), 3.03-3.07 (m, 1H), 4.18 (s, 1H), 5.03 (s, 1H), 7.23-7.46 (m, 15H), 8.76 (s, 1H); $^{13}$C NMR (75.5 MHz, $CDCl_3$): δ 19.6, 27.6, 28.1, 54.3, 67.1, 80.6, 126.7, 128.4, 129.4, 144.4, 155.3, 170.3, 177.6.

Example 20

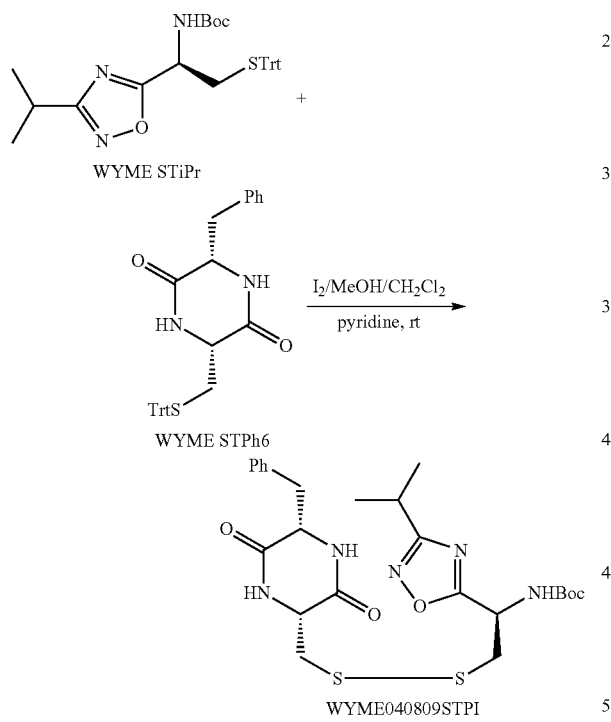

General Procedure for Preparation of Other Ligands with Diketopiperazine and Bioisosteres:

tert-Butyl(R)-2-((((2R,5R)-5-benzyl-3,6-dioxopiperazin-2-yl)methyl)disulfanyl)-1-(3-isopropyl-1,2,4-oxadiazol-5-yl)ethylcarbamate (WYME040809STPI): The trityl protected diketopiperazine (315 mg, 0.64 mmol) and bioisostere (340 mg, 0.64 mmol) were dissolved in a solution of dichloromethane (5 mL) and methanol (10 mL) with stirring. Pyridine (0.4 mL, 5.12 mmol) was then added to the resulting mixture, followed by a solution of iodine (357 mg, 1.4 mmol) in methanol (3 mL). The mixture was allowed to stir for 1 h at room temperature and TLC analysis indicated that the reaction was proceeding slowly by the appearance of a new spot under the starting material (UV light). After stirring for 2 h, the mixture was concentrated to a volume of 2 mL and methanol (5 mL) was added to result in a total volume of 10 mL. The solution was stirred an additional 23 h, and then washed with saturated sodium thiosulfate and the solvent was removed under the reduced pressure. The resulted residue was dissolved into ethyl acetate (5~10 mL) and the precipitate which resulted was collected by filtration to yield the product as white solid (or purified by prepared chromatograph after washed with low polar solvent).

$^1$H NMR (300 NMR, DMSO-$d_6$) δ 1.04 (d, 6H, J=3 Hz), 1.38 (s, 9H), 2.68-3.15 (m, 6H), 4.21 (s, 1H), 4.44-4.47 (m, 1H), 7.13-7.26 (m, 5H), 8.13 (s, 1H), 8.35 (s, 1H), 10.7 (s, 1H); $^{13}$C NMR (75.5 NMR, DMSO-$d_6$) δ 19.0, 28.5, 38.8, 43.2, 53.2, 55.1, 55.8, 78.8, 127.1, 128.5, 130.6, 136.4, 155.7, 166.0, 166.5, 171.8, 177.5. (NMR was reported in PCT/US2009/040799) HRMS (ESI, $M^+$+H, $C_{24}H_{33}N_5O_5S_2$) calc.: 536.2001, found: 536.2019.

Example 21

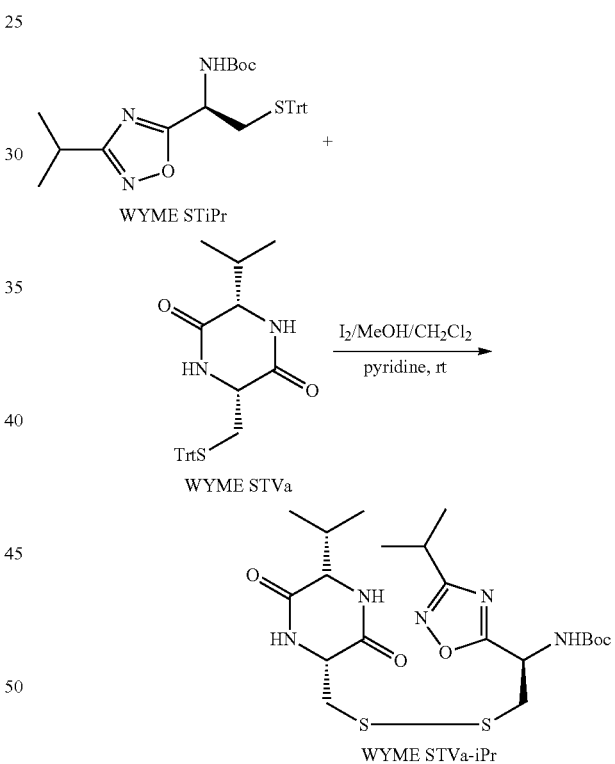

Tert-Butyl(R)-1-(3-isopropyl-1,2,4-oxadiazol-5-yl)-2-((((2R,5R)-5-isopropyl-3,6-dioxopipera-zin-2-yl)methyl)disulfanyl)ethylcarbamate (WYME STVa-iPr) was prepared following the procedure described above: $^1$H NMR (300 NMR, DMSO-$d_6$) δ 0.96 (d, 3H, J=6.6 Hz), 1.07 (d, 3H, J=7.2 Hz), 1.34 (s, 3H), 1.36 (s, 3H), 1.48 (s, 9H), 2.84-2.92 (m, 1H), 3.09-3.13 (m, 1H), 3.28-3.30 (m, 2H), 3.42-3.47 (dd, 1H), 4.37 (s, 1H), 5.38 (s, 1H), 5.59 (d, 1H, J=7.5 Hz), 6.58 (s, 1H), 6.82 (s, 0.33H), 6.96 (s, 0.66; H); $^{13}$C NMR (75.5 NMR, DMSO-$d_6$) δ 18.8, 21.1, 26.8, 28.3, 31.4, 42.8, 47.9, 53.2, 60.3, 60.4, 81.1, 154.8, 166.8, 171.2, 175.2, 176.8.

Example 22

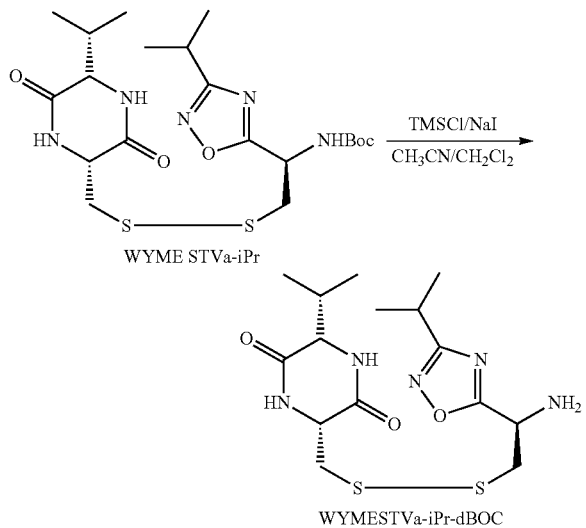

General Procedure for the Dealkylation of Boc Group by Chlorotrimethylsilane/Sodium Iodide.

The reactions were generally carried out in 1 mmol scale in a 10 mL flask and flushed continuously with dry Argon. To a solution of the corresponding dimer (0.25 mmol) and sodium iodide (37.5 mg, 0.25 mmol) in acetonitrile/dichloromethane (5 mL, 2:1) was added chlorotrimethylsilane (27 mg, 0.25 mmol) slowly with continuous stirring. The reaction mixture was stirred at room temperature until the completion of the reaction indicated by TLC. The solvent was removed under reduced pressure and the resulted residue was dissolved into the mixed solvent ($CH_2Cl_2$/methanol=9:1). The solution was washed with small amount of saturated sodium thiosulfate and brine and dried over $Na_2SO_4$. The products were further purified by column chromatography on silica gel (prepared TLC) to yield pure products in over 85% yield.

8 (WYMESTVa-iPr-dBoc): $^1$H NMR (300 NMR, DMSO-$d_6$) δ 0.86 (d, J=6.3 Hz, 3H), 0.96 (d, J=6.9 Hz, 3H), 1.23-1.30 (dd, 6H), 2.20-2.25 (m, 1H), 3.10-3.19 (m, 2H), 3.28-3.30 (m, 2H), 4.23 (s, 1H), 5.09 (s, 1H), 7.09-7.42 (m, 1H), 8.13-8.22 (m, 2H), 9.12-9.42 (br, 1H).

Example 23

Screening for Novel Antipsychotics and Anticraving Drugs: Prepulse Inhibition of Acoustic Startle Deficits in sensorimotor gating are present in schizophrenic patients and often assessed by measuring inhibition of the acoustic startle response following presentation of a non-startling stimulus (prepulse inhibition). Similar to negative and cognitive symptoms of schizophrenia, impairments of prepulse inhibition are thought to reflect altered cortical functioning. Supporting its use as an effective screen for putative antipsychotics, PCP produces deficits in prepulse inhibition in humans and these deficits in PPI have been shown to parallel severity of the disease, such that clinical improvement in schizophrenic patients is paralleled by improvement in pre-pulse inhibition. Conversely $1^{st}$ generation antipsychotics, which are ineffective in treating negative and cognitive symptoms of schizophrenia, fail to alter phencyclidine-induced deficits in PP. As a result, phencyclidine-induced deficits in PPI represent one of the most commonly used screens for putative antipsychotics.

Deficits in sensorimotor gating are sensitive to intact function of the prefrontal cortex. As a results, findings obtained demonstrating improved function of prefrontal cortex following administration of a drug of abuse, e.g. phencyclidine, indicates the potential of a drug to normalize brain function thought to underlie aspects of addiction. It is important to note that efforts to identify the neural basis of addiction implicate excitatory projections from the prefrontal or orbitofrontal cortex to the ventral striatum, which is frequently referred to as the motive circuit, as key projections that likely contribute to the capacity of stimuli to evoke drug craving or drug seeking. Functional imaging studies indicate that selective activation of corticostriatal pathways by cocaine or cocaine-paired cues may contribute, at least in part, to the emergence of intense drug craving. Human cocaine abusers exposed to craving-inducing stimuli exhibit increased activation of excitatory circuits originating in cortical regions, including orbital and prefrontal cortex, and projecting to the ventral striatum. In comparison, cocaine abusers exposed to non-drug reinforcers exhibited diminished activation of these circuits. These data indicate that cocaine-induced plasticity in human abusers renders corticostriatal pathways, which are circuits capable of generating repetitive behaviors in response to salient stimuli, selectively responsive to drug-paired stimuli rather than natural reinforcers. (For review see Kalivas et al., 2005; Kalivas and Volkow, 2005; Volkow et al., 2005)

PCP Dose-Dependently Alters Prepulse Inhibition.

Figure 5:
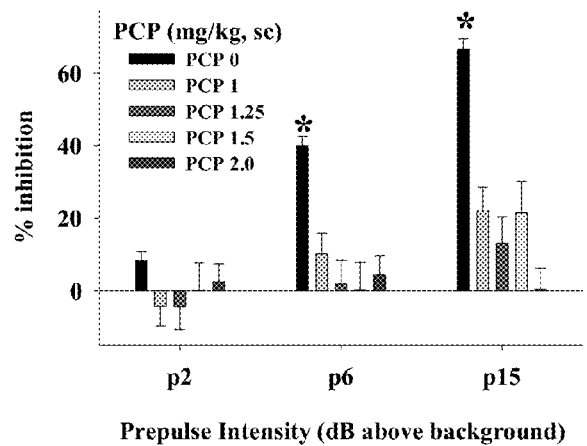
FIG. 5 depicts percent inhibition of a startle response elicited by a loud auditory stimulus (50 dB above background) when preceded by a mild auditory stimulus (2-15 dB above background) in rats treated with pcp (0-2.0 mg/kg, N=9-60/group). * from every other group at respective prepulse intensity, Fisher LSD p<0.05

Sensorimotor gating, a process compromised in schizophrenic patients, is often measured using prepulse inhibition whereby a mild auditory stimulus (prepulse, 2-15 db above background) precedes (100 ms) a startle-eliciting auditory stimulus (50 dB above background). Intact sensorimotor gating will result in suppression of the startle reflex when preceded by the prepulse. Since improvement in prepulse inhibition tracks improvement in symptoms that are largely insensitive to current treatments, this paradigm has become one of the most commonly used screening paradigms. FIG. 5 illustrates the capacity of PCP to disrupt prepulse inhibition, rendering the prepulse ineffective in suppressing the startle reflex. PCP is commonly used to disrupt prepulse inhibition because this abnormality, in addition to negative and cognitive symptoms, are insensitive to $1^{st}$ generation antipsychotics thereby providing predictive validity.

Figure 6:
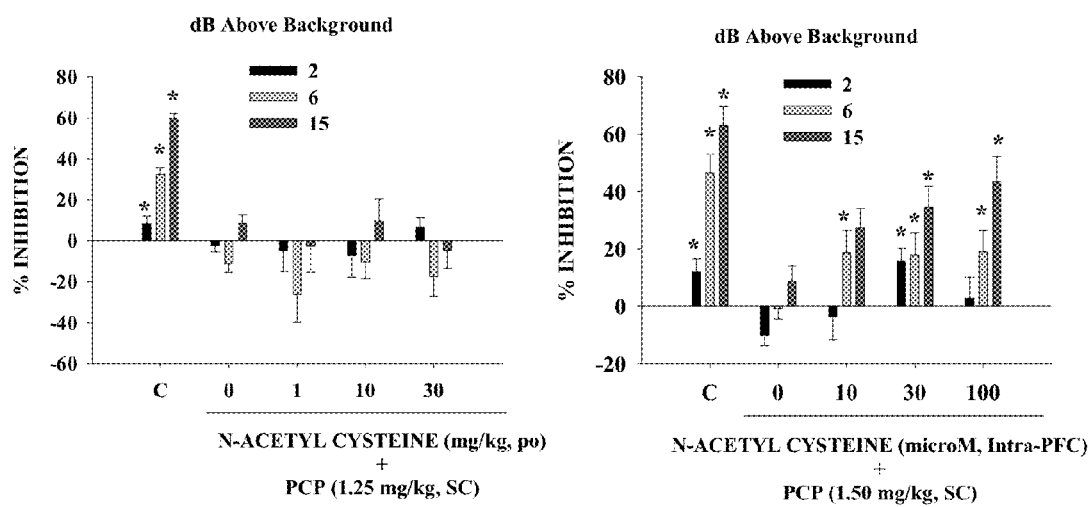
FIG. 6 depicts impact of N-acetyl cysteine on sensorimotor gating deficits produced by phencyclidine administered orally (left) or directly into the prefrontal cortex (right), which is likely the therapeutic site of action for cysteine prodrugs (Baker et al 2008). N=6-46/group. * indicate a significant difference from rats receiving PCP only (e.g., 0 N-acetyl cysteine), Fisher LSD, p, 0.05.

FIG. 6 illustrates the impact of N-acetyl cysteine on sensorimotor gating deficits produced by phencyclidine administered orally (left) or directly into the prefrontal cortex (right), which is likely the therapeutic site of action for cysteine prodrugs (Baker et al 2008). N=6-46/group. * indicates a significant difference from rats receiving PCP only (e.g., 0 N-acetyl cysteine), Fisher LSD, p, 0.05.

Figure 7:
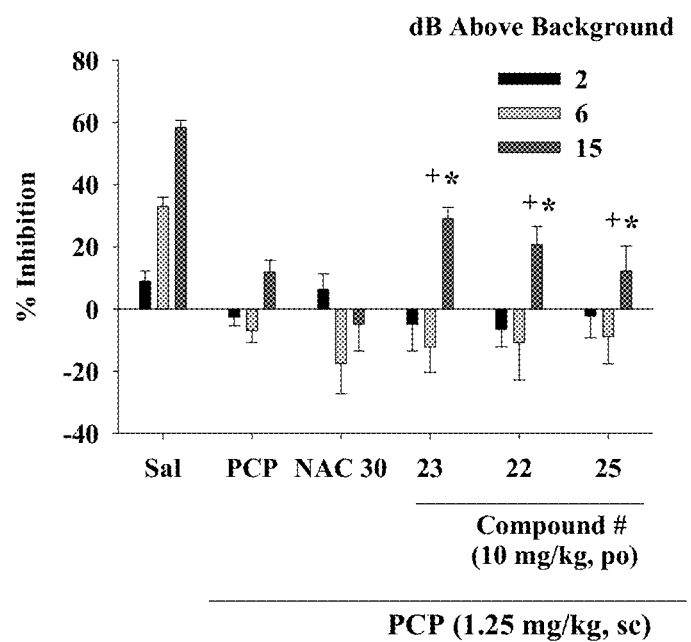
FIG. 7 is a bar graph illustrating inhibition of a startle response in response to a load stimulus (pulse) when preceded by a pre-pulse stimulus (2-15 db above background).

FIG. 7 is a bar graph illustrating inhibition of a startle response in response to a load stimulus (pulse) when preceded by a pre-pulse stimulus (2-15 db above background). Prepulse inhibition is a commonly used paradigm to screen antipsychotic agents for use in treating schizophrenia. The pre-pulse stimulus presented at 15 dB above background reduced the startle response in saline controls (Sal; N=54) by >60% relative to the response elicited following exposure to the pulse only. Rats pretreated with phencyclidine only (PCP; 1.25 mg/kg, SC; N=50) failed to exhibit a reduction in the response elicited by the pulse even when preceded by the pre-pulse (regardless of stimulus intensity). This reflects sensorimotor gating deficits common to patients afflicted with schizophrenia. Rats pretreated (60 min) with N-acetyl cysteine (30 mg/kg, po) failed to exhibit sensorimotor gating. Note direct delivery of N-acetyl cysteine into the brain reverses phencyclidine-induced deficits in sensorimotor gating (FIG. 6), which is consistent with clinical trials establishing the antipsychotic efficacy of this compound (Berk et al., 2008). Rats pretreated (60 min) with compounds 23, 22, and 25 (N=8/group) exhibited a significant difference relative to either rats receiving PCP alone (*, Fisher LSD, p<0.05) and/or N-acetylcysteine (N 30; 30 mg/kg; +, Fisher LSD, p<0.05). Collectively, these data indicate the efficacy of these compounds and synthesis schemes to generate novel antipsychotics that exceed the potential of N-acetyl cysteine.

Compounds MWL 235 and MWL 299 are anxiolytic, as demonstrated in the Elevated Plus Maze (see Savic, M, Cook, J., et al., Pharm. Biochem. Behav., 79, 279-290, 2004, for the standard method in the EPM).

Example 24

Biological Data for Compounds of the Invention and for Related Monomers and Dimers The biological data reported in Examples 24-27 shows additional results for compounds of the invention and for related monomers and dimers. The compounds are related to the purposed unsymmetrical cystine bioisosteres (and/or prodrugs) disulfides based on being monomers or intermediates of the purposed unsymmetrical dimers, having similar chemical structures of the monomers and/or dimers of the purposed unsymmetrical dimers, and/or having similar synthetic routes as the purposed unsymmetrical dimers.

The $C^{14}$ Uptake test shows the compounds ability to compete with $C^{14}$ labeled cystine into the cell. A decrease in the $C^{14}$ labeled cystine uptake indicates that the compound is competing with and/or restricting $C^{14}$ labeled cystine uptake. The glutamate percent change test shows the percent change in glutamate after the cell is treated with a solution of the compound. This change represents the activation and turnover of the cystine-glutamate antiporter. The higher the response in the glutamate percent change, compared to the control, the more effective the compound is at driving the cystine-glutamate antiporter and increasing glutamate levels in the extra-synaptic space.

Example 25

$^{14}C$ Uptake and Glutamate Release by Compounds of the Invention and Related Compounds The goal of these experiments was to determine $^{14}C$ uptake and glutamate release by a number of compounds of the invention.

In an exemplary $^{14}C$ uptake experiment, the screening of compounds is performed using an in vitro culture system of human glial cells from brain astrocytoma (1321N1). Cells are plated on 24 well plates coated with poly-D-lysine and laminin and grown in a balanced salt solution supplemented with 5% heat inactivated horse serum, 5% fetal bovine serum, 2 mM glutamine and glucose (total 21 mM). Cultures are maintained in humidified 5% $CO_2$ incubators at 37° C. for 3-4 days before experiments were performed. At this time, the cultures has formed a single confluent layer.

Cultures are washed 3 times in Na-free HEPES and $HCO_3^-$ buffered balanced salt solution. After one hour, zero time point samples are taken for glutamate analysis by HPLC, at which point test compounds are added. $^{14}C$-cystine (0.025 mCi/mL) is then added for 20 minutes. Following the $^{14}C$-cystine exposure, cultures are washed three times with ice cold HEPES buffered saline solution and dissolved in 250 ul sodium dodecyl sulfate (0.1%). An aliquot (200 ul) is removed and added to scintillation fluid for counting. Values are normalized to $^{14}C$-cystine uptake in untreated controls on the same experimental plate.

In an exemplary $^3H$-glutamate release experiment, the assay also uses the cell culture system of human glial cells from brain astrocytoma (1321N1) described above. Initially, cells are washed with sodium-free HBBSS, and $^3H$-glutamate is added (PerkinElmer: 1 mCi/mL stock solution is diluted (30 uL+500 uL sodium-free HBBSS) and 10 uL of diluted radiolabel is added to each well). Following a one hour incubation to load the cells with labeled glutamate, the cells are washed again with sodium-free HBBSS, and the drug is added. At 30, 90, and 180 minutes, 50 uL of extracellular media is sampled from each well and is measured using a Beckman LS 6500 scintillation counter.

Figure 8A:
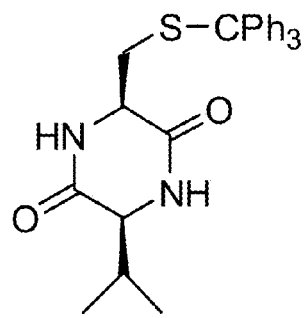
FIG. 8 shows (A) the chemical structure of compound WYME STVa, (B) a bar graph illustrating $C^{14}$ uptake test results for compound WYME STVa, and (C) a bar graph illustrating glutamate percent change test results for compound WYME STVa.
Figure 8B:
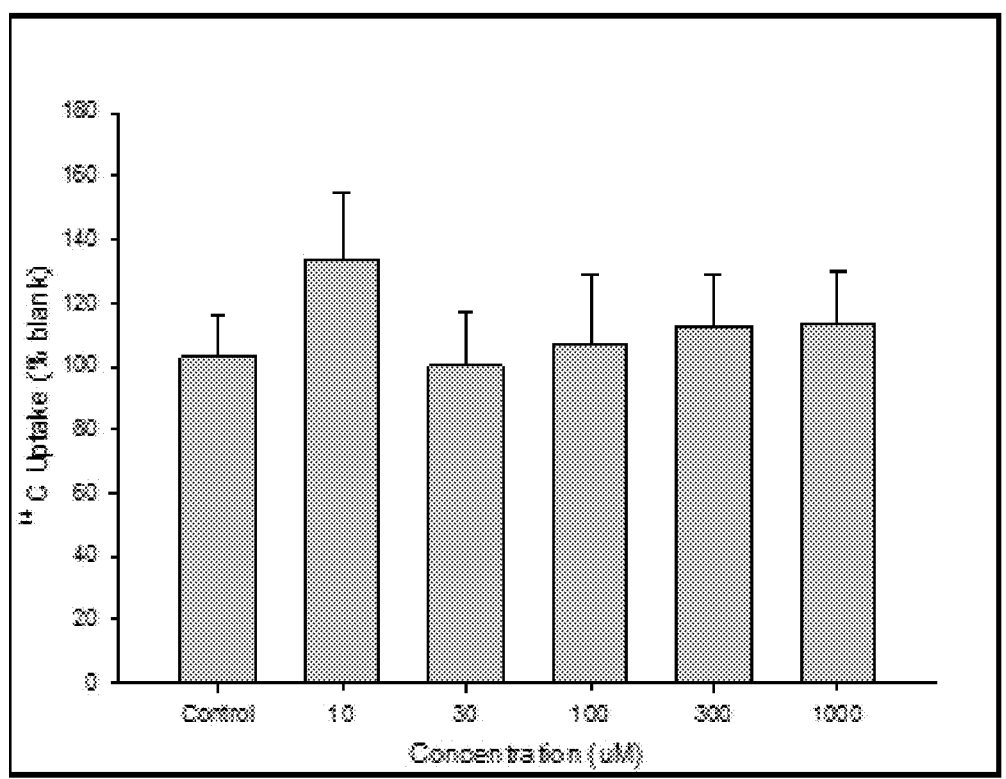
Figure 8C:
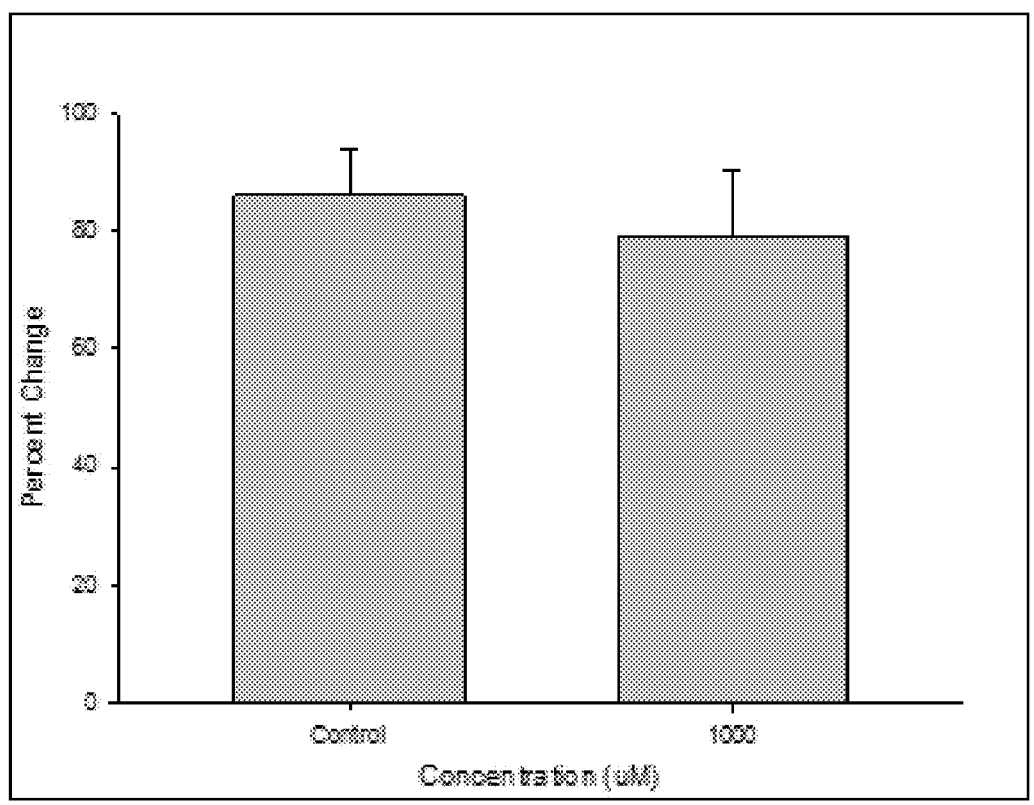
Figure 9A:
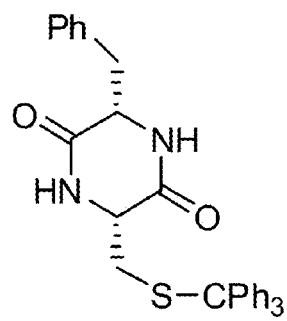
FIG. 9 shows (A) the chemical structure of compound WYME STP6, (B) a bar graph illustrating $C^{14}$ uptake test results for compound WYME STP6, and (C) a bar graph illustrating glutamate percent change test results for compound WYME STP6.
Figure 9B:
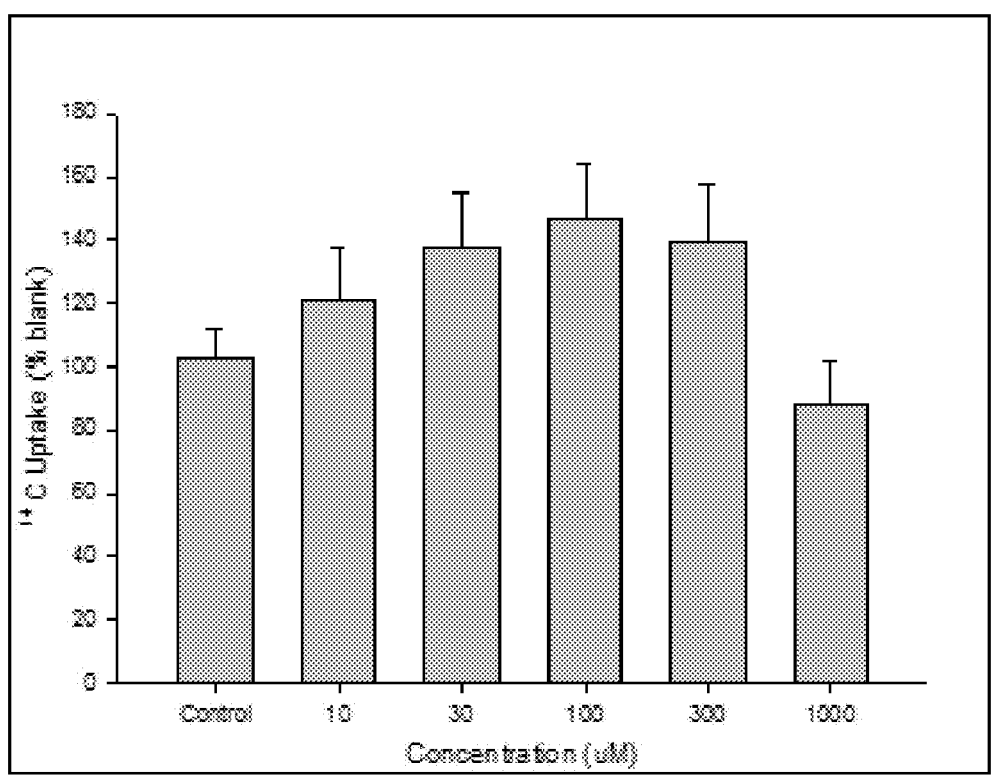
Figure 9C:
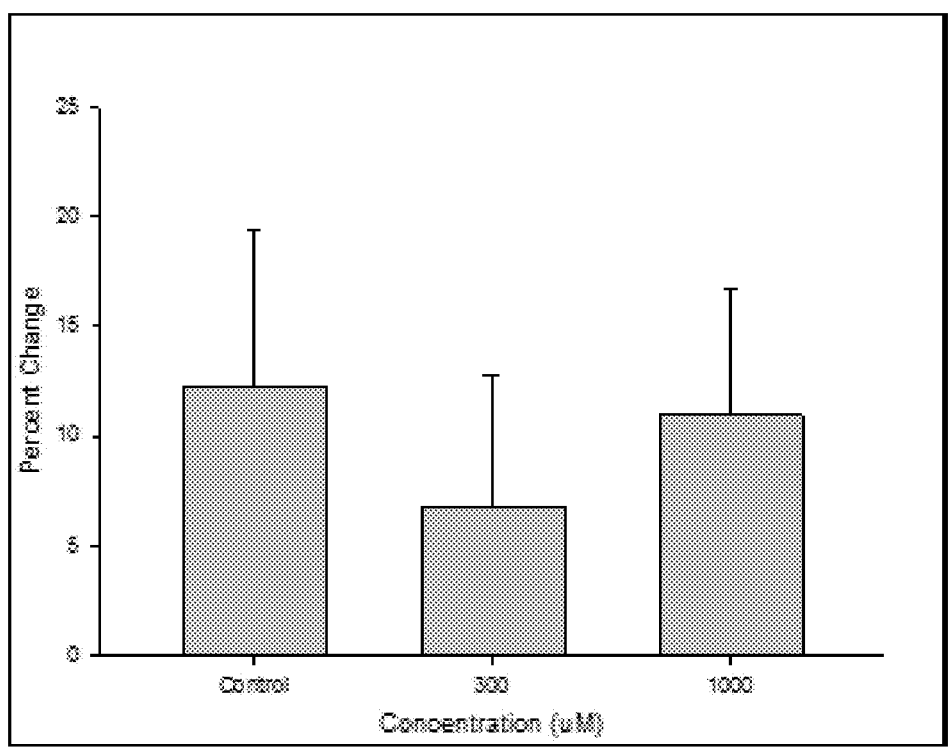
Figure 10A:
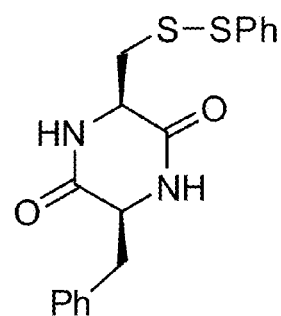
FIG. 10 shows (A) the chemical structure of compound WYME SBP6, (B) a bar graph illustrating $C^{14}$ uptake test results for compound WYME SBP6, and (C) a bar graph illustrating glutamate percent change test results for compound WYME STB6.
Figure 10B:
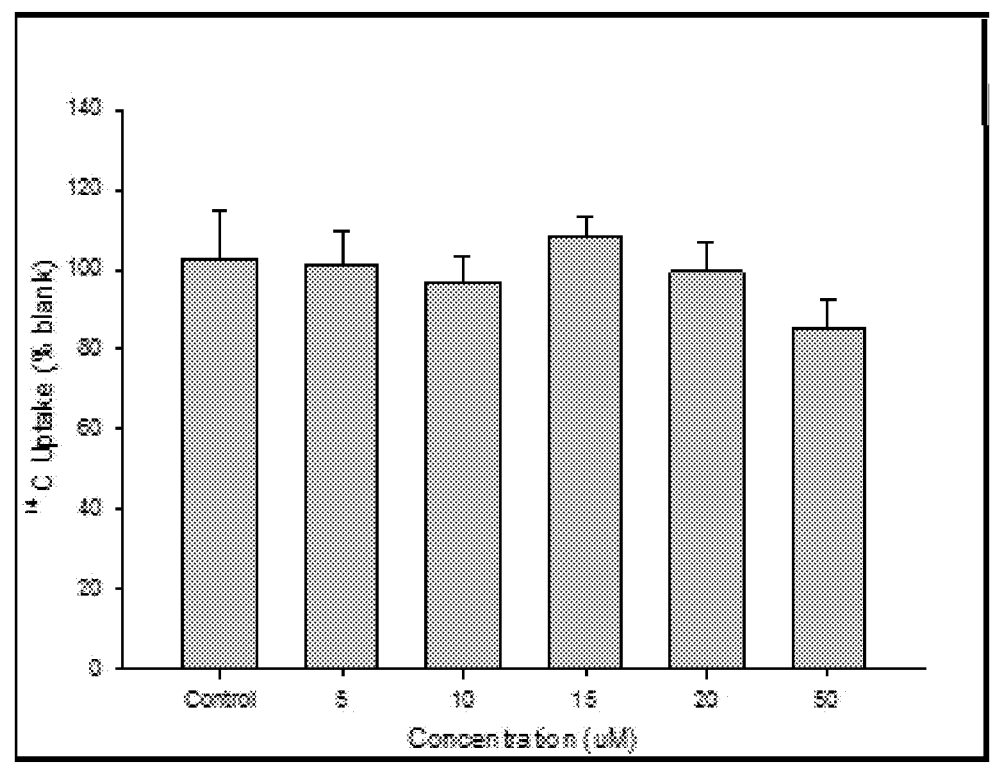
Figure 10C:
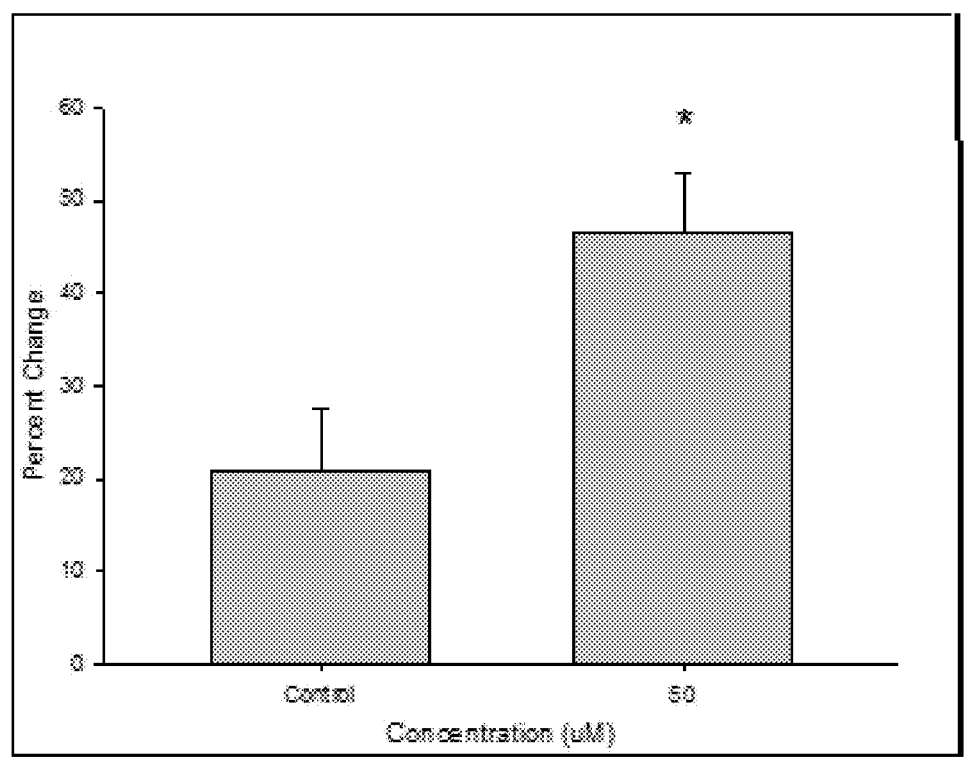
Figure 11A:
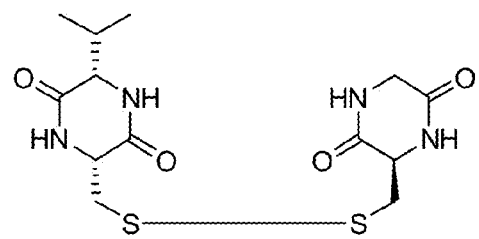
FIG. 11 shows (A) the chemical structure of compound WYME STGV, (B) a bar graph illustrating $C^{14}$ uptake test results for compound WYME STGV, and (C) a bar graph illustrating glutamate percent change test results for compound WYME STGV.
Figure 11B:
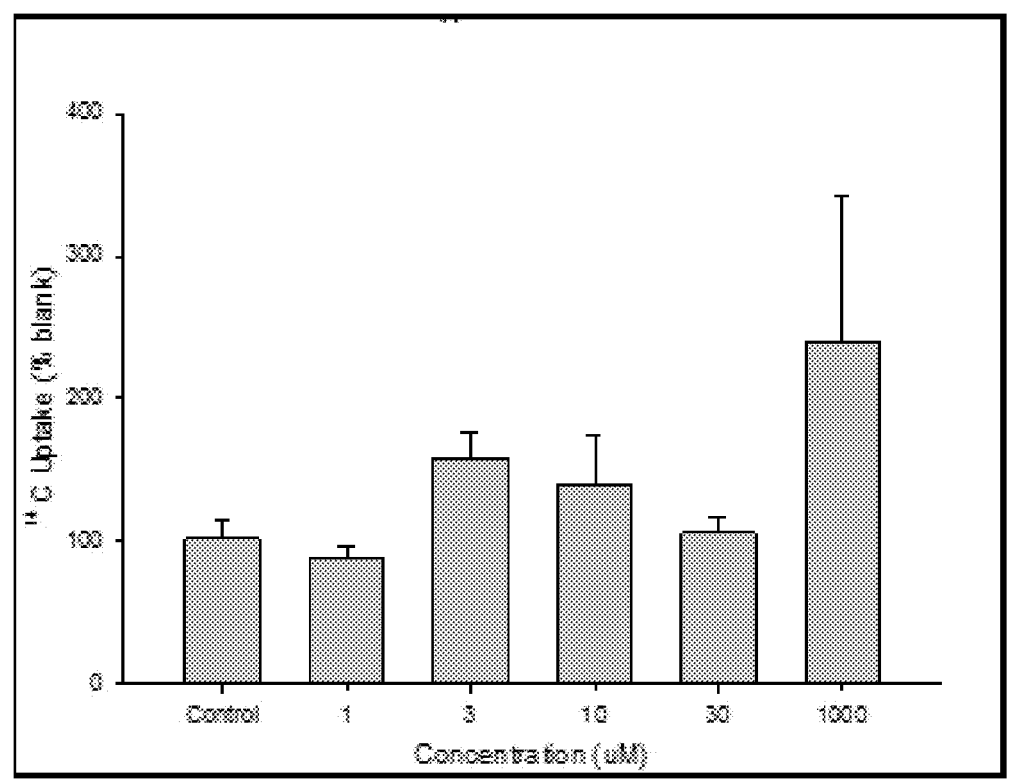
Figure 11C:
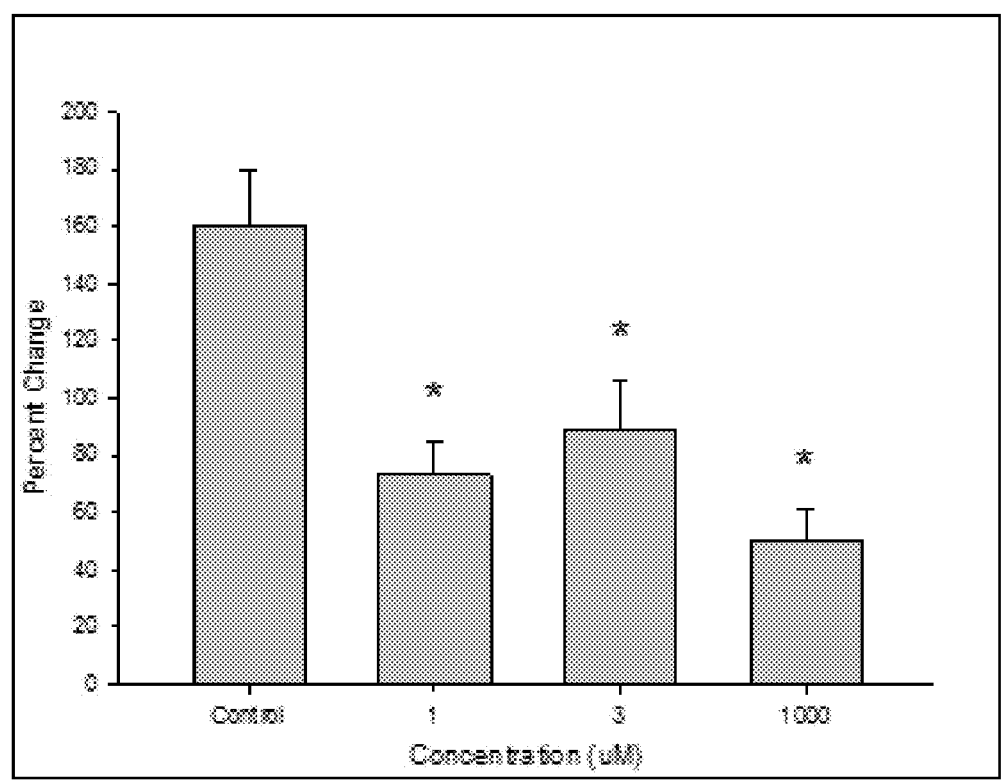
Figure 12A:
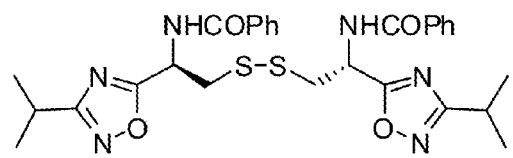
FIG. 12 shows (A) the chemical structure of compound WYME SSI PNPh, (B) a bar graph illustrating $C^{14}$ uptake test results for compound WYME SSI PNPh, and (C) a bar graph illustrating glutamate percent change test results for compound WYME SSI PNPh.
Figure 12B:
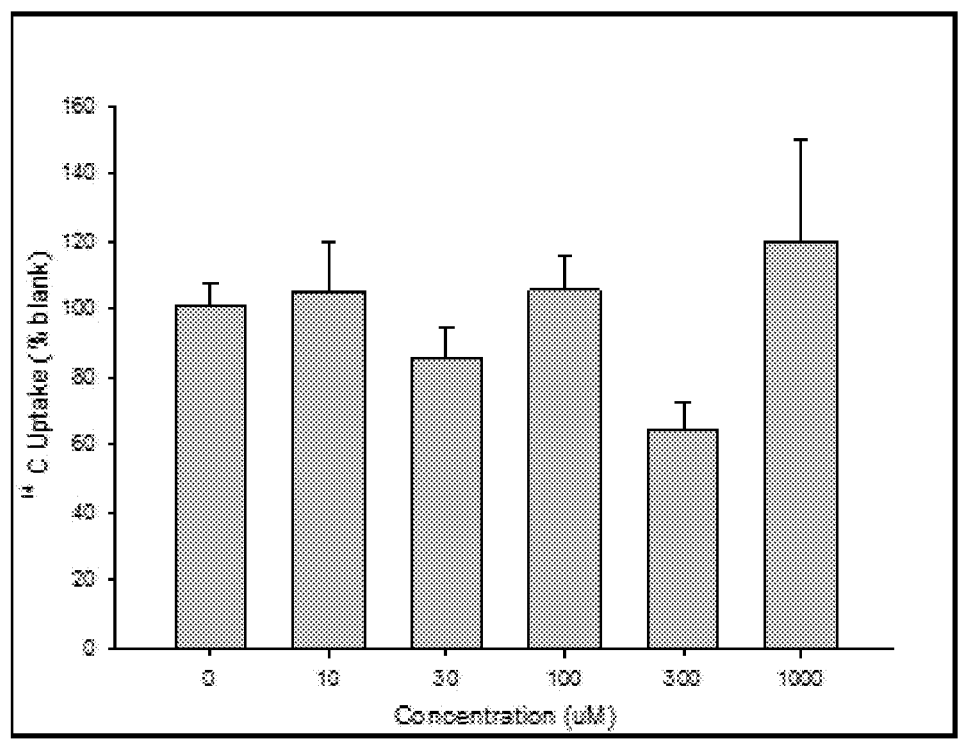
Figure 12C:
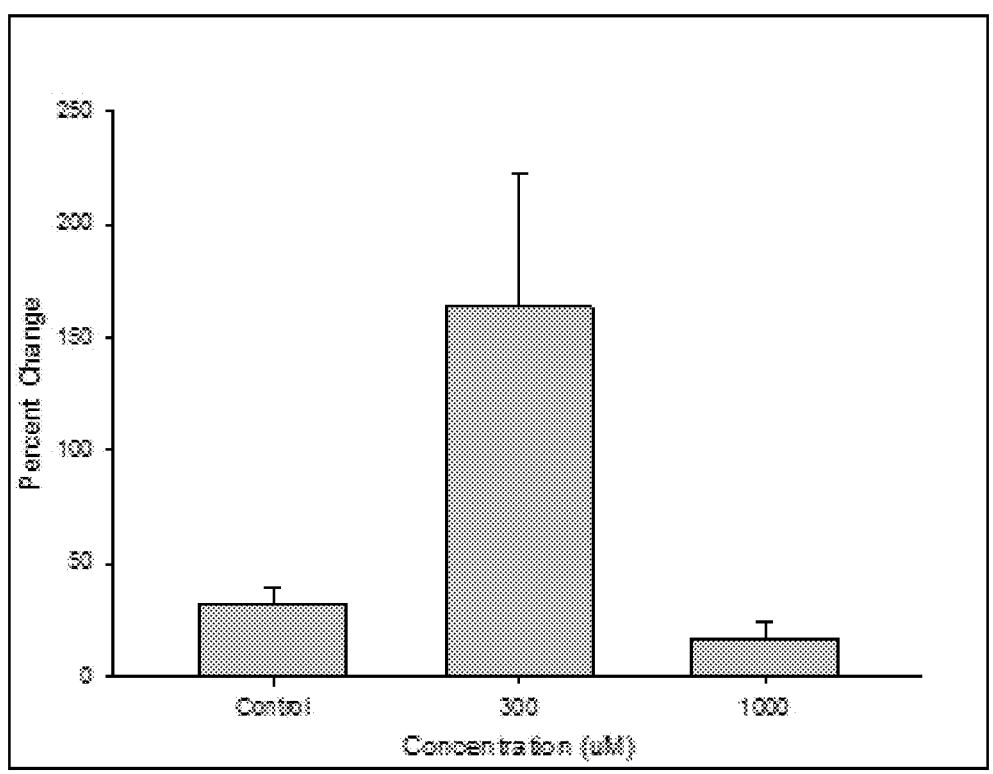

The results of these tests are illustrated in the attached figures. FIG. 8 shows the chemical structure of compound WYME STVa (A), a bar graph illustrating $C^{14}$ uptake test results for compound WYME STVa (B), and a bar graph illustrating glutamate percent change test results for compound WYME STVa (C). FIG. 9 shows the chemical structure of compound WYME STP6 (A), a bar graph illustrating $C^{14}$ uptake test results for compound WYME STP6 (B), and a bar graph illustrating glutamate percent change test results for compound WYME STP6 (C). FIG. 10 shows the chemical structure of compound WYME SBP6 (A), a bar graph illustrating $C^{14}$ uptake test results for compound WYME SBP6 (B), and a bar graph illustrating glutamate percent change test results for compound WYME STB6 (C). FIG. 11 shows the chemical structure of compound WYME STGV (A), a bar graph illustrating $C^{14}$ uptake test results for compound WYME STGV (B), and a bar graph illustrating glutamate percent change test results for compound WYME STGV (C). FIG. 12 shows the chemical structure of compound WYME SSI PNPh (A), a bar graph illustrating $C^{14}$ uptake test results for compound WYME SSI PNPh (B), and a bar graph illustrating glutamate percent change test results for compound WYME SSI PNPh (C).

Figure 13A:
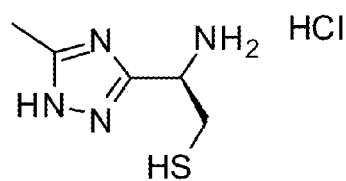
FIG. 13 shows (A) the chemical structure of compound MWL 273 (HCl salt), (B) a bar graph illustrating $C^{14}$ uptake test results for compound MWL 273, and (C) a bar graph illustrating glutamate percent change test results for compound MWL 273.
Figure 13B:
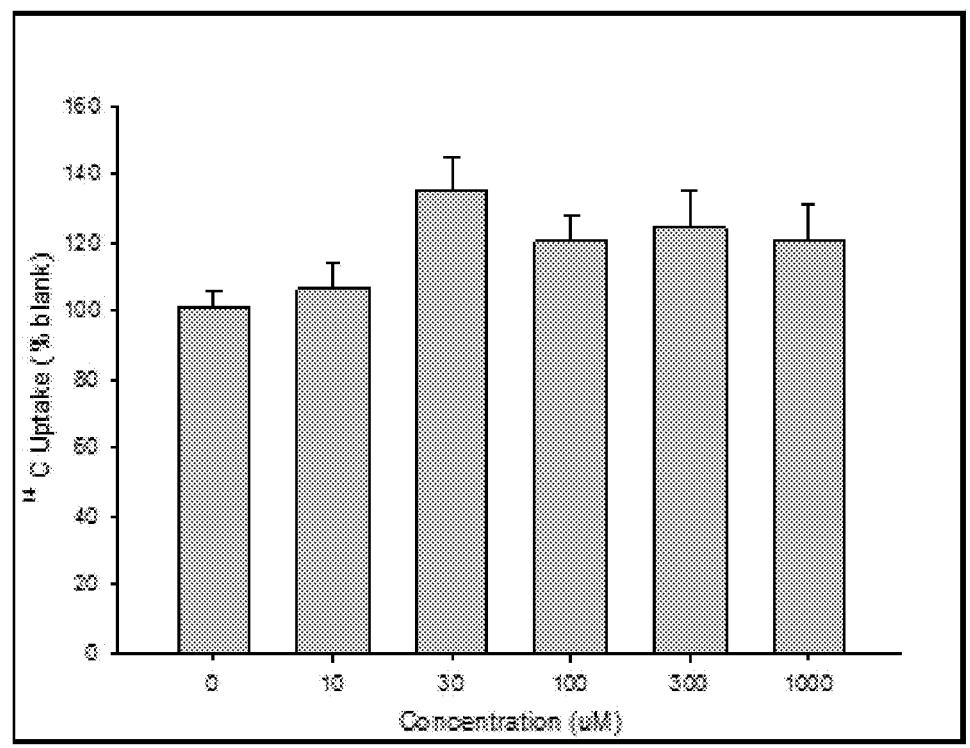
Figure 13C:
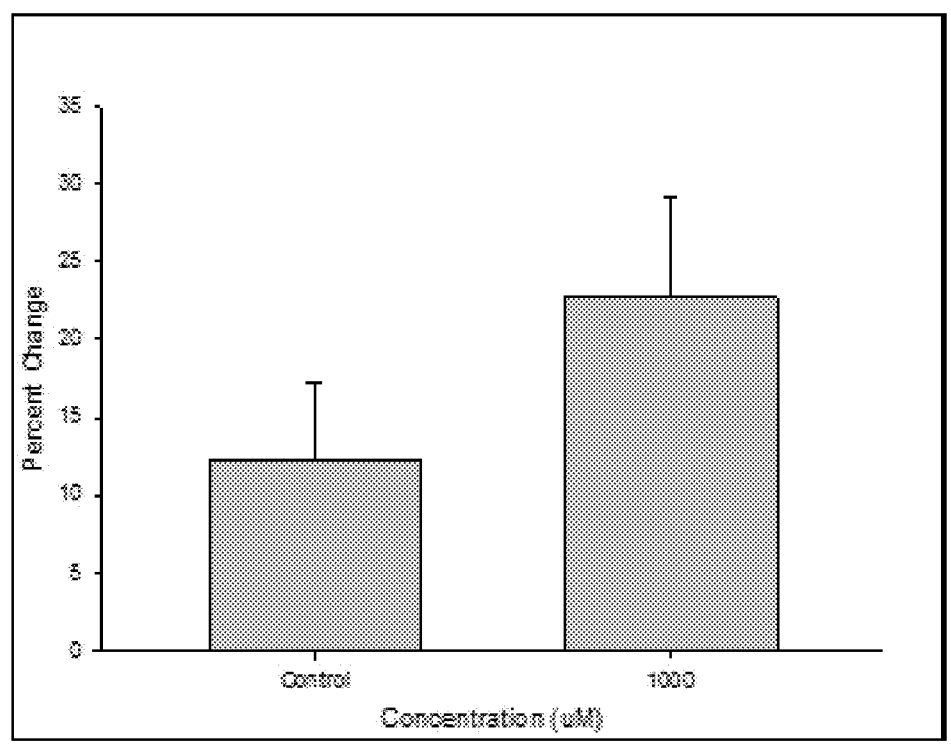
Figure 14A:
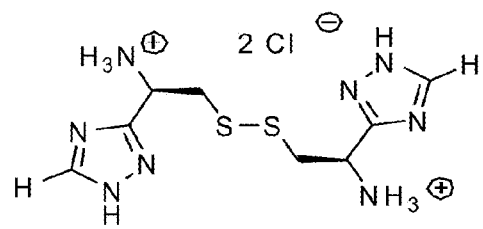
FIG. 14 shows (A) the chemical structure of compound MWL 249 (HCl salt), (B) a bar graph illustrating $C^{14}$ uptake test results for compound MWL 249, and (C) a bar graph illustrating glutamate percent change test results for compound MWL 249.
Figure 14B:
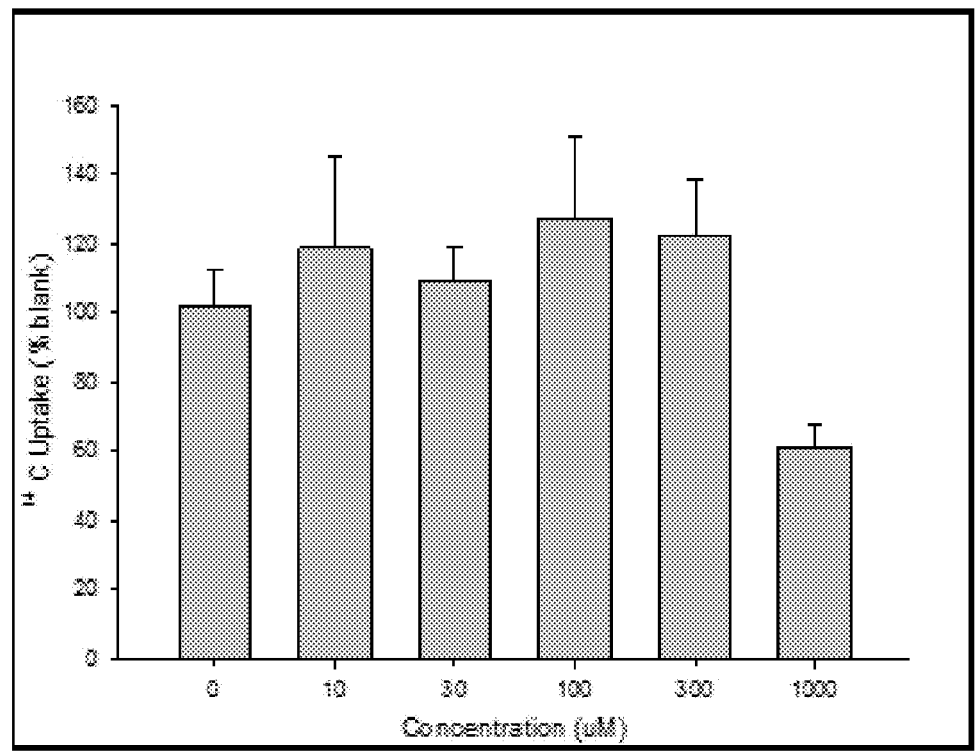
Figure 14C:
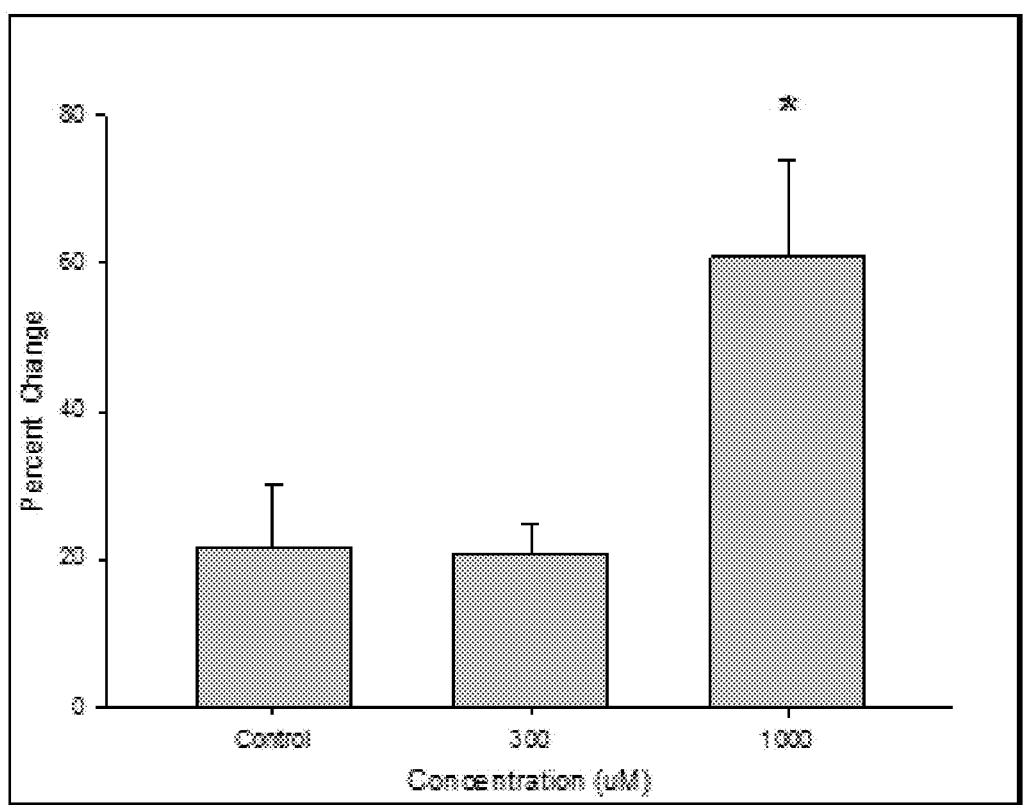
Figure 15A:
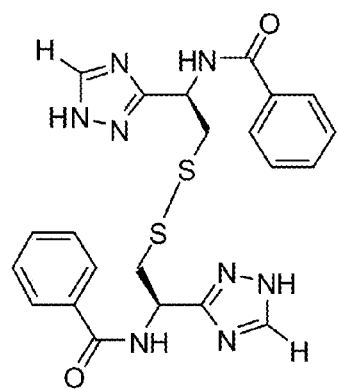
FIG. 15 shows (A) the chemical structure of compound MWL 299, (B) a bar graph illustrating $C^{14}$ uptake test results for compound MWL 299, and (C) a bar graph illustrating glutamate percent change test results for compound MWL 299.
Figure 15B:
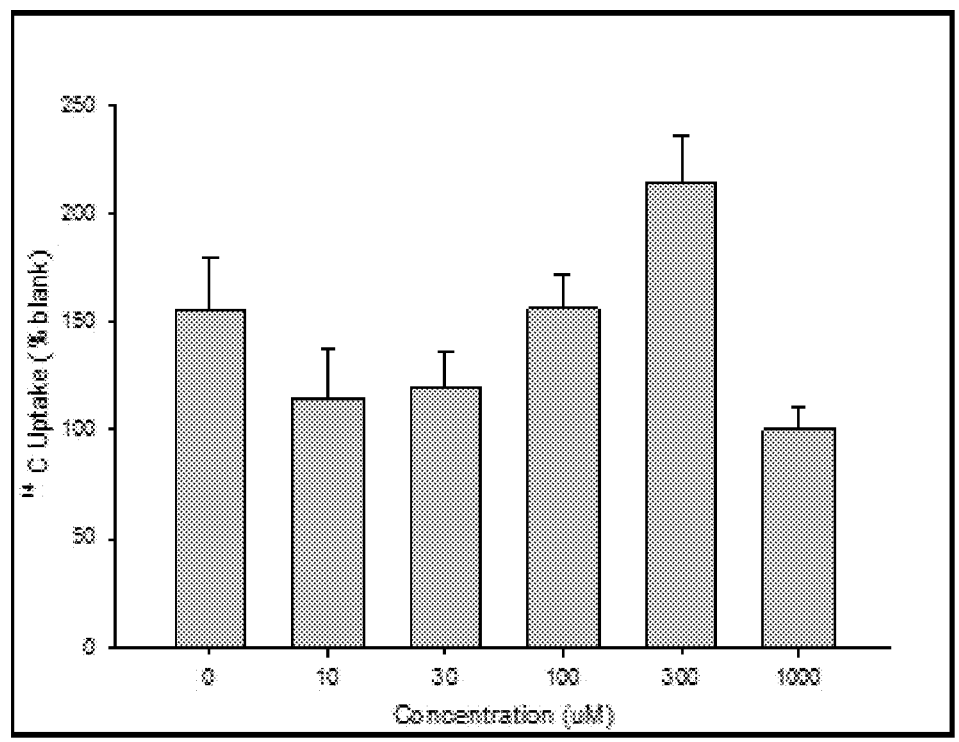
Figure 15C:
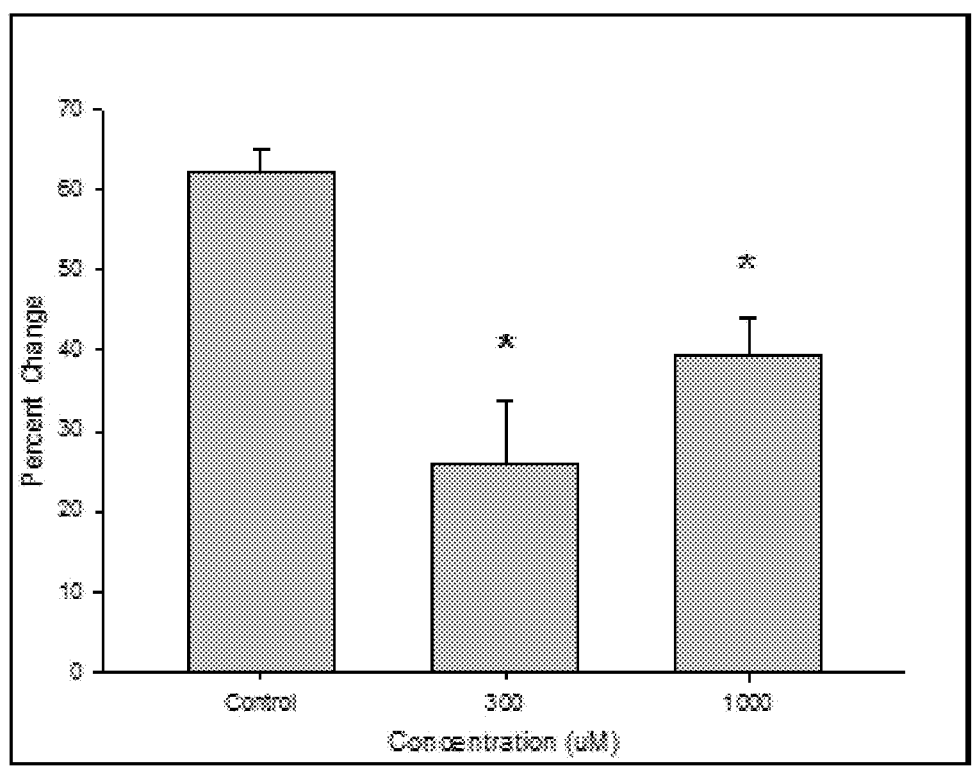
Figure 16A:
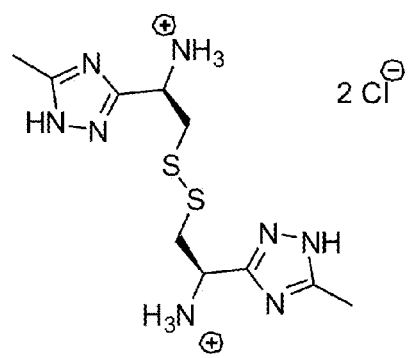
FIG. 16 shows (A) the chemical structure of compound MWL 224 (HCl salt), (B) a bar graph illustrating $C^{14}$ uptake test results for compound MWL 224, and (C) a bar graph illustrating glutamate percent change test results for compound MWL 224.
Figure 16B:
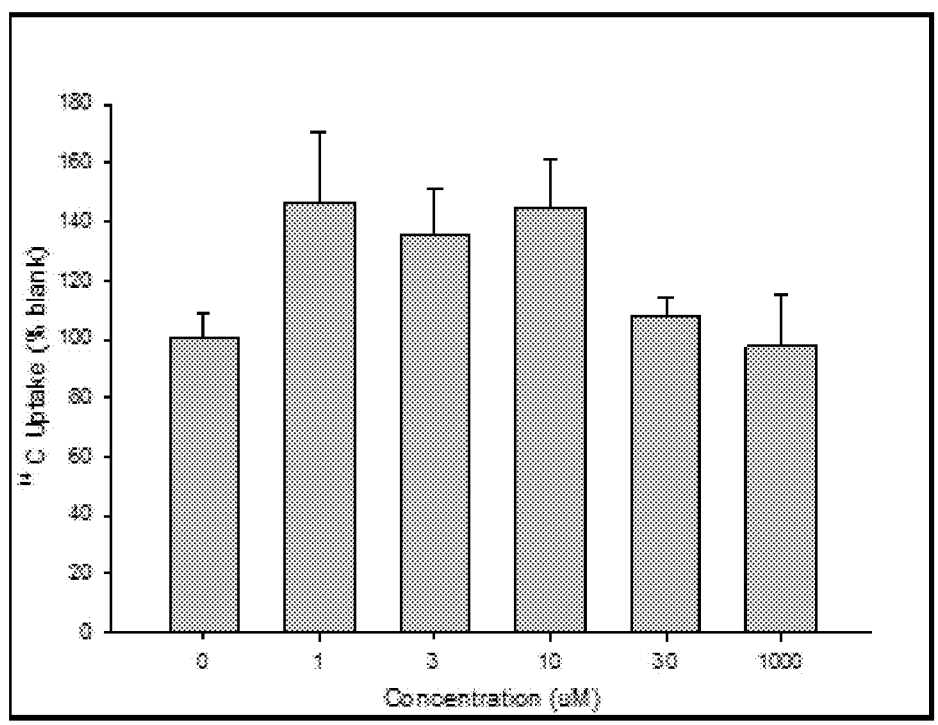
Figure 16C:
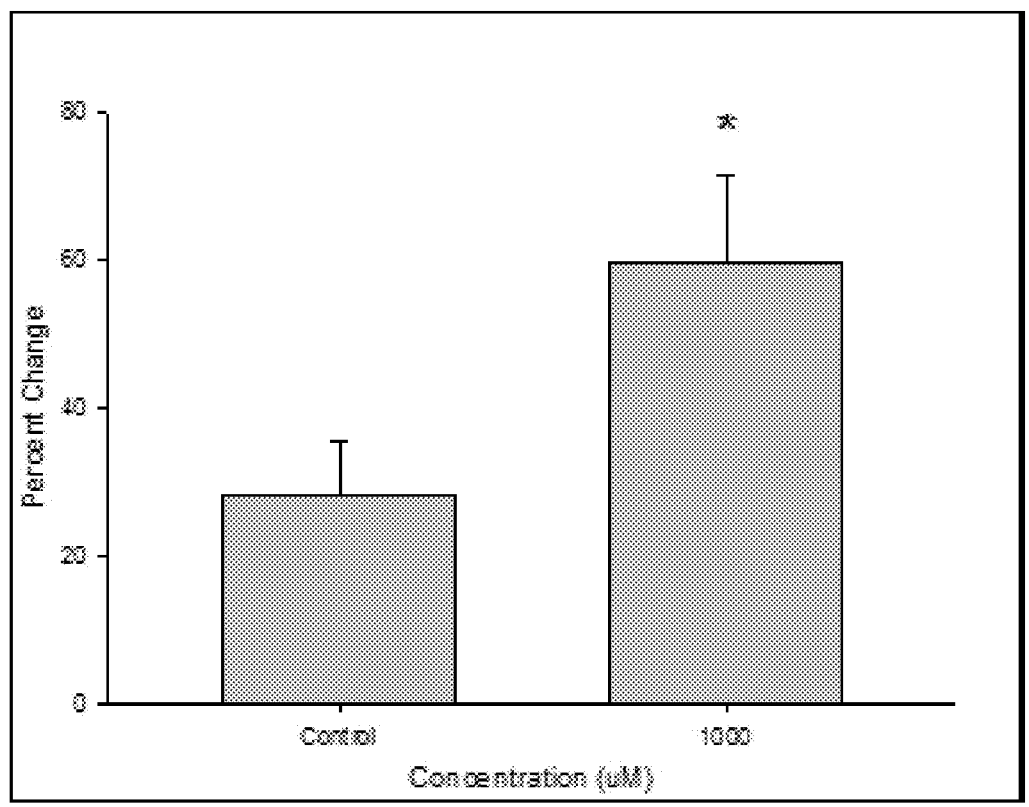
Figure 17A:
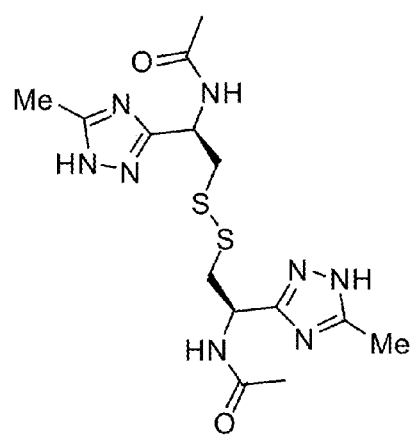
FIG. 17 shows (A) the chemical structure of compound MWL 258, (B) a bar graph illustrating $C^{14}$ uptake test results for compound MWL 258, and (C) a bar graph illustrating glutamate percent change test results for compound MWL 258.
Figure 17B:
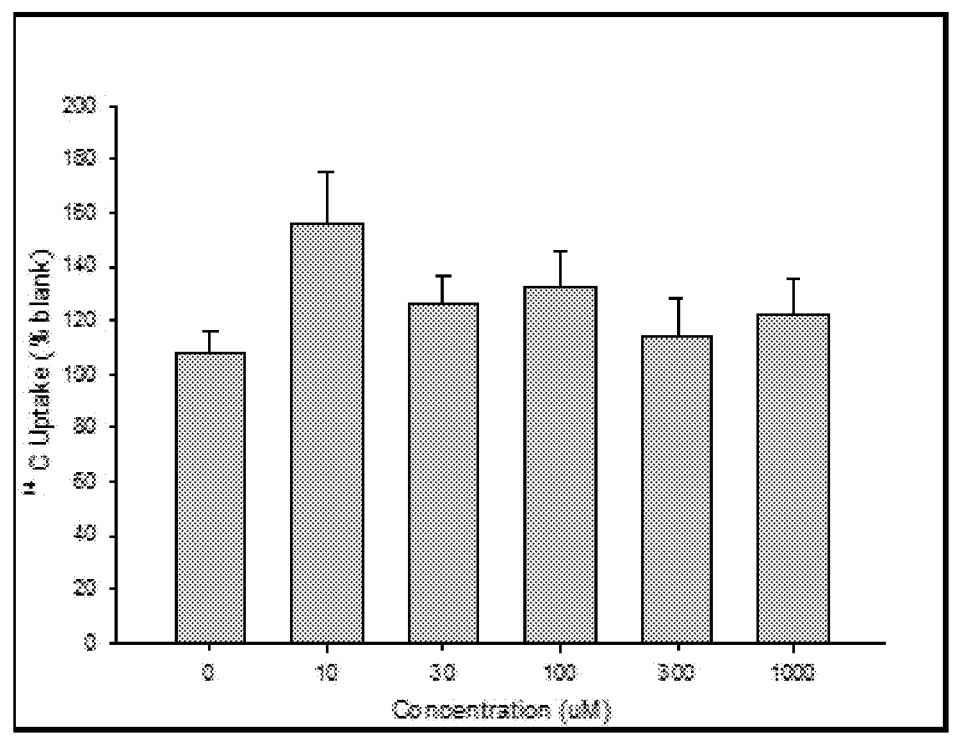
Figure 17C:
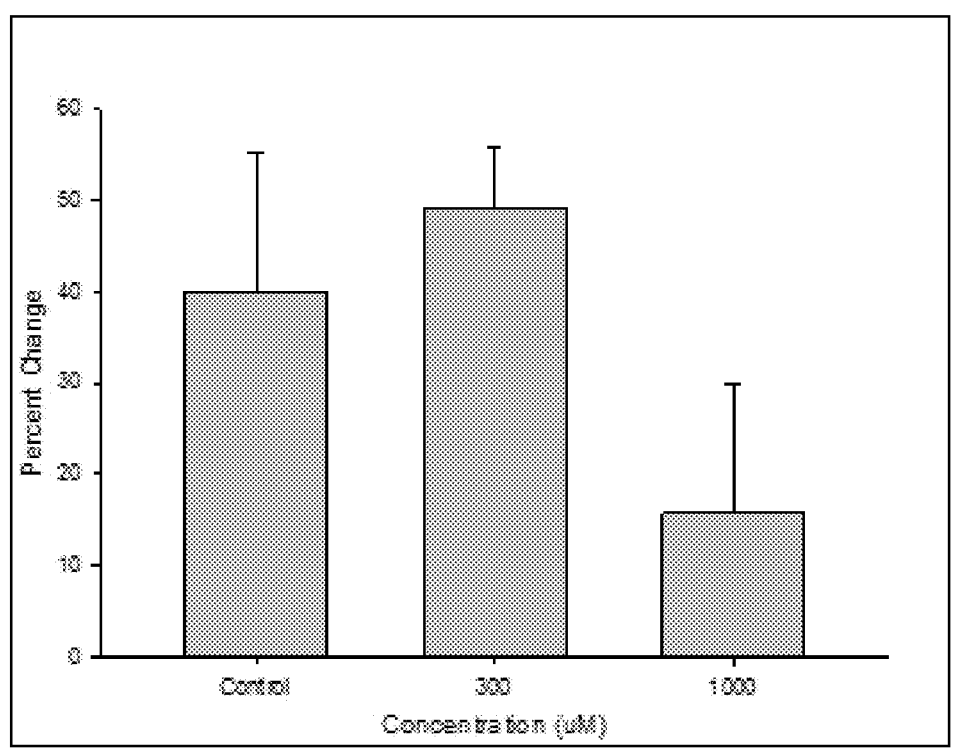

FIG. 13 shows the chemical structure of compound MWL 273 (HCl salt) (A), a bar graph illustrating $C^{14}$ uptake test results for compound MWL 273 (B), and a bar graph illustrating glutamate percent change test results for compound MWL 273 (C). FIG. 14 shows the chemical structure of compound MWL 249 (HCl salt) (A), a bar graph illustrating $C^{14}$ uptake test results for compound MWL 249 (B), and a bar graph illustrating glutamate percent change test results for compound MWL 249 (C). FIG. 15 shows the chemical structure of compound MWL 299 (A), a bar graph illustrating $C^{14}$ uptake test results for compound MWL 299 (B), and a bar graph illustrating glutamate percent change test results for compound MWL 299 (C). FIG. 16 shows the chemical structure of compound MWL 224 (HCl salt) (A), a bar graph illustrating $C^{14}$ uptake test results for compound MWL 224 (B), and a bar graph illustrating glutamate percent change test results for compound MWL 224 (C). FIG. 17 shows the chemical structure of compound MWL 258 (A), a bar graph illustrating $C^{14}$ uptake test results for compound MWL 258 (B), and a bar graph illustrating glutamate percent change test results for compound MWL 258 (C).

Figure 18A:
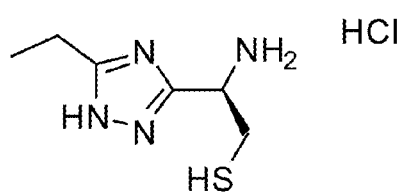
FIG. 18 shows (A) the chemical structure of compound MWL 283 (HCl salt), also designated as compound Pro-090 (B) a bar graph illustrating $C^{14}$ uptake test results for compound MWL 283/Pro-090, and (C) a bar graph illustrating glutamate percent change test results for compound MWL 283/Pro-090.
Figure 18B:
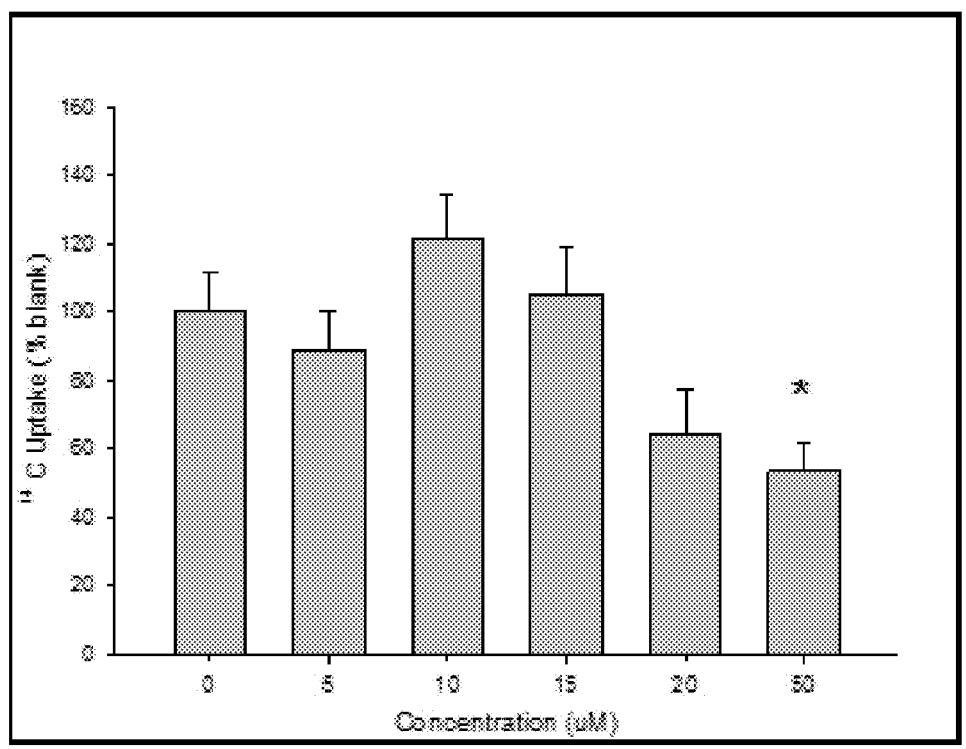
Figure 18C:
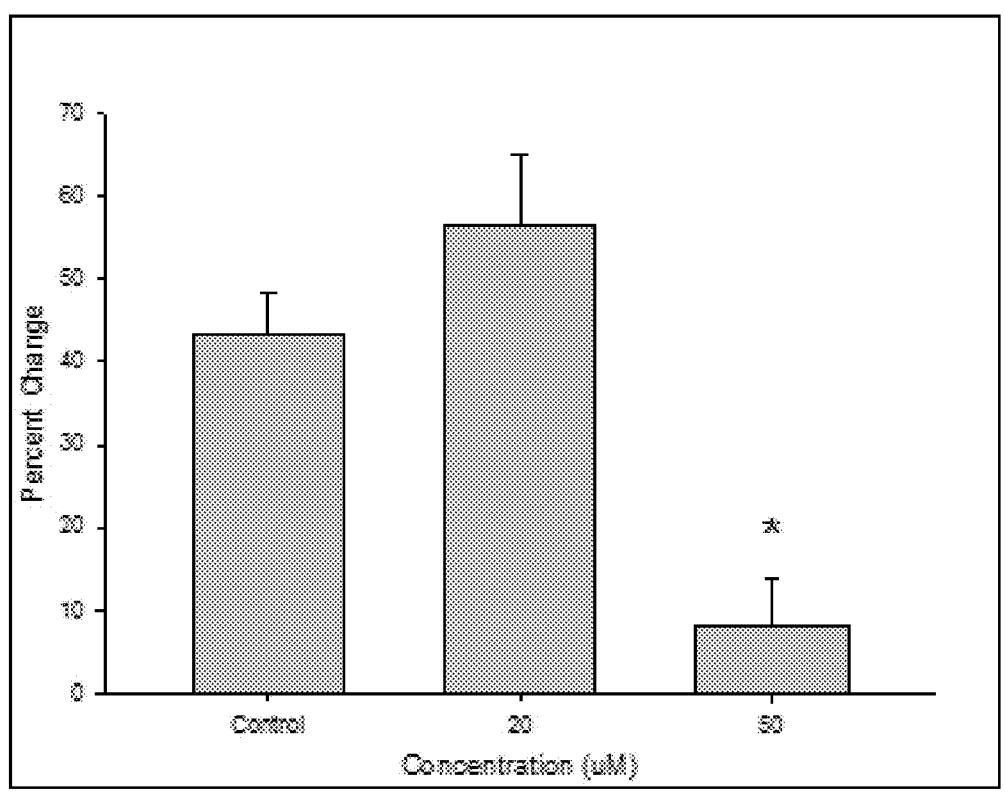
Figure 19A:
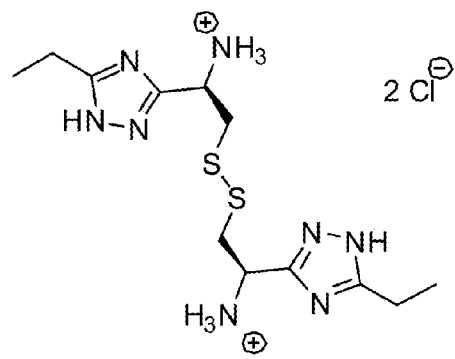
FIG. 19 shows (A) the chemical structure of compound MWL 235 (HCl salt), (B) a bar graph illustrating $C^{14}$ uptake test results for compound MWL 299, and (C) a bar graph illustrating glutamate percent change test results for compound MWL 299.
Figure 19B:
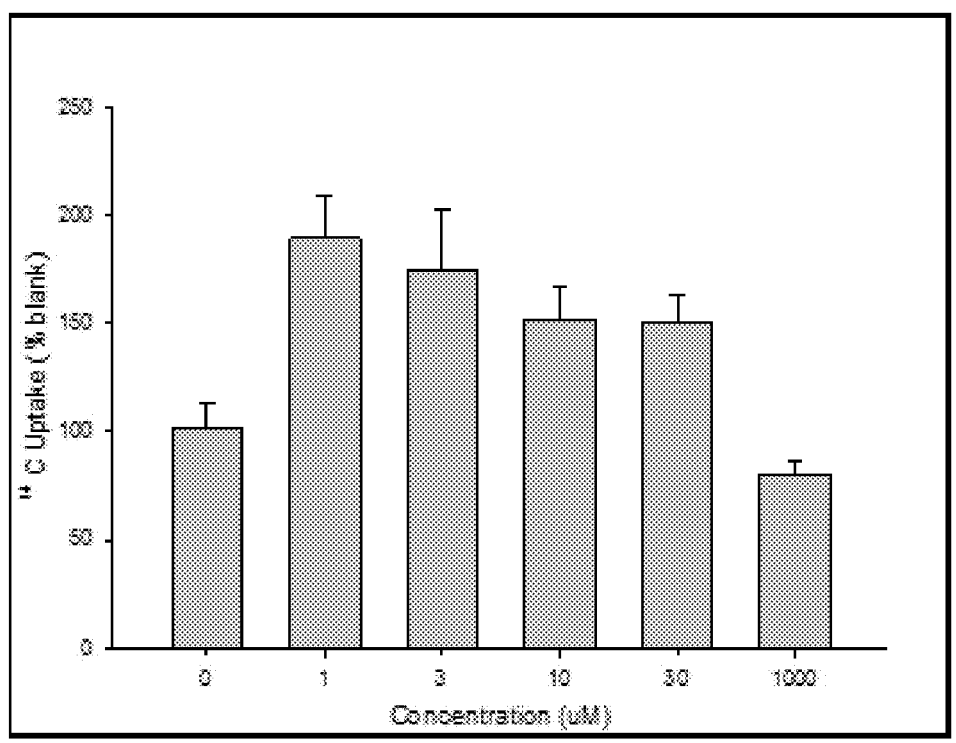
Figure 19C:
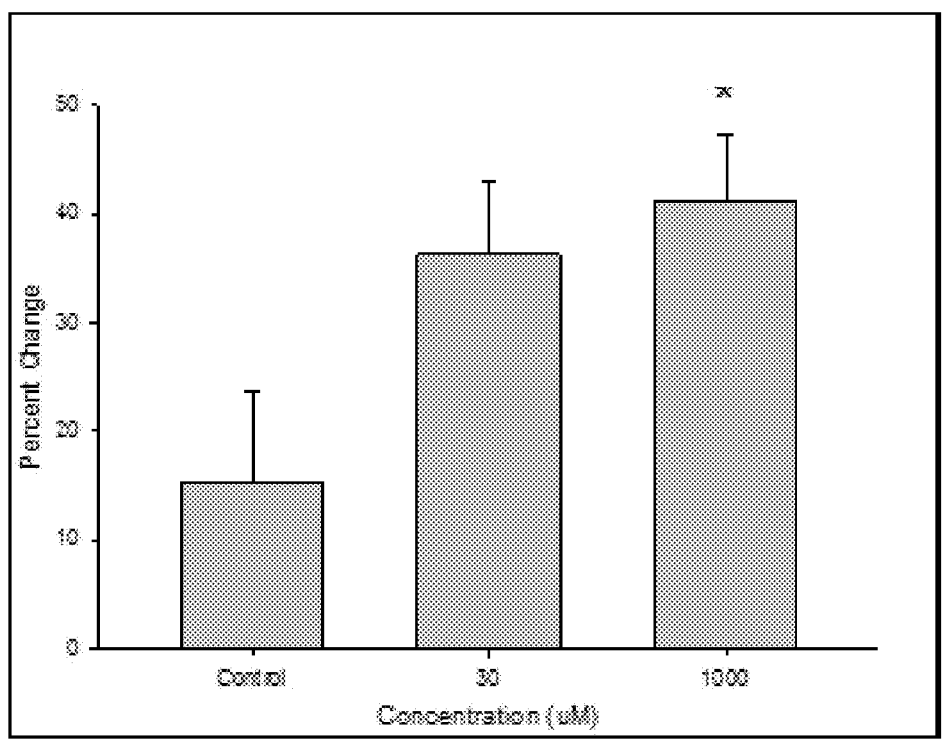
Figure 20A:
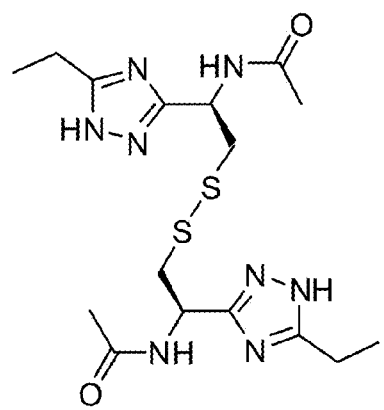
FIG. 20 shows (A) the chemical structure of compound MWL 309, (B) a bar graph illustrating $C^{14}$ uptake test results for compound MWL 309, and (C) a bar graph illustrating glutamate percent change test results for compound MWL 309.
Figure 20B:
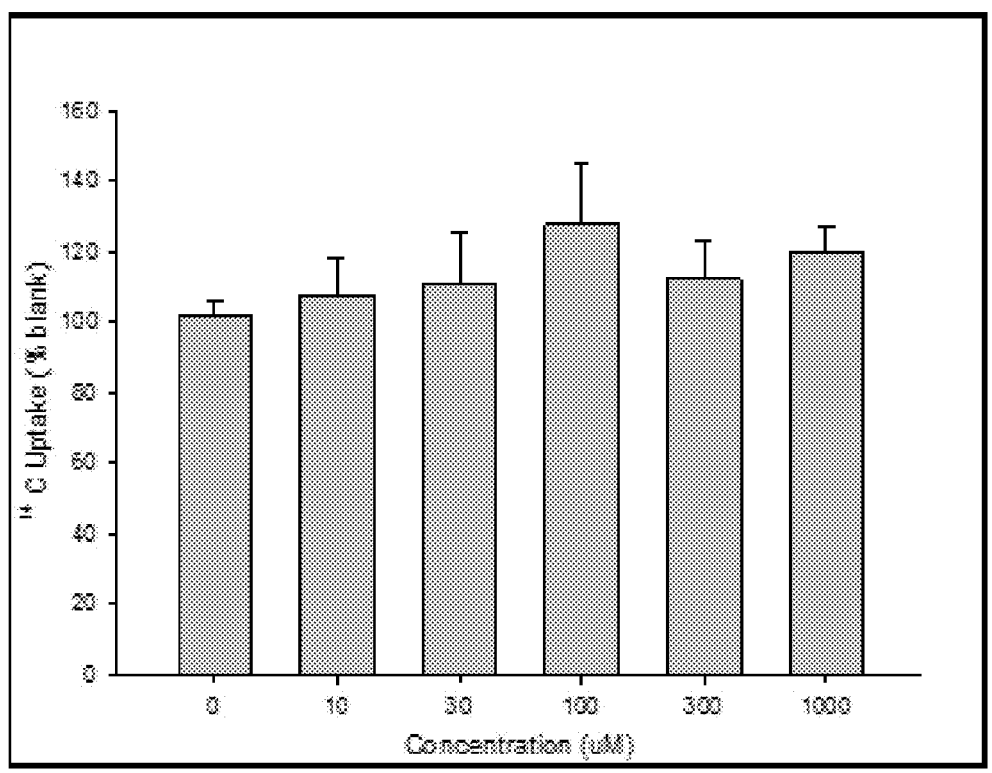
Figure 20C:
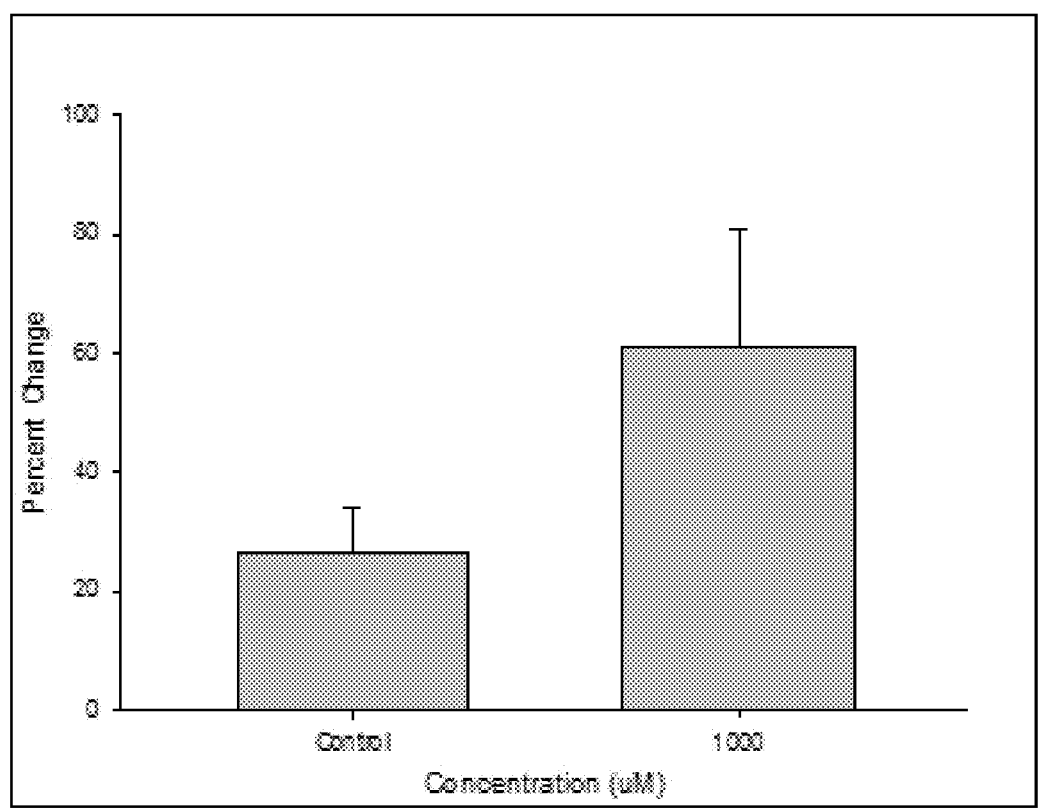
Figure 21A:
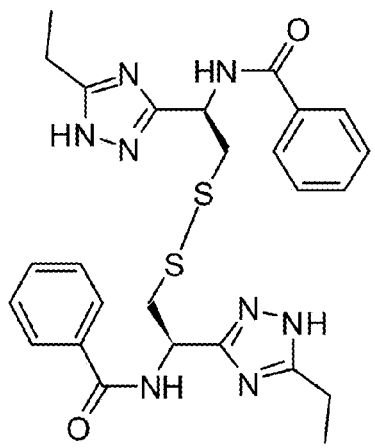
FIG. 21 shows (A) the chemical structure of compound MWL 284, (B) a bar graph illustrating $C^{14}$ uptake test results for compound MWL 284, and (C) a bar graph illustrating glutamate percent change test results for compound MWL 284.
Figure 21B:
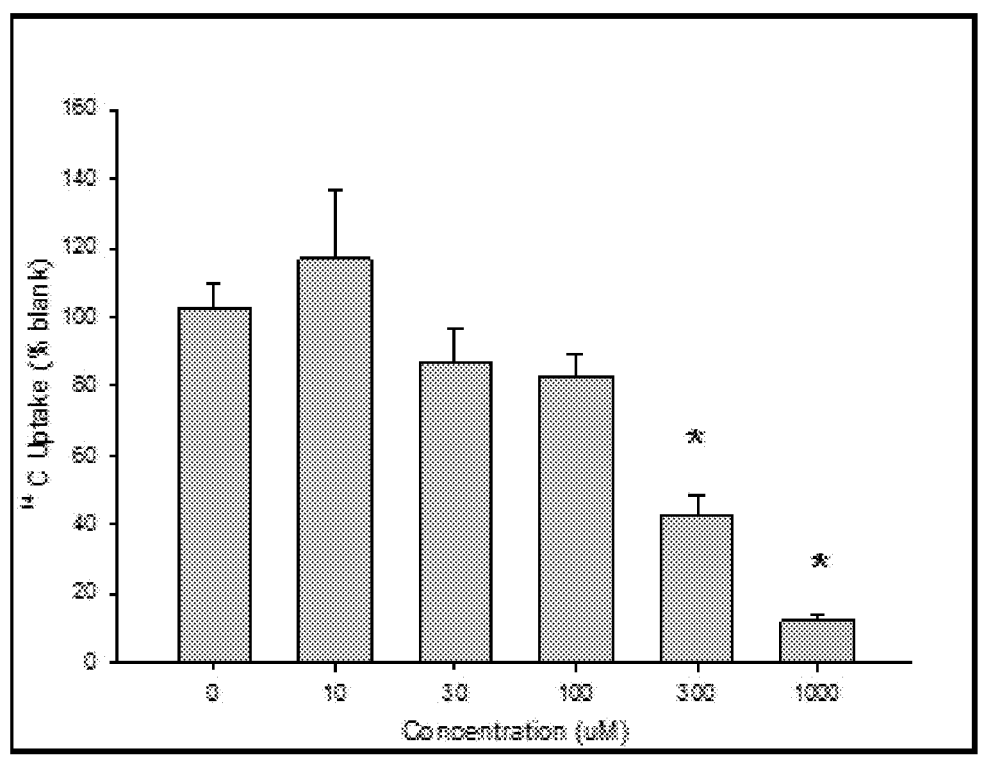
Figure 21C:
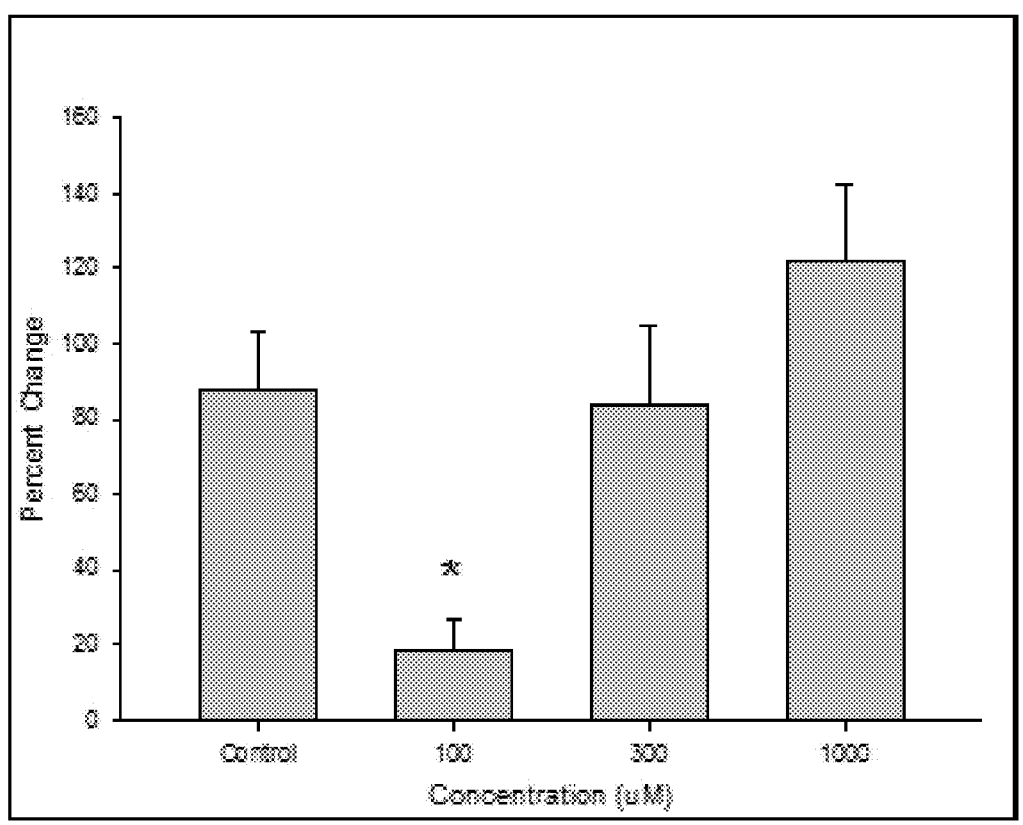
Figure 22A:
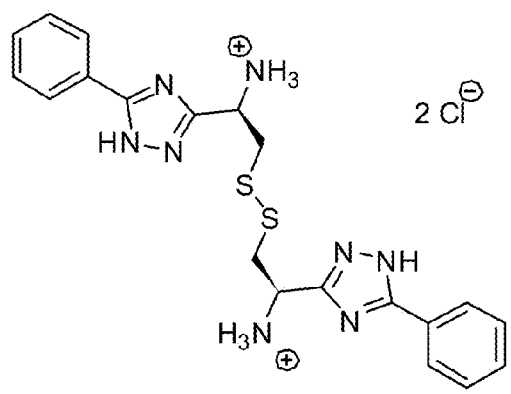
FIG. 22 shows (A) the chemical structure of compound MWL 220 (HCl salt), (B) a bar graph illustrating $C^{14}$ uptake test results for compound MWL 220, and (C) a bar graph illustrating glutamate percent change test results for compound MWL 220.
Figure 22B:
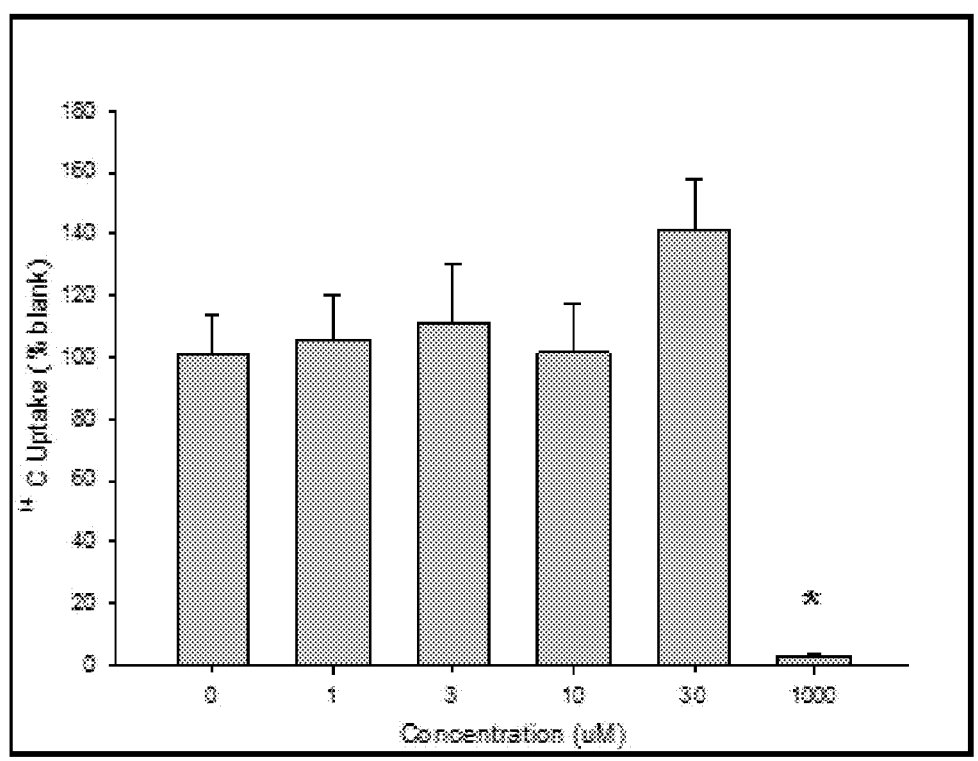
Figure 22C:
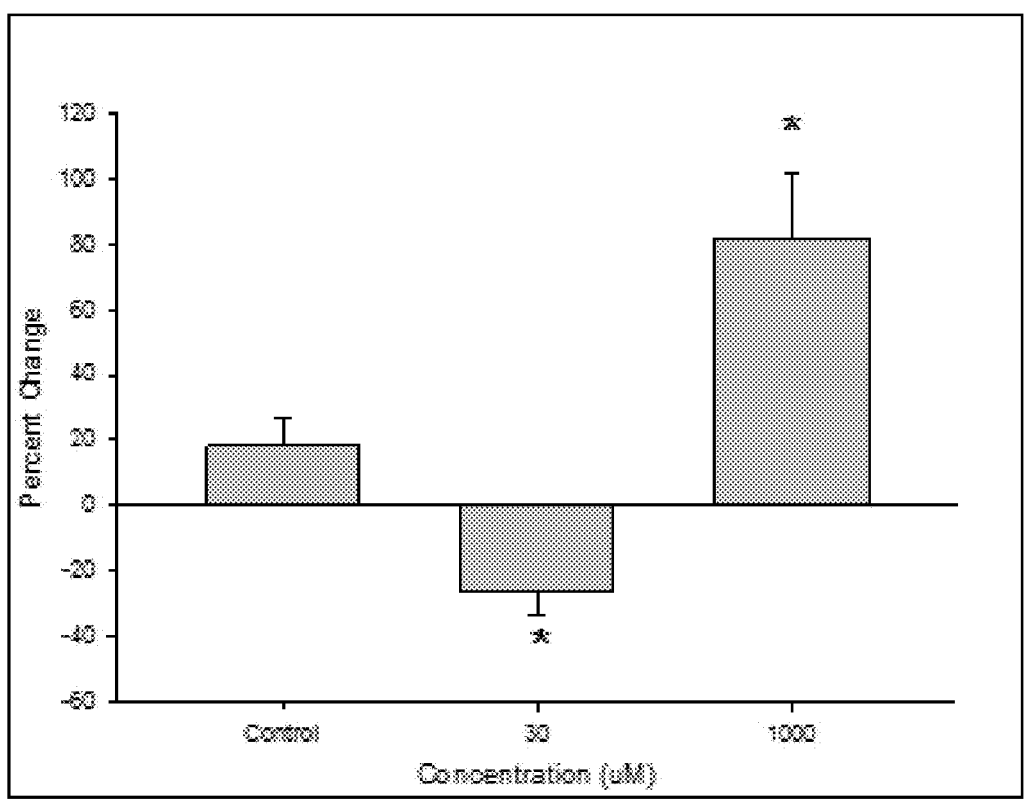
Figure 23A:
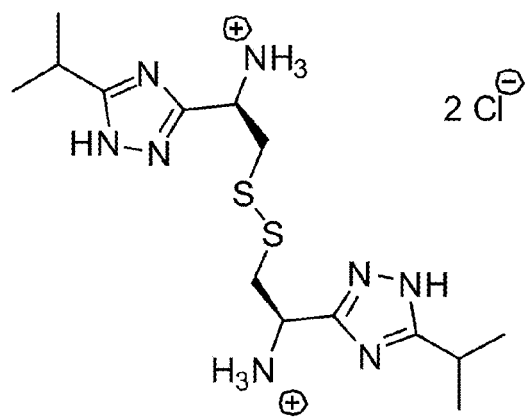
FIG. 23 shows (A) the chemical structure of compound MWL 236 (HCl salt), (B) a bar graph illustrating $C^{14}$ uptake test results for compound MWL 236, and (C) a bar graph illustrating glutamate percent change test results for compound MWL 236.
Figure 23B:
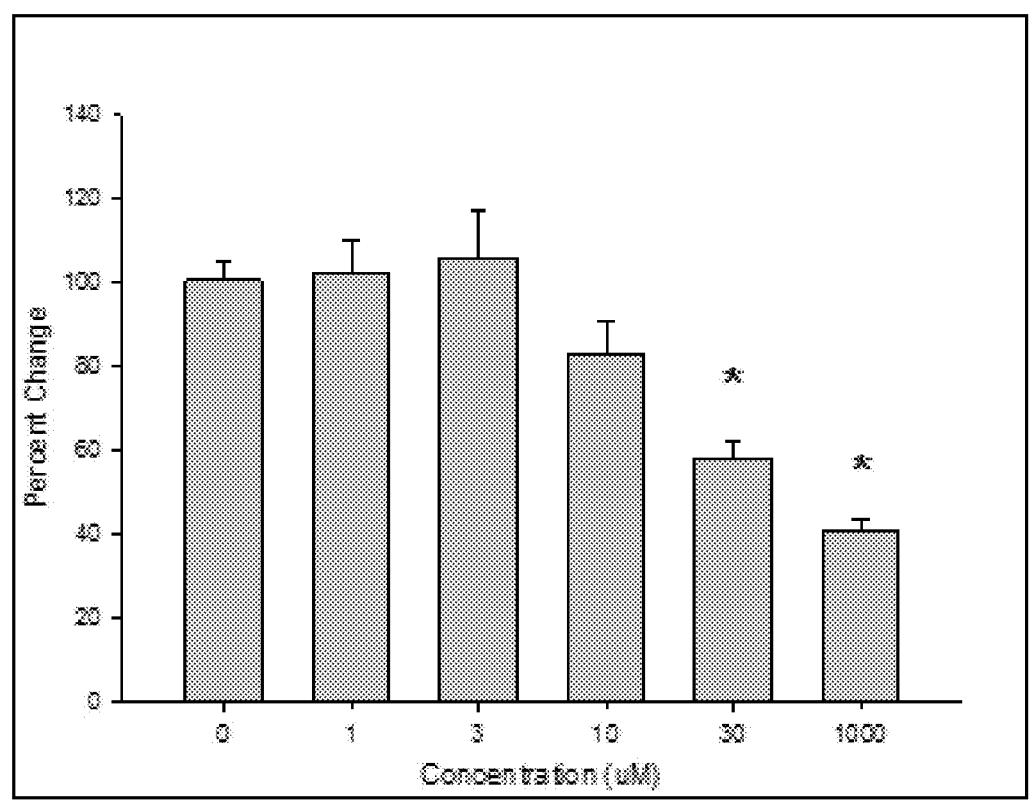
Figure 23C:
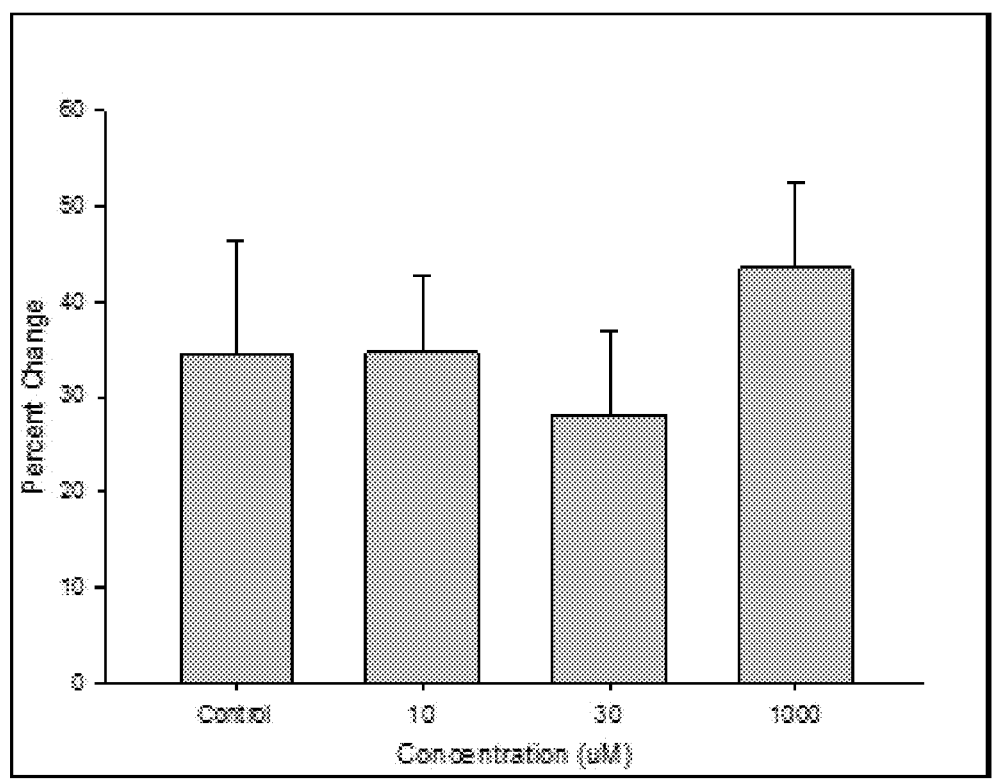
Figure 24A:
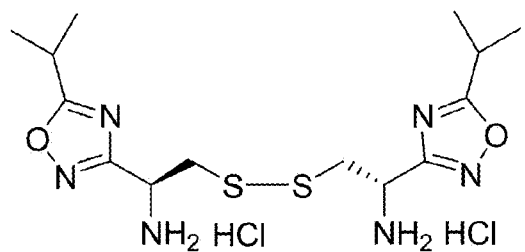
FIG. 24 shows (A) the chemical structure of compound WYME SSI P (HCl salt), also designated as compound Pro-039, (B) a bar graph illustrating $C^{14}$ uptake test results for compound WYMW SSI P/Pro-039, (C) a bar graph illustrating glutamate percent change test results for compound WYMW SSI P/Pro-039, (D) a bar graph illustrating Elevated Plus Maze test results for compound WYME SSI P/Pro-039, and (E) a bar graph illustrating startle response inhibition test results for compound WYME SSI P/Pro-039 (#=significant from Pro-039 0 (all)).
Figure 24B:
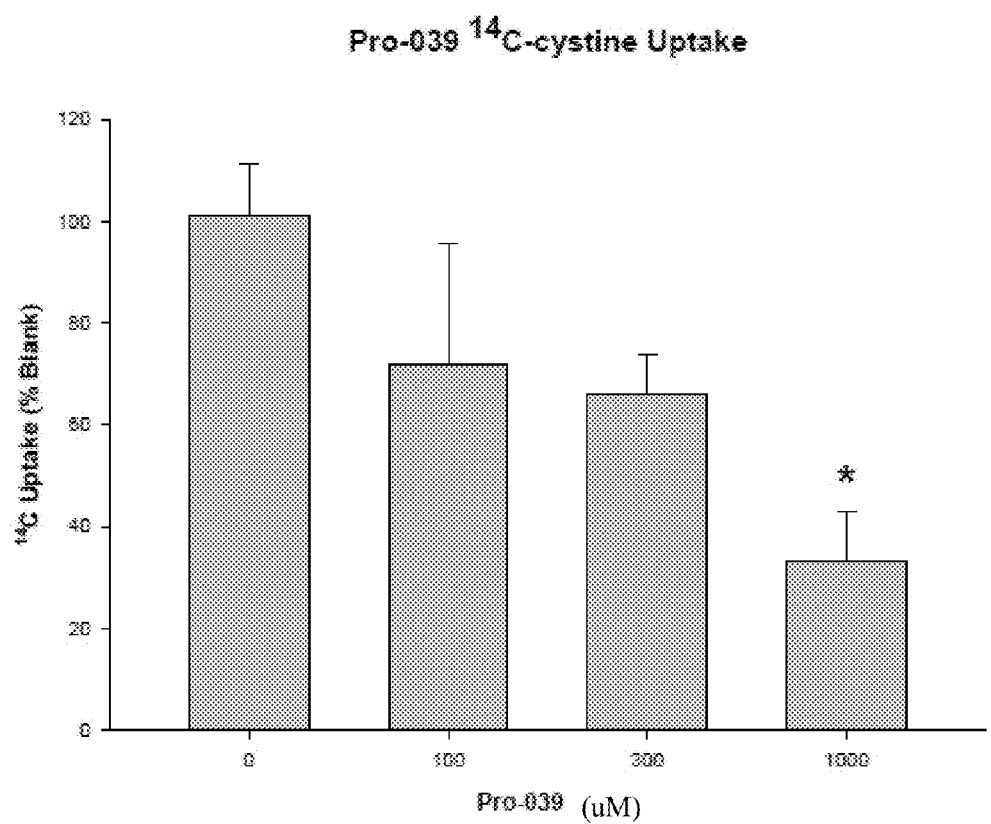
Figure 24C:
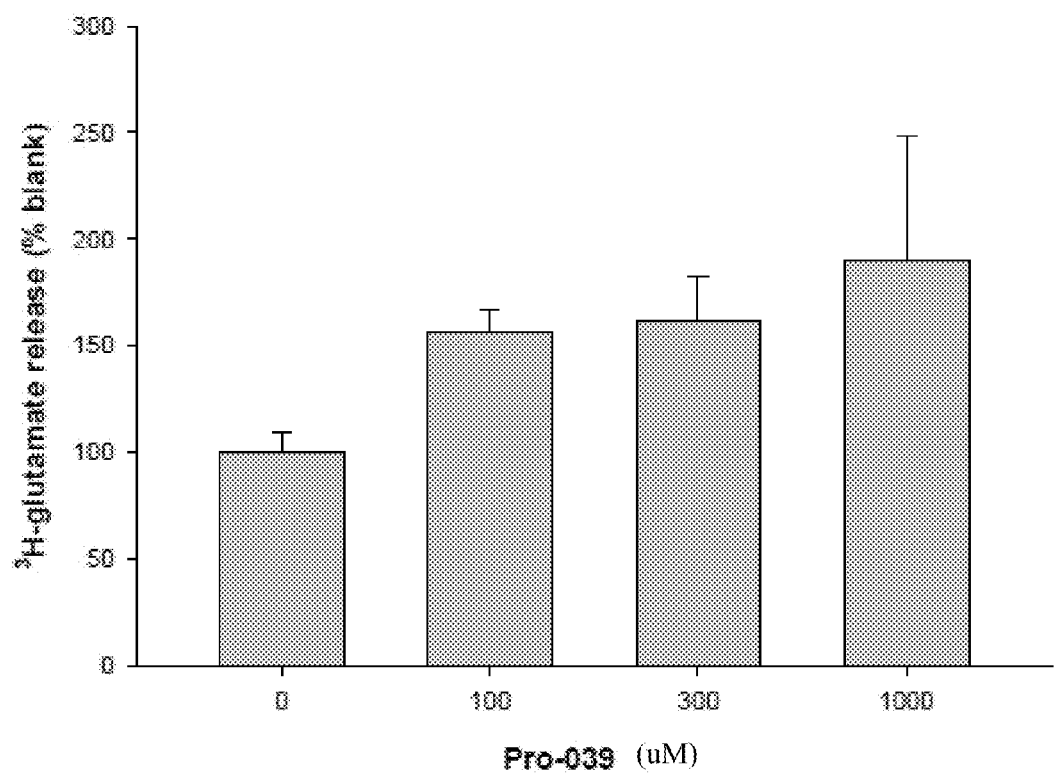
Figure 24D:
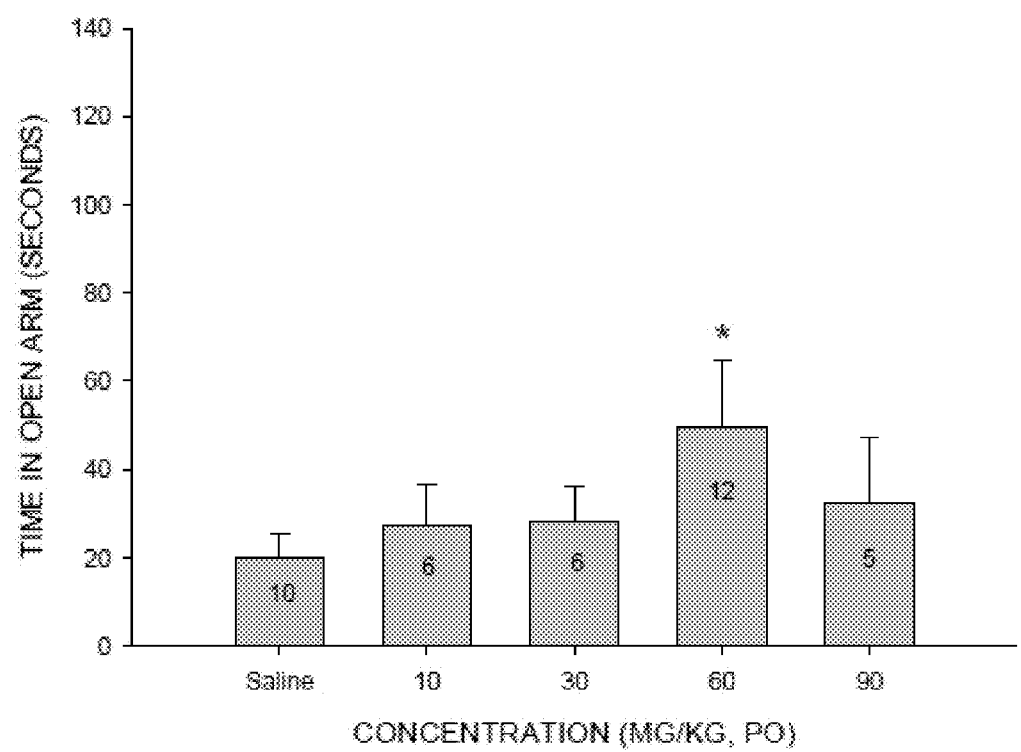
Figure 24E:
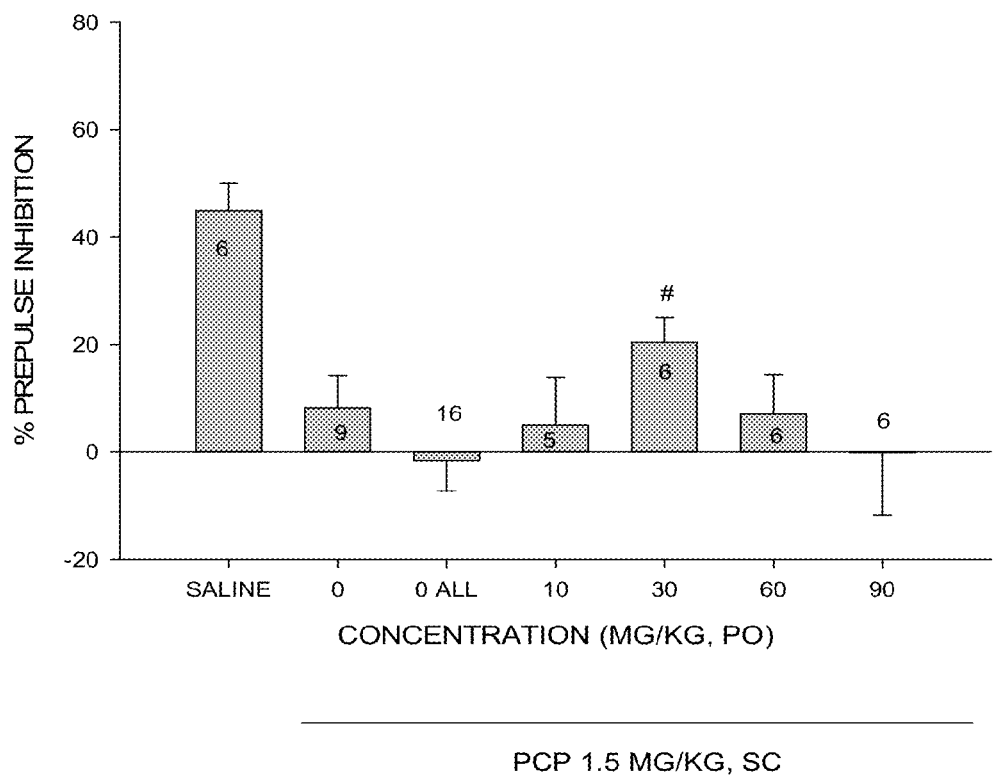
Figure 25A:
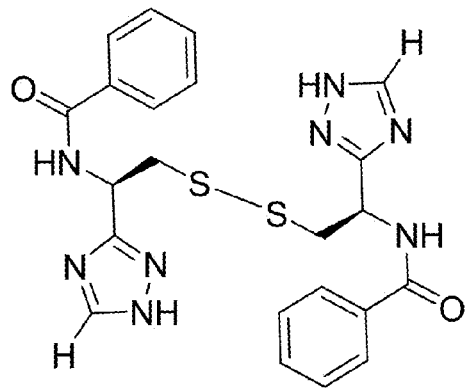
FIG. 25 shows (A) the chemical structure of compound MWL 299, also designated as compound Pro-081, (B) a bar graph illustrating $C^{14}$ uptake test results for compound MWL 299/Pro-081, (C) a bar graph illustrating glutamate percent change test results for compound MWL 299/Pro-081 (X axis is Pro-081 concentration in uM), (D) a bar graph illustrating Elevated Plus Maze test results for compound MWL 299/Pro-081, and (E) a bar graph illustrating startle response inhibition test results for compound MWL 299/Pro-081.
Figure 25B:
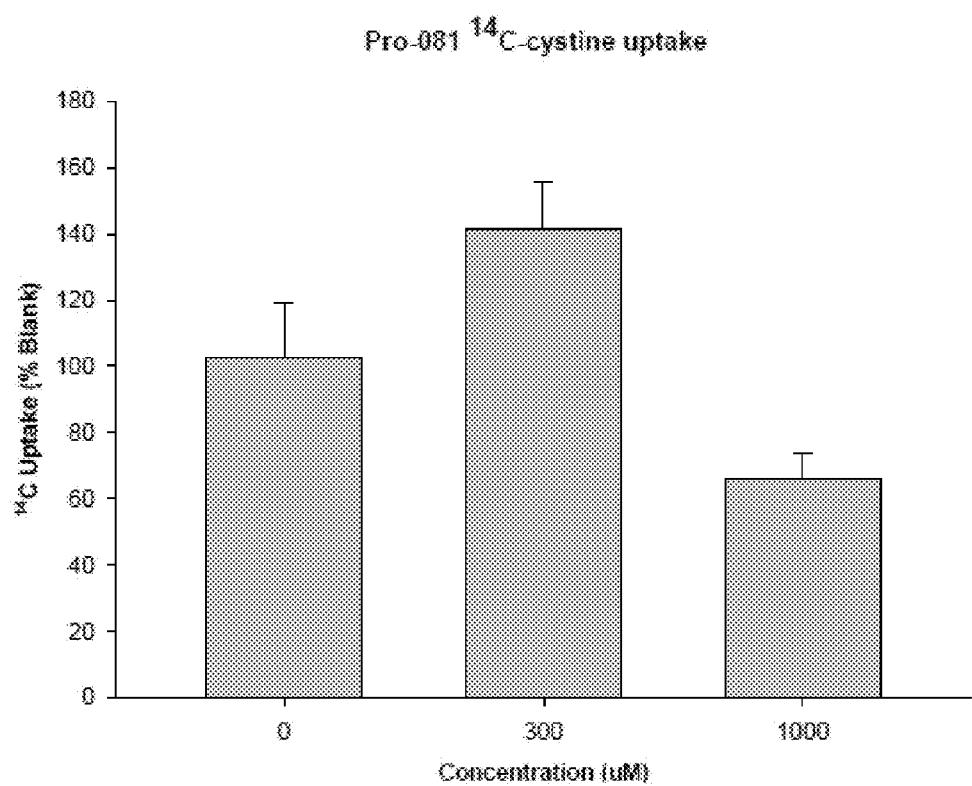
Figure 25C:
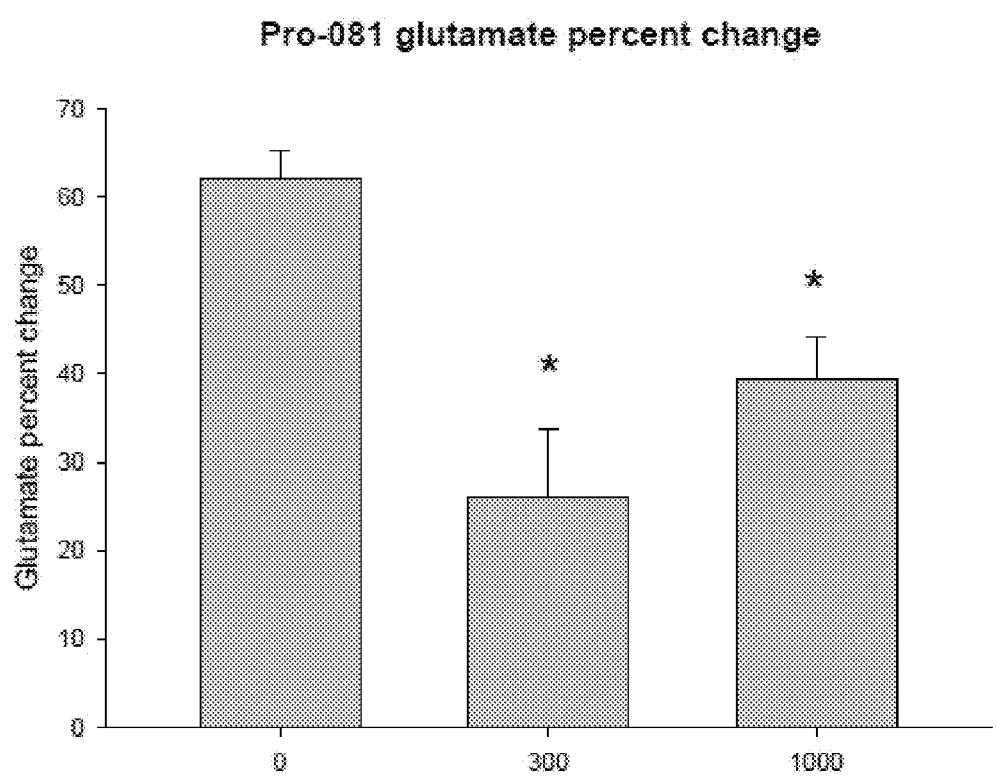
Figure 25D:
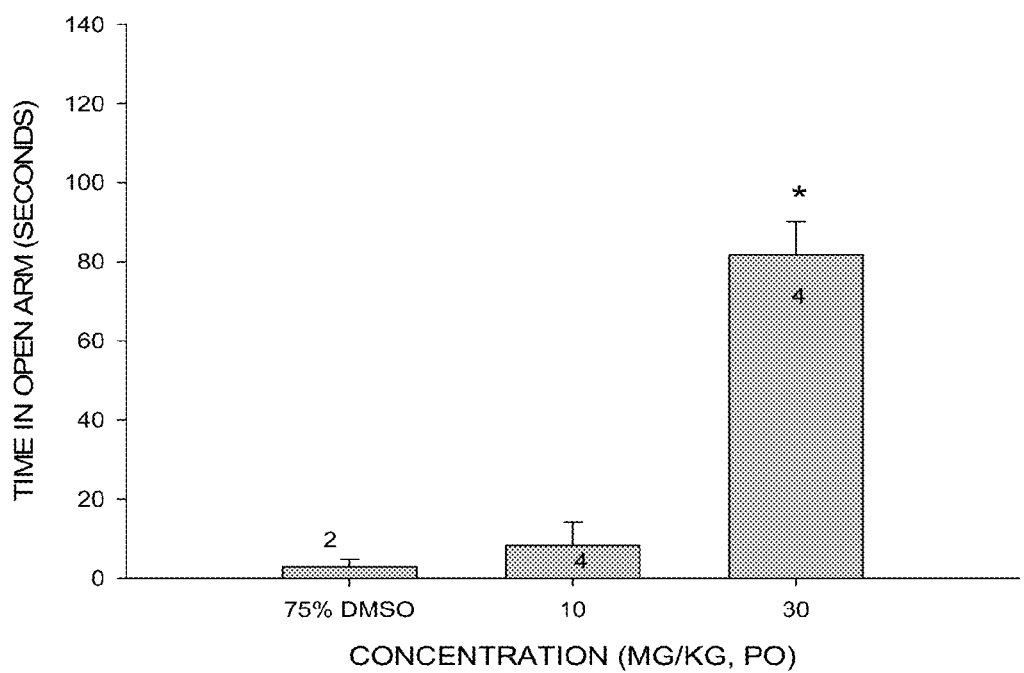
Figure 25E:
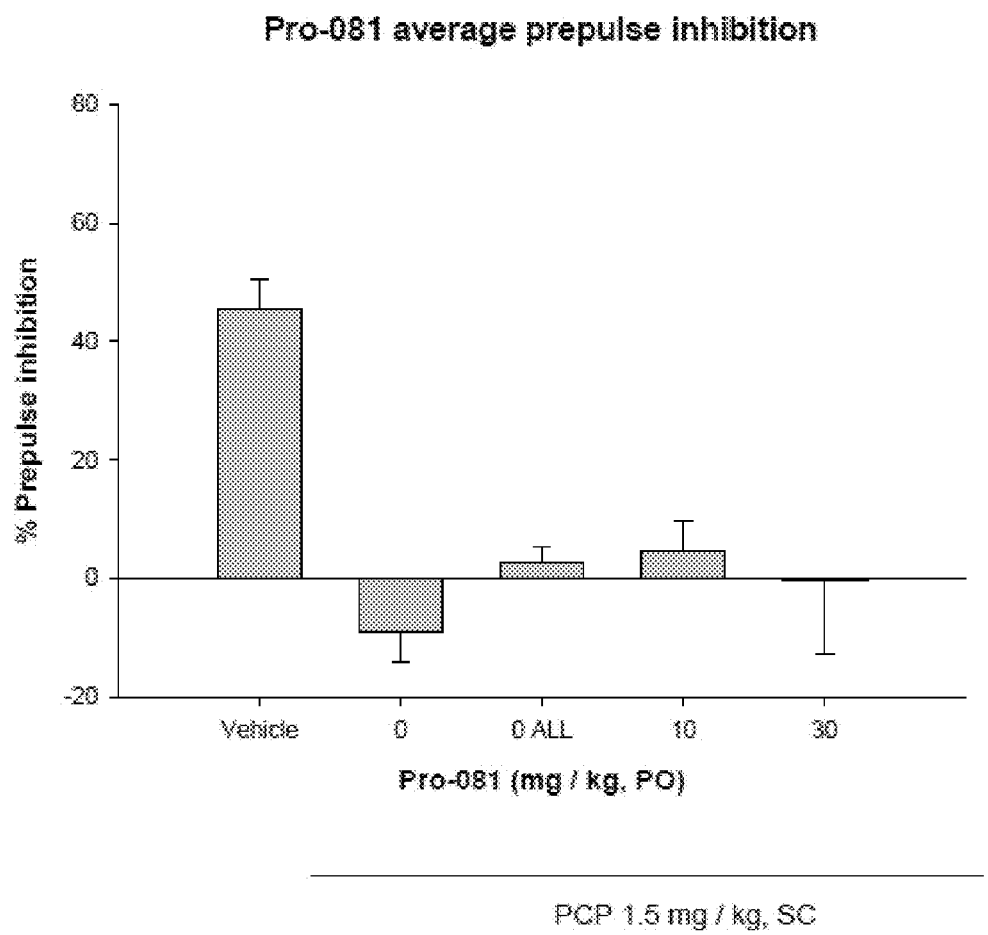

FIG. 18 shows the chemical structure of compound MWL 283 (HCl salt) (A), also designated as compound Pro-090, a bar graph illustrating $C^{14}$ uptake test results for compound MWL 283/Pro-090 (B), and a bar graph illustrating glutamate percent change test results for compound MWL 283/Pro-090 (C). FIG. 19 shows the chemical structure of compound MWL 235 (HCl salt) (A), a bar graph illustrating $C^{14}$ uptake test results for compound MWL 299 (B), and a bar graph illustrating glutamate percent change test results for compound MWL 299 (C). FIG. 20 shows the chemical structure of compound MWL 309 (A), a bar graph illustrating $C^{14}$ uptake test results for compound MWL 309 (B), and a bar graph illustrating glutamate percent change test results for compound MWL 309 (C). FIG. 21 shows the chemical structure of compound MWL 284 (A), a bar graph illustrating $C^{14}$ uptake test results for compound MWL 284 (B), and a bar graph illustrating glutamate percent change test results for compound MWL 284 (C). FIG. 22 shows the chemical structure of compound MWL 220 (HCl salt) (A), a bar graph illustrating $C^{14}$ uptake test results for compound MWL 220 (B), and a bar graph illustrating glutamate percent change test results for compound MWL 220 (C). FIG. 23 shows the chemical structure of compound MWL 236 (HCl salt) (A), a bar graph illustrating $C^{14}$ uptake test results for compound MWL 236 (B), and a bar graph illustrating glutamate percent change test results for compound MWL 236 (C).

Figure 27A:
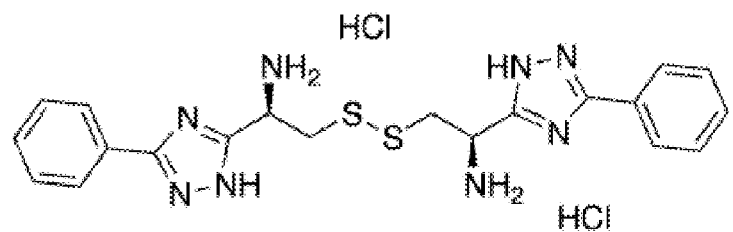
FIG. 27 shows (A) the chemical structure of compound Pro-072, (B) a bar graph illustrating $C^{14}$ uptake test results for compound Pro-072 (HCl salt), and (C) a bar graph illustrating glutamate percent change test results for compound Pro-072 (X axis is Pro-072 concentration in uM).
Figure 27B:
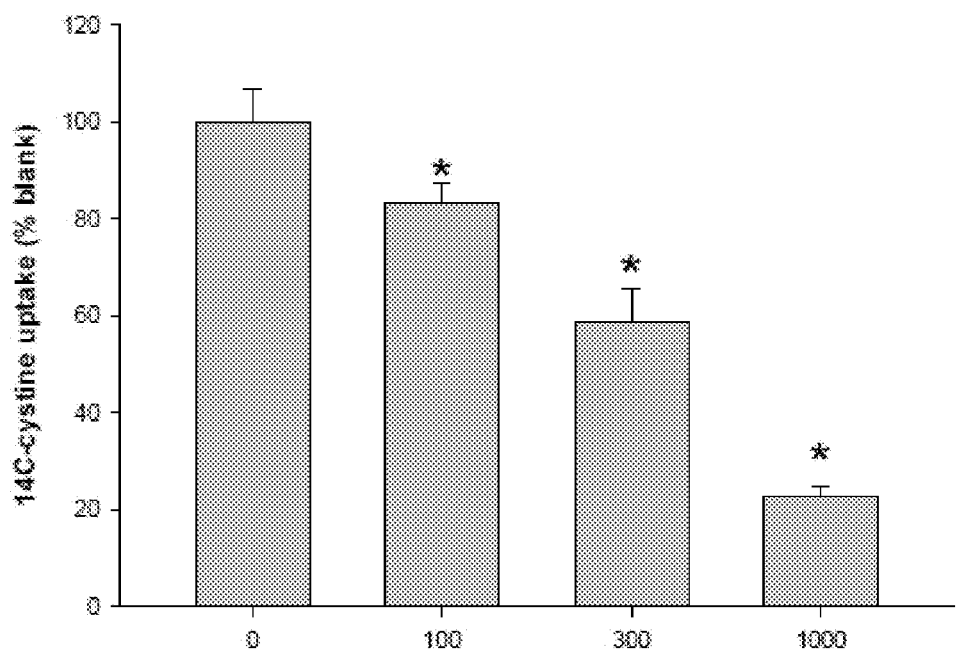
Figure 27C:
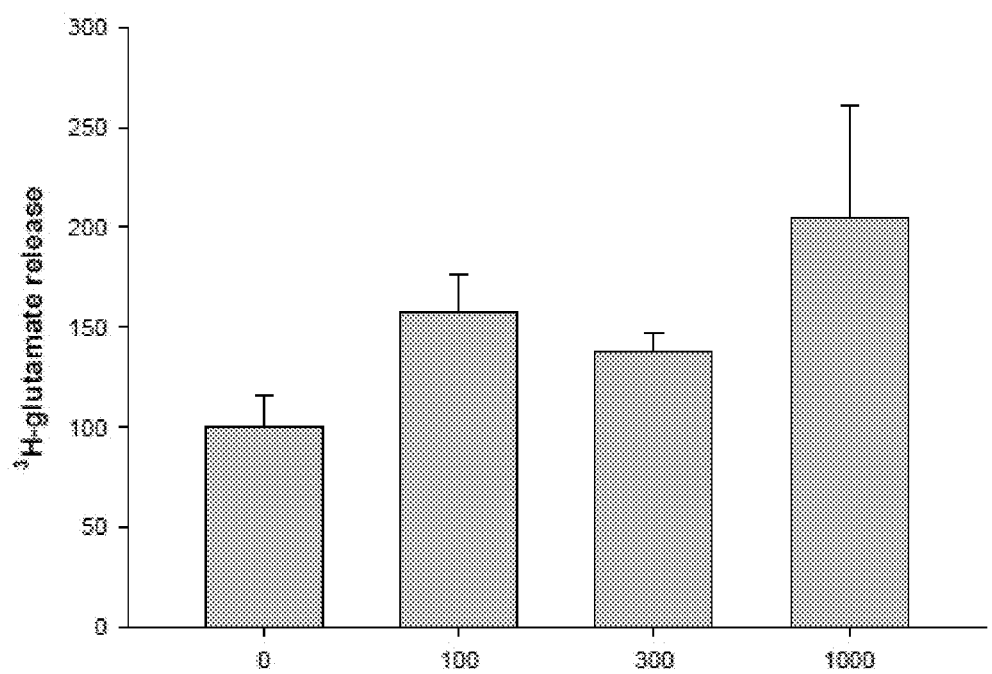
Figure 28A:
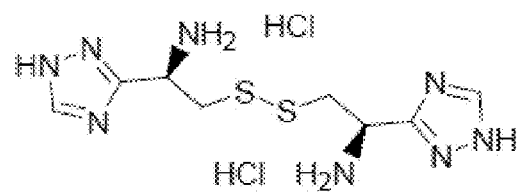
FIG. 28 shows (A) the chemical structure of compound Pro-078 (HCl salt), (B) a bar graph illustrating $C^{14}$ uptake test results for compound Pro-078, (C) a bar graph illustrating glutamate percent change test results for compound Pro-078, (D) a bar graph illustrating Elevated Plus Maze test results for compound Pro-078 (X axis is Pro-078 concentration in mg/kg, PO), and (E) a bar graph illustrating startle response inhibition test results for compound Pro-078 (#=significant from Pro-078 0 (all)).
Figure 28B:
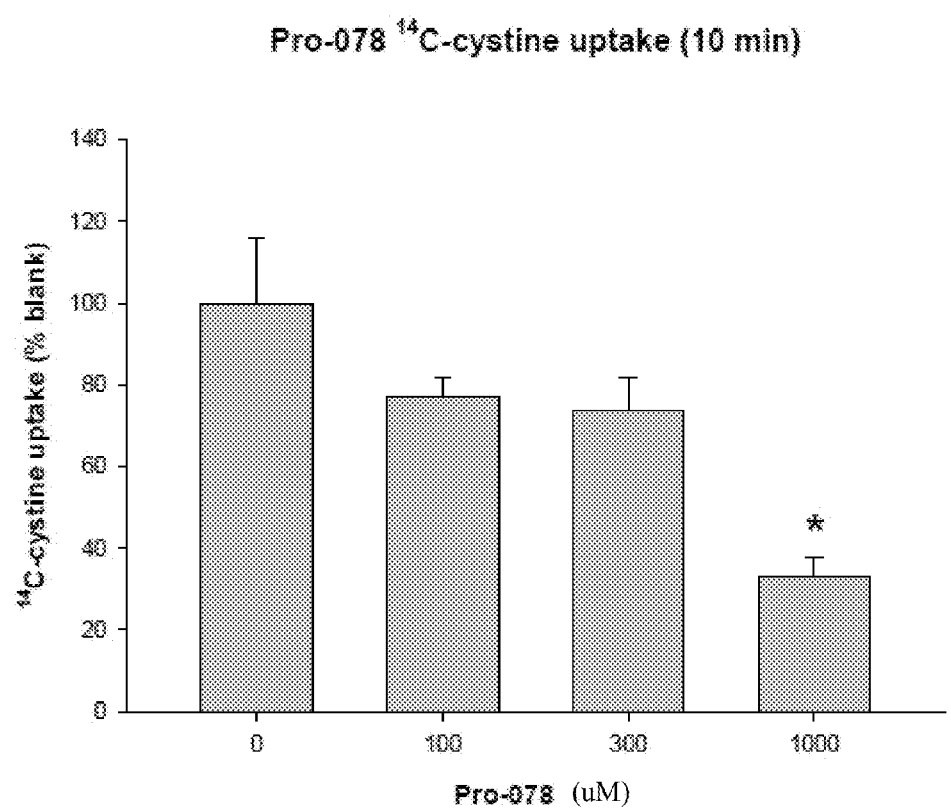
Figure 28C:
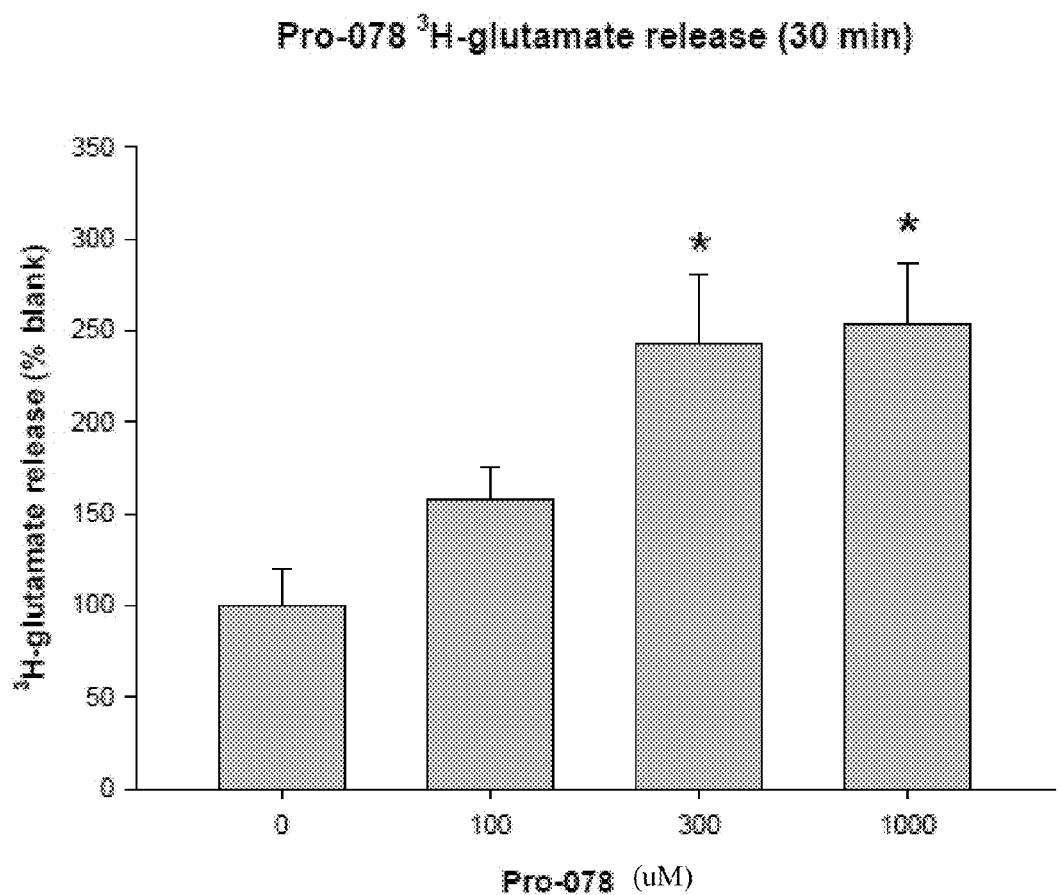
Figure 28D:
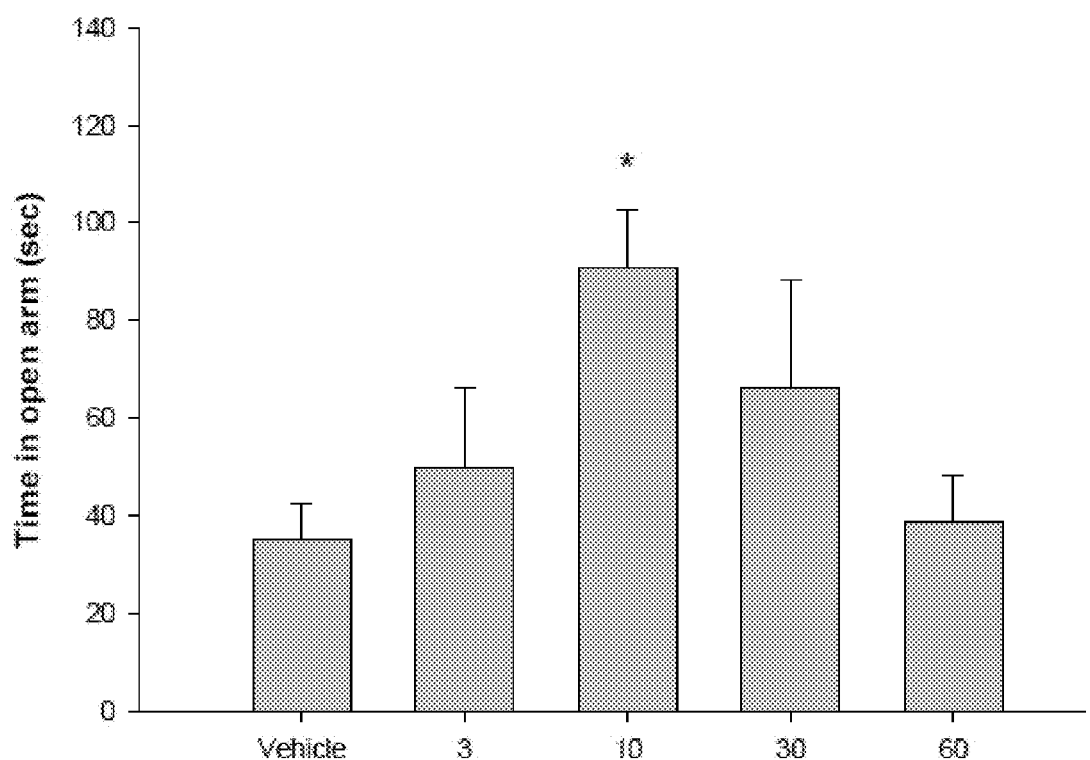
Figure 28E:
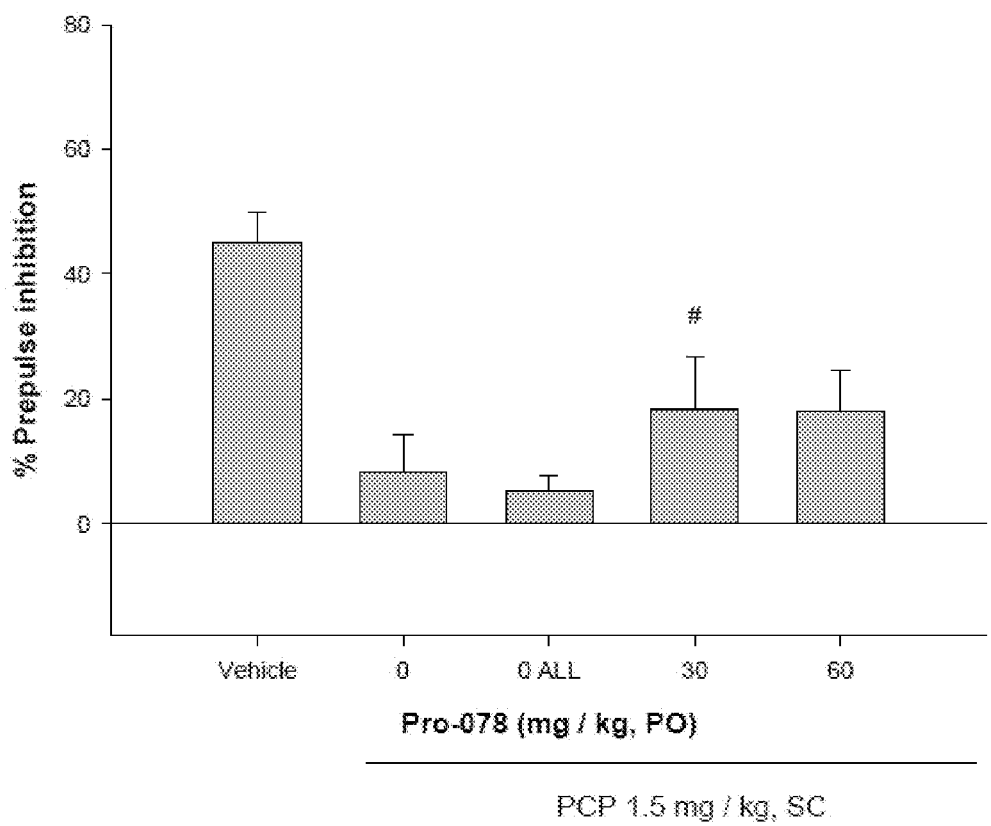
Figure 29A:
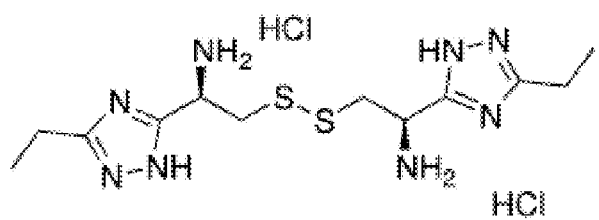
FIG. 29 shows (A) the chemical structure of compound Pro-076 (HCl salt), (B) a bar graph illustrating $C^{14}$ uptake test results for compound Pro-076 (X axis is Pro-076 concentration in uM), and (C) a bar graph illustrating Elevated Plus Maze test results for compound Pro-076.
Figure 29B:
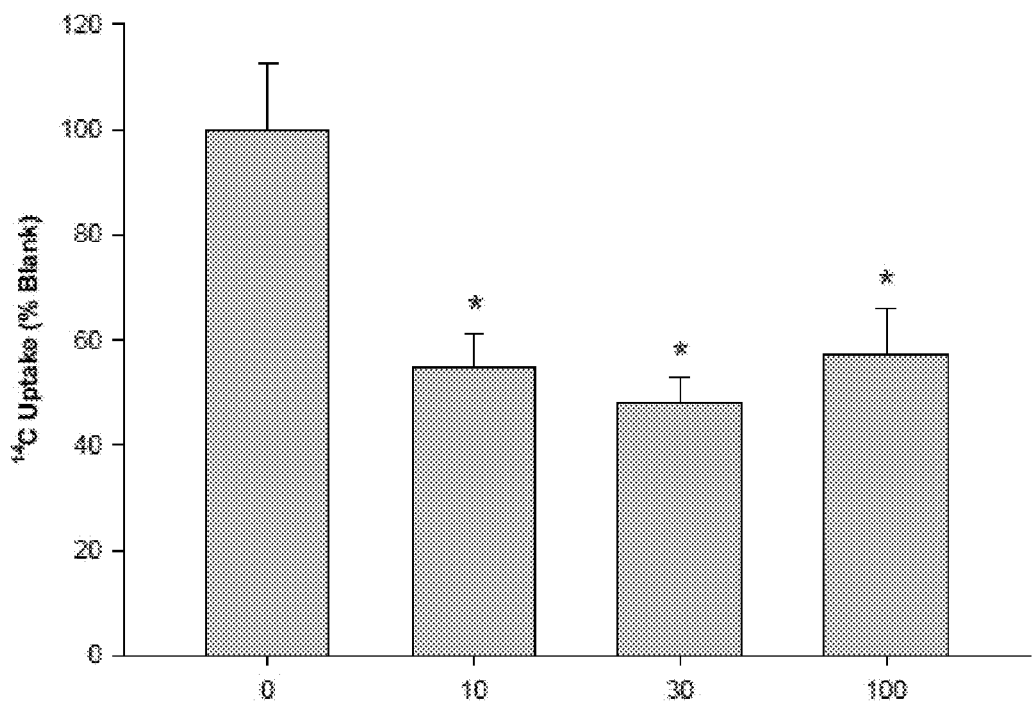
Figure 29C:
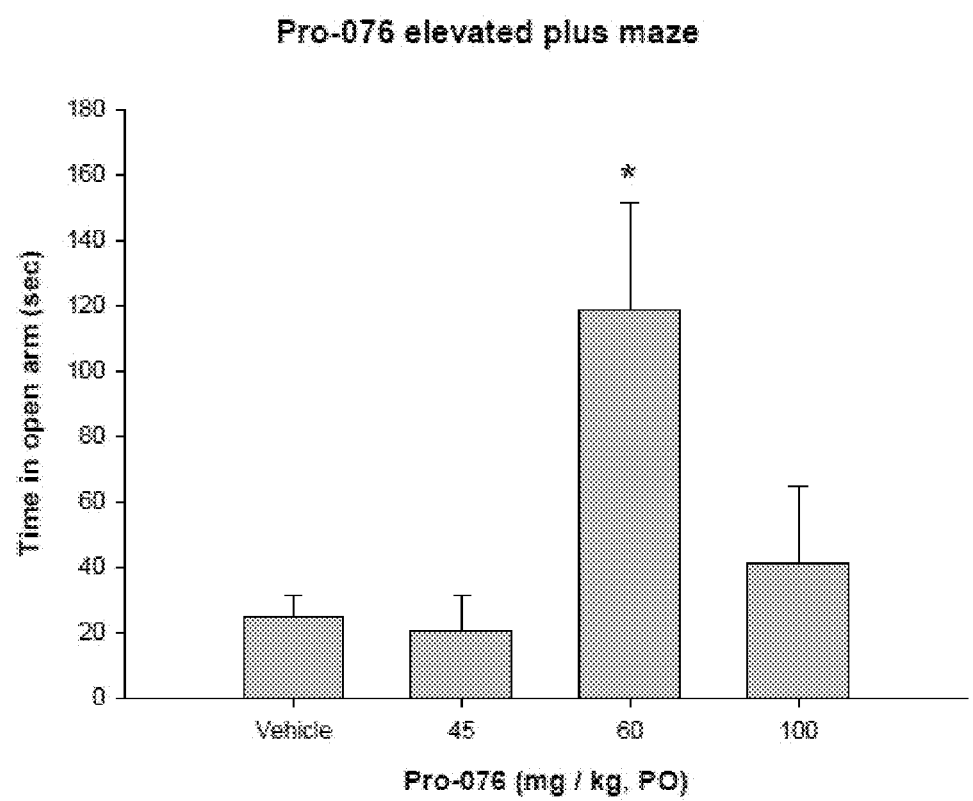
Figure 30A:
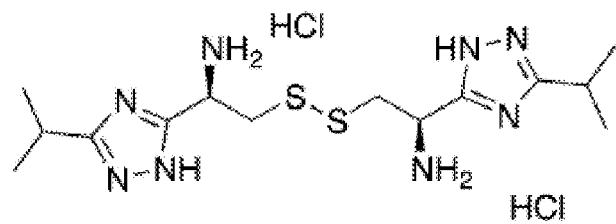
FIG. 30 shows (A) the chemical structure of compound Pro-074 (HCl salt), (B) a bar graph illustrating $C^{14}$ uptake test results for compound Pro-074 (X axis is Pro-074 concentration in uM), and (C) a bar graph illustrating glutamate percent change test results for compound Pro-074 (X axis is Pro-074 concentration in uM).
Figure 30B:
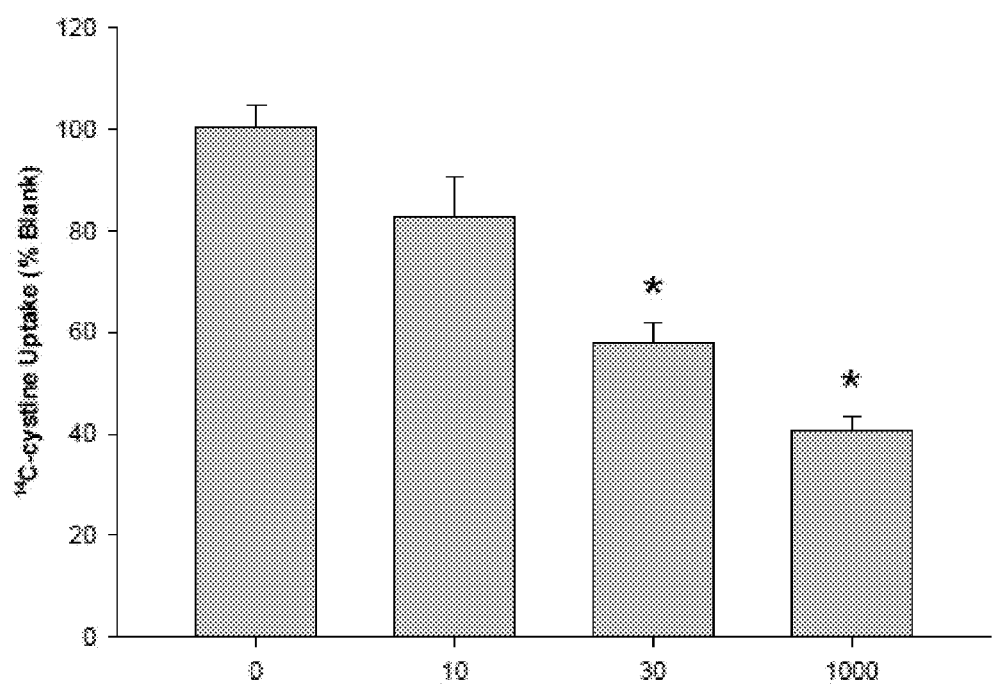
Figure 30C:
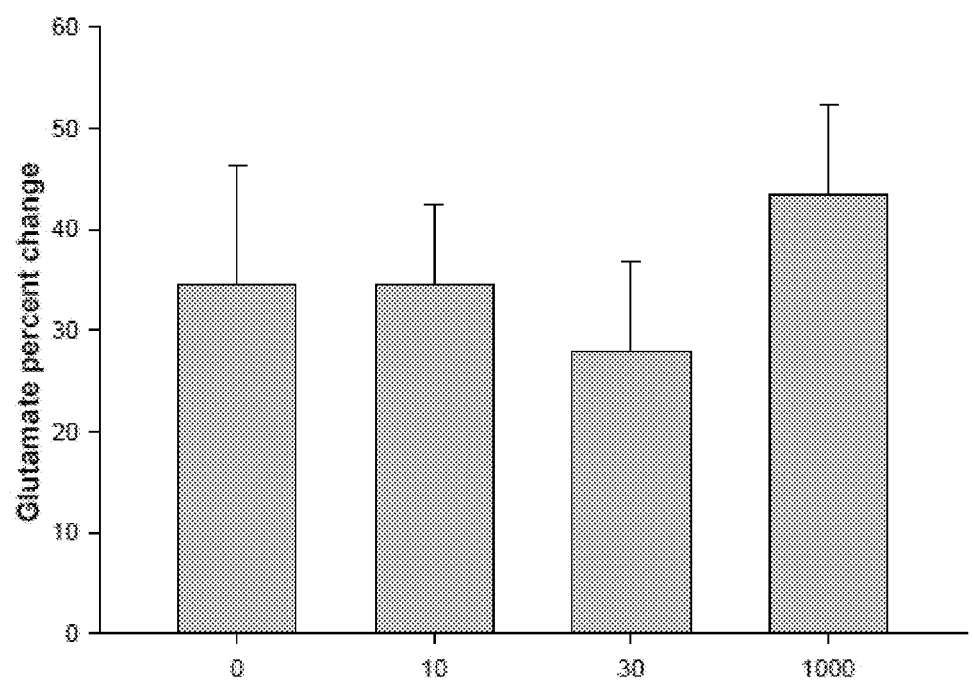
Figure 31A:
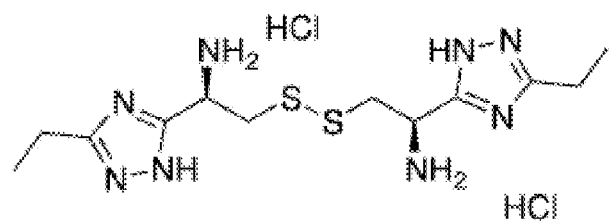
FIG. 31 shows (A) the chemical structure of compound Pro-076 (HCl salt), (B) a bar graph illustrating $C^{14}$ uptake test results for compound Pro-076, (C) a bar graph illustrating glutamate percent change test results for compound Pro-076, and (D) a bar graph illustrating Elevated Plus Maze test results for compound Pro-076.
Figure 31B:
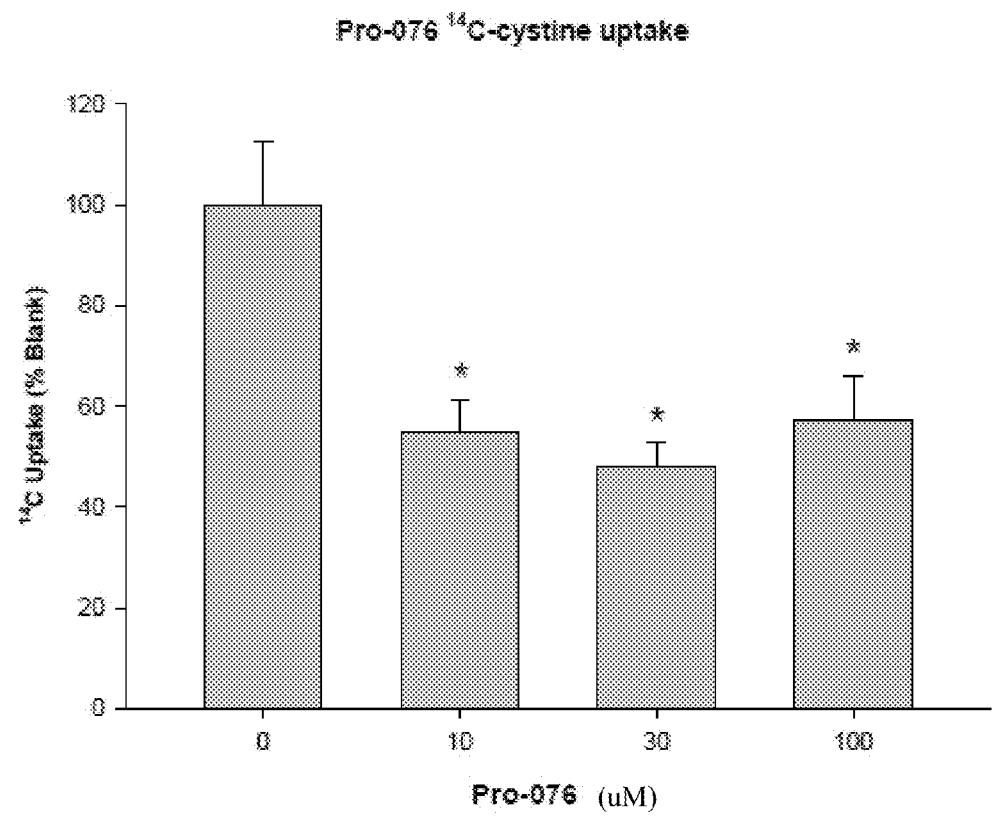
Figure 31C:
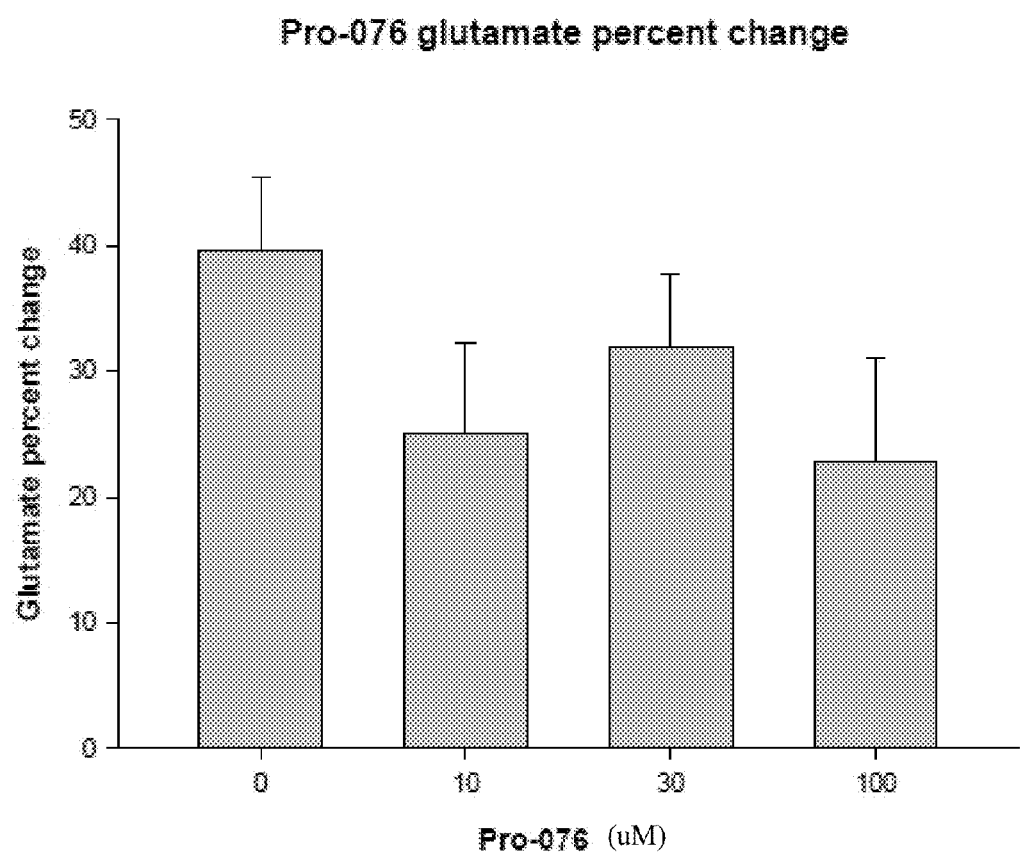
Figure 31D:
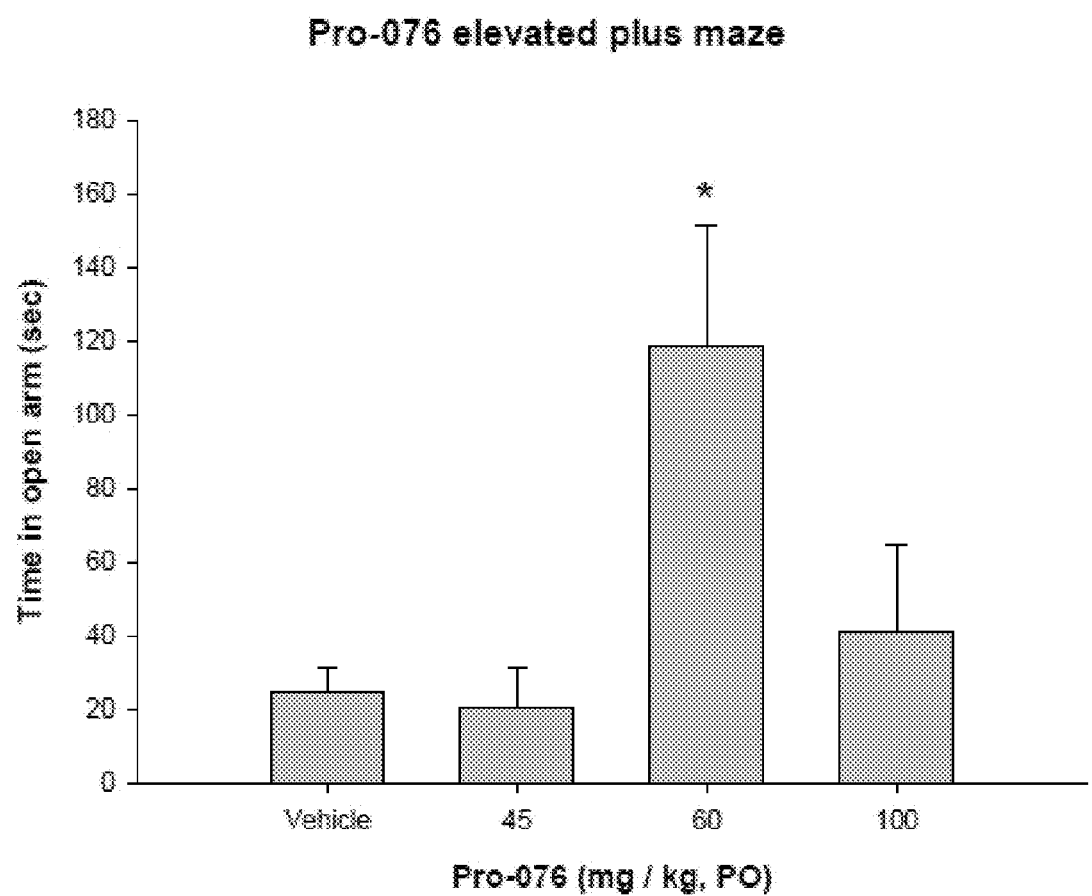

FIG. 24 shows the chemical structure of compound WYME SSI P (HCl salt), also designated as compound Pro-039 (A), a bar graph illustrating $C^{14}$ uptake test results for compound WYMW SSI P/Pro-039 (B), and a bar graph illustrating glutamate percent change test results for compound WYMW SSI P/Pro-039 (C). FIG. 25 shows the chemical structure of compound MWL 299, also designated as compound Pro-081 (A), a bar graph illustrating $C^{14}$ uptake test results for compound MWL 299/Pro-081 (B), and a bar graph illustrating glutamate percent change test results for compound MWL 299/Pro-081 (X axis is Pro-081 concentration in uM) (C). FIG. 27 shows the chemical structure of compound Pro-072 (A), a bar graph illustrating $C^{14}$ uptake test results for compound Pro-072 (B), and a bar graph illustrating glutamate percent change test results for compound Pro-072 (X axis is Pro-072 concentration in uM) (C). FIG. 28 shows the chemical structure of compound Pro-078 (HCl salt) (A), a bar graph illustrating $C^{14}$ uptake test results for compound Pro-078 (B), and a bar graph illustrating glutamate percent change test results for compound Pro-078 (C). FIG. 29 shows the chemical structure of compound Pro-076 (HCl salt) (A), and a bar graph illustrating $C^{14}$ uptake test results for compound Pro-076 (X axis is Pro-076 concentration in uM) (B). FIG. 30 shows the chemical structure of compound Pro-074 (HCl salt) (A), a bar graph illustrating $C^{14}$ uptake test results for compound Pro-074 (X axis is Pro-074 concentration in uM) (B), and a bar graph illustrating glutamate percent change test results for compound Pro-074 (X axis is Pro-074 concentration in uM) (C). FIG. 31 shows the chemical structure of compound Pro-076 (HCl salt) (A), a bar graph illustrating $C^{14}$ uptake test results for compound Pro-076 (B), and a bar graph illustrating glutamate percent change test results for compound Pro-076 (C).

As seen in the data disclosed in these figures, a significant increase in $^3H$ glutamate release compared to control, and/or a significant decrease in $^{14}C$-cystine uptake demonstrate the ability of the tested compound to successfully engage system xc- in this in vitro culture system. The behavioral model experimental data reported in the next two examples provide illustrations of the in vivo conversion and efficacy of these compounds.

Example 26

Elevated Plus Maze Experiments

The goal of these experiments was to demonstrate the ability of the test compounds to penetrate the CNS. In an exemplary experiment, rats are tested in a standard elevation plus maze. Testing occurs in a dimly illuminated room using only two lights mounted over the maze. Animals are allowed to habituate to the room for at least one hour prior to treatment.

One prior to testing, rats receive a test compound (0-100 mg/kg, P.O.). For testing, the rat is placed in the elevated plus maze for five minutes, alternating the starting position between facing an open arm and facing a closed arm. The session is recorded and an observer blind to treatment records the number of explorations, entries and time spent in the open arm. Explorations are defined as the rat placing two feet into an open arm without fully entering said arm. Entries are defined as the rat placing all four feet in an open arm. Time of entry in the open arm is recorded from the time the rat placed four feet in the open arm until two of the rats' feet entered the open square.

Figure 26A:
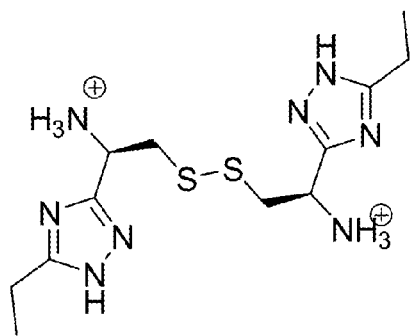
FIG. 26 shows (A) the chemical structure of compound MWL 235, and (B) a bar graph illustrating Elevated Plus Maze test results for compound MWL 235.
Figure 26B:
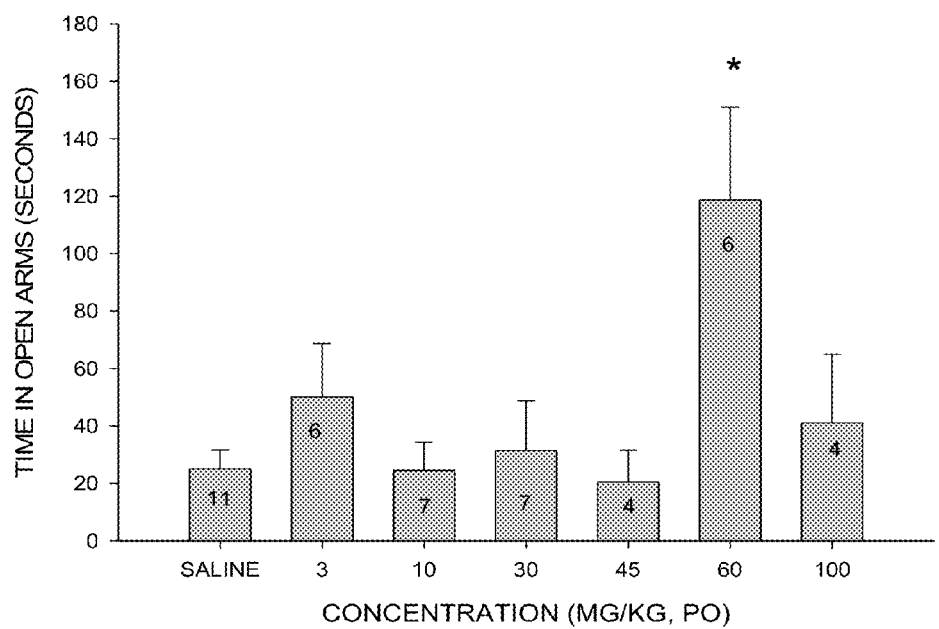

FIG. 24 shows the chemical structure of compound WYME SSI P (HCl salt), also designated as compound Pro-039 (A), and a bar graph illustrating Elevated Plus Maze test results for compound WYME SSI P/Pro-039 (D). FIG. 25 shows the chemical structure of compound MWL 299, also designated as compound Pro-081 (A), and a bar graph illustrating Elevated Plus Maze test results for compound MWL 299/Pro-081 (D). FIG. 26 shows the chemical structure of compound MWL 235 (A), and a bar graph illustrating Elevated Plus Maze test results for compound MWL 235 (B). FIG. 28 shows the chemical structure of compound Pro-078 (HCl salt) (A), and a bar graph illustrating Elevated Plus Maze test results for compound Pro-078 (X axis is Pro-078 concentration in mg/kg, PO) (D). FIG. 29 shows the chemical structure of compound Pro-076 (HCl salt) (A), and a bar graph illustrating Elevated Plus Maze test results for compound Pro-076 (C). FIG. 31 shows the chemical structure of compound Pro-076 (HCl salt) (A), and a bar graph illustrating Elevated Plus Maze test results for compound Pro-076 (D).

As seen in the data disclosed in these figures, a significant increase in time spent in the open arm for rats treated with the test compounds, as compared to a control, demonstrates that the compounds exhibit an anxiolytic effect in the elevated plus maze model.

Example 27

Pre-Pulse Inhibition Experiments

The goal of these experiments was to demonstrate the efficacy of the test compounds in a predictive animal model of schizophrenia. In an exemplary experiment, rats are placed on a platform in a sound attenuating chamber (10.875"×14"× 19.5", Hamilton Kinder, CA) that rests on a motion sensing plate. During all sessions, background noise is held constant at 60 dB. A matching session is conducted to determine the magnitude of the average startle response for each rat. This session consists of a five minute habituation period followed by twenty trials.

Seventeen of these trials involve the presentation of a single auditory stimulus (pulse stimulus; 50 dB above the background noise), and in three of these trials, a pre-pulse stimulus (12 dB above background) is presented 100 ms before the pulse auditory stimulus.

Rats are then assigned to various treatment groups so that the magnitude of the startle response is equivalent across all groups. Two days later, a testing session is conducted to assess sensorimotor gating. One hour prior to testing, rats receive a test compound (0-100 mg/kg, P.O.), and 50 minutes later, acute PCP (0-1.5 mg/kg, SC).

The testing session consists of a five minute habituation period, after which rats received 58 discrete trials: 26 trials during which the pulse stimulus (50 dB above background) was presented alone, eight trials each in which the pulse stimulus was preceded by a pre-pulse stimulus (5, 10, or 15 dB above background), and eight background trials with no pulse (no stimulus; background noise only).

The first six pulse alone trials are not included in the average startle stimulus, to achieve a relatively stable level of startle reactivity. The percent of pre-pulse inhibition is determined as 100–(average pre-pulse startle response/average startle stimulus alone)*100.

FIG. 24 shows the chemical structure of compound WYME SSI P (HCl salt), also designated as compound Pro-039 (A), and (E) a bar graph illustrating startle response inhibition test results for compound WYME SSI P/Pro-039 (#=significant from Pro-039 0 (all)). FIG. 25 shows the chemical structure of compound MWL 299, also designated as compound Pro-081 (A), and (E) a bar graph illustrating startle response inhibition test results for compound MWL 299/Pro-081. FIG. 28 shows the chemical structure of compound Pro-078 (HCl salt) (A), and (E) a bar graph illustrating startle response inhibition test results for compound Pro-078 (#=significant from Pro-078 0 (all)).

As seen in the data disclosed in these figures, significant increases in pre-pulse inhibition for rats given the test compounds as compared to control groups that received both PCP and vehicle demonstrate that the three compounds tested significantly ameliorate PCP-induced deficit in pre-pulse inhibition.

While this invention has been described in conjunction with the various exemplary embodiments outlined above, various alternatives, modifications, variations, improvements and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. All publications, patents and patent applications cited herein are hereby incorporated by reference in their entirety for all purposes.

REFERENCES

Baker D A, McFarland K, Lake R W, Shen H, Tang X C, Toda S, Kalivas P W (2003). Neuroadaptations in cystine-glutamate exchange underlie cocaine relapse. *Nat Neurosci* 6:743-749.
Breiter H C, Gollub R L, Weisskoff R M, Kennedy D N, Makris N, Berke J D, Goodman J M, Kantor H L, Gastfriend D R, Riorden J P, Mathew R T, Rosen B R, Hyman S E (1997). Acute effects of cocaine on human brain activity and emotion. *Neuron* 19:591-611.
Cornish J L, Kalivas P W (2000). Glutamate transmission in the nucleus accumbens mediates relapse in cocaine addiction. *J Neurosci* 20:RC89.
Fuchs R A, Evans K A, Ledford C C, Parker M P, Case J M, Mehta R H, See RE (2005). The role of the dorsomedial prefrontal cortex, basolateral amygdala, and dorsal hippocampus in contextual reinstatement of cocaine seeking in rats. *Neuropsychopharmacology* 30:296-309.
Kalivas P W, Volkow N D (2005). The neural basis of addiction: a pathology of motivation and choice. *Am J Psychiatry* 162:1403-1413.
Kalivas P W, Volkow N, Seamans J (2005). Unmanageable motivation in addiction: a pathology in prefrontal-accumbens glutamate transmission. *Neuron* 45:647-650.
Kau K S, Madayag A, Mantsch J R, Grier M D, Abdulhameed O, Baker D A (2008). Blunted cystine-glutamate antiporter function in the nucleus accumbens promotes cocaine-induced drug seeking *Neuroscience* 155:530-537.
Madayag A, Lobner D, Kau K S, Mantsch J R, Abdulhameed O, Hearing M, Grier M D, Baker D A (2007). Repeated N-acetylcysteine administration alters plasticity-dependent effects of cocaine. *J Neurosci* 27:13968-13976.
McFarland K, Kalivas P W (2001). The circuitry mediating cocaine-induced reinstatement of drug-seeking behavior. *J Neurosci* 21:8655-8663.
McFarland K, Lapish C C, Kalivas P W (2003). Prefrontal glutamate release into the core of the nucleus accumbens mediates cocaine-induced reinstatement of drug-seeking behavior. *J Neurosci* 23:3531-3537.
McFarland K, Davidge S B, Lapish C C, Kalivas P W (2004). Limbic and motor circuitry underlying footshock-induced reinstatement of cocaine-seeking behavior. *J Neurosci* 24:1551-1560.
Park W K, Bari A A, Jey A R, Anderson S M, Spealman R D, Rowlett J K, Pierce R C (2002). Cocaine administered into the medial prefrontal cortex reinstates cocaine-seeking behavior by increasing AMPA receptor-mediated glutamate transmission in the nucleus accumbens. *J Neurosci* 22:2916-2925.
Peters J, Kalivas P W (2006). The group II metabotropic glutamate receptor agonist, LY379268, inhibits both cocaine- and food-seeking behavior in rats. *Psychopharmacology (Berl)* 186:143-149.
Schmidt H D, Anderson S M, Famous K R, Kumaresan V, Pierce R C (2005). Anatomy and pharmacology of cocaine priming-induced reinstatement of drug seeking *Eur J Pharmacol* 526:65-76.
Volkow N D, Wang G J, Fowler J S, Hitzemann R, Angrist B, Gatley S J, Logan J, Ding Y S, Pappas N (1999). Association of methylphenidate-induced craving with changes in right striato-orbitofrontal metabolism in cocaine abusers: implications in addiction. *Am J Psychiatry* 156:19-26.
Volkow N D, Wang G J, Ma Y, Fowler J S, Wong C, Ding Y S, Hitzemann R, Swanson J M, Kalivas P (2005). Activation of orbital and medial prefrontal cortex by methylphenidate in cocaine-addicted subjects but not in controls: relevance to addiction. *J Neurosci* 25:3932-3939.

What is claimed is:
1. A compound having the formula:

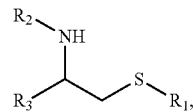

wherein $R_1$ is H, a branched or straight chain $C_1$ to $C_5$ alkyl, or

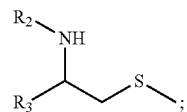

each $R_2$ is independently H or

wherein R₄ is a branched or unbranched $C_1$-$C_6$ alkyl, $C_3$-$C_6$ cycloalkyl, $C_1$-$C_6$ alkoxy, aryloxy, benzyl, or phenyl; and each R₃ is independently

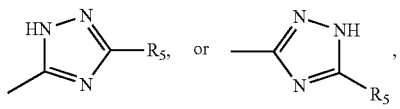

wherein each R₅ is independently H, a branched or unbranched $C_1$-$C_6$ alkyl, $C_3$-$C_6$ cycloalkyl, phenyl, or benzyl;

or a salt or hydrate of said compound.

2. The compound according to claim 1, wherein R₁ is H or

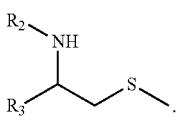

3. The compound according to claim 1, wherein each R₂ is independently H or

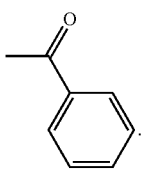

4. The compound according to claim 1, wherein each R₅ is independently H, —CH₂CH₃, —CH(CH₃)₂, or phenyl.

5. The compound according to claim 1, wherein the compound has the formula:

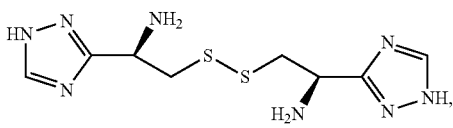

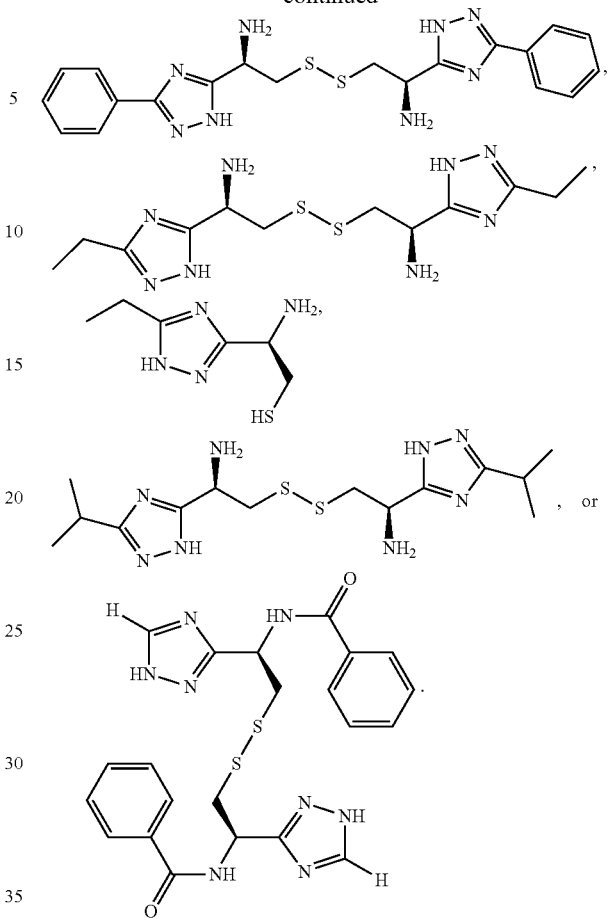

6. A salt of the compound of claim 1, wherein the salt is a hydrochloride salt.

7. A pharmaceutical composition comprising the compound according to claim 1 and a pharmaceutically-acceptable carrier.

8. A method of treating schizophrenia in a subject, comprising administering to said subject an effective amount of a compound according to claim 1, whereby schizophrenia is treated in said subject.

9. The method according to claim 8, wherein the step of administering to said subject is accomplished by oral delivery.

* * * * *